United States Patent
Søe et al.

(10) Patent No.: US 9,493,748 B2
(45) Date of Patent: *Nov. 15, 2016

(54) METHOD FOR TREATING PYROPHEOPHYTIN-CONTAINING COMPOSITIONS

(75) Inventors: Jørn Borch Søe, Tilst (DK); Charlotte Horsmans Poulsen, Braband (DK); Masoud Rajabi Zargahi, Arhus (DK); Jens Frisbæk Sørensen, Aarhus (DK); Tina Jørgensen, Silkeborg (DK); Janne Brunstedt, Rosklide (DK); Rene Mikkelsen, Skanderborg (DK); Susan Mampusti Madrid, Millbrae, CA (US)

(73) Assignee: DUPONT NUTRITION BIOSCIENCES APS (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/321,869

(22) PCT Filed: Jun. 10, 2010

(86) PCT No.: PCT/IB2010/052581
§ 371 (c)(1),
(2), (4) Date: Feb. 29, 2012

(87) PCT Pub. No.: WO2010/143149
PCT Pub. Date: Dec. 16, 2010

(65) Prior Publication Data
US 2012/0149927 A1    Jun. 14, 2012

Related U.S. Application Data

(60) Provisional application No. 61/186,525, filed on Jun. 12, 2009, provisional application No. 61/313,193, filed on Mar. 12, 2010.

(51) Int. Cl.
| | | |
|---|---|---|
| *C12P 7/64* | (2006.01) | |
| *A23D 9/04* | (2006.01) | |
| *C11B 3/00* | (2006.01) | |
| *C12N 9/18* | (2006.01) | |

(52) U.S. Cl.
CPC . *C12N 9/18* (2013.01); *A23L 5/49* (2016.08); *C11B 3/003* (2013.01)

(58) Field of Classification Search
CPC ....... C12N 9/18; A23L 1/0153; A23L 1/277; C11B 3/003; C12Y 301/01014
USPC .................................. 435/197, 271
See application file for complete search history.

(56) References Cited

U.S. PATENT DOCUMENTS

| | | |
|---|---|---|
| 4,683,202 A | 7/1987 | Mullis |
| 5,264,367 A | 11/1993 | Aalrust et al. |
| 5,288,619 A | 2/1994 | Brown et al. |
| 5,315,021 A | 5/1994 | Beharry et al. |
| 5,558,781 A | 9/1996 | Buchold et al. |
| 6,001,640 A | 12/1999 | Loeffler et al. |
| 6,103,505 A | 8/2000 | Clausen et al. |
| 6,162,623 A | 12/2000 | Grote et al. |
| 6,180,406 B1 | 1/2001 | Stemmer |
| 6,344,328 B1 | 2/2002 | Short |
| 6,355,693 B1 | 3/2002 | Herslof et al. |
| 6,361,974 B1 | 3/2002 | Short et al. |
| 6,376,689 B1 | 4/2002 | Muralidhara et al. |

FOREIGN PATENT DOCUMENTS

| | | |
|---|---|---|
| EP | 1103606 | 5/2001 |
| EP | 1138763 | 10/2001 |
| WO | WO 9818912 | 5/1998 |
| WO | WO 0058517 | 10/2000 |
| WO | WO 0134835 | 5/2001 |
| WO | WO 0206457 | 1/2002 |
| WO | WO 0229022 A2 | 4/2002 |
| WO | WO 2006009676 A2 | 1/2006 |
| WO | WO 2006031699 | 3/2006 |

OTHER PUBLICATIONS

GenPept Accession No. NP_196884, May 2009, 2 pages.*
Hussein, A., "Removal of Chlorophyll From Canola Oil", Thesis, University of Toronto, 1992.*
Arkus et al., Arch. Biochem. Biophys. 438:146-155, 2005.*
R.F. McFeeters et al: "Purification and properties of chlorphyllase from *Ailanthus altissima* (tree-of-heaven)", Plant Physiology, vol. 47, 1971, pp. 609-618.
Schelbert Silvia et al: "Pheophytin Pheophorbide Hydrolase (Pheophytinase) Is Involved in Chlorophyll Breakdown during Leaf Senescence in Arabidopsis", Plant Cell, vol. 21, No. 3, Mar. 2009.
Bitar Marianne et al: "Chlorophyllase biocatalysis in an aqueous/miscible organic solvent medium containing canola oil", Journal of the American Oil Chemists' Society, Springer, Berlin, DE LNKD-DOI:10.1007/S11746-004-1003-7, vol. 81, No. 10, Oct. 1, 2004, pp. 927-932.
Database UniProt [Online], Dec. 4, 2007 "SubName: Full-Chlorophyllase I; EC=3.1.1.14"; XP002612123, retrieved from EBI accession No. UNIPROT:A8J2S9 sequence.
De Morais Coutinho C et al: "State of art of the application of membrane technology to vegetable oils: A review", Food Research International, Elsevier Applied Science, Barking, GB LNKD-DOI: 10.1016/J.Foodres. Feb. 10, 2009, vol. 42, No. 5-6, Jun. 1, 2009, pp. 536-550.

(Continued)

*Primary Examiner* — David J Steadman

(57) ABSTRACT

The present invention provides methods and uses for treating pyropheophytin-containing compositions, particularly in order to remove pyropheophytin therefrom. The compositions are typically plant, algal, or bacterial derived products such as vegetable oils. The method comprises a step of contacting the compositions with an enzyme having pyropheophytinase activity. Also provided are related apparatus and products for performing such methods and uses.

10 Claims, 21 Drawing Sheets

(56) References Cited

OTHER PUBLICATIONS

K. Suzuki et al: "Behavior of chlorophyll derivatives in canola oil processing", Jaocs, vol. 70, No. 9, Sep. 1993, pp. 837-841.
International Preliminary Report on Patentability and Written Opinion of the International Searching Authority dated Dec. 22, 2011 for PCT/IB2010/052581.
Johnson-Flanagan et al. "Ethylene Production during Development of Mustart (*Brassica juncea*) and Canola (*Brassica napus*) Seed," *Plant Physiol.*, 1994, vol. 106, pp. 601-606.
Kalmokoff, M.L. et al., "Resistance of green pigments in commercial canola oil to anzymatic hydrolysis," *Canadian Institute of Food Science and Technology Journal*, 1977, vol. 21, No. 5, pp. 534-536.
Karboune et al., "Immobilization and biocatalysis of chlorophyllase in selected organic solvent systems," *J. Biotechnol.*, Nov. 21, 2005, vol. 120. No. 3, pp. 273-283.
Khamessa, A. et al., "Biocatalysis of Chlorophyllase in Canola Oil using Organic Solvent Systems," *Journal of Food Biochemistry*, 1996, vol. 20, No. 4, pp. 311-328.
Levadoux et al., "Pigment Removal from Canola Oil Using Chlorophyllase," *JAOCS*, 1987, vol. 63, No. 1, pp. 139-144.
Takamiya et al., "Degradation pathway(s) of chlorophyll: what has gene cloning revealed?," *Trends in Plant Science Reviews*, 2000, vol. 5, No. 10, pp. 426-431.
Altschul et al., "Basic Local Alignment Search Tool," *J. Mol. Biol.*, 1990, vol. 215, pp. 403-410.
Ausubel et al., "Short Protocols in Molecular Biology," 1999, John Wiley, 4$^{th}$ edition, Chapter 18.
Ausubel et al, "Short Protocols in Molecular Biology," 1999, pp. 7-58 to pp. 7-60.
Beaucage, S.L. et al., "Deoxynucleoside phosphoramidites—a new class of key intermediates for deoxypolynucleotide synthesis," *Tetrahedron Letters*, 1981, vol. 22, No. 20, pp. 1859-1869.
Bockisch, M., "Fats and Oils Handbook, the extraction of Vegetable oils," 1998, Chapter 5, pp. 345-445, AOCS Press, Champaign, IL, ISBN 9780935315820.
Caruthers, M.H. et al., "New chemical methods for synthesizing polynucleotides," *Nucleic Acids Research Symposium Series*, No. 7, 1980, pp. 215-223.
Horn et al., Synthesis of oligonucleotides on cellulose. Part II: design and synthetic strategy to the synthesis of 22 oligodeoxynucleotides coding for Gastric Inhibitory Polypeptide (GIP), *Nucleic Acids Research Symposium Series*, 1980, pp. 225-232.
Hornero-Méndez, D. et al., "Routine and sensitive SPE-HPLC method for quantitative determination of pheophytin α and pyropheophytin α in olive oils," *Food Research International*, 2005, vol. 38, issue 8-9, pp. 1067-1072.
Horwell, D.C., "The 'peptoid' approach to the design of non-peptide, small molecule agonists and antagonists of neuropeptides," *Trends Biotechnol.*, 1995, vol. 13, No. 4, pp. 132-134.
Huang, S.C. et al., "Determination of chlorophylls and their derivatives in Gynostemma pnetaphyllum Makino by liquid chromatography mass spectrometry," *Journal of Pharmaceutical and Biomedical Analysis*, 2008, vol. 48, No. 1, pp. 105-112.
Khalyfa, A. et al., "Extraction, Purification, and Characterization of Chlorophylls from Spinach Leaves," *Journal of Agricultural and Food Chemistry*, 1992, vol. 40, No. 2, pp. 215-220.
Marchler-Bauer, A. et al., "CDD: a curated Entrez database of conserved domain alignments," *Nucleic Acids Research*, 2003, vol. 31, No. 1, pp. 383-387.
Matthes, HWD. et al., "Simultaneous rapid chemical synthesis of over one hundred oligonucleotides on a microscale," *EMBO J*, 1984, vol. 3, pp. 801-805.
Minguez-Mosquera, M.I. et al., "Determination of chlorophylls and carotenoids by high-performance liquid chromatography during olive lactic fermentation," *Journal of Chromatography*, 1991, vol. 585, No. 2, pp. 259-266.
Morinaga, Y. et al., "Improvement of oligonucleotide-directed site-specific mutagenesis using double-stranded plasmid DNA," *Biotechnology*, 1984, vol. 2, pp. 646-649.
Nelson, R.M. et al., "A general method of site-specific mutagenesis using a modification of the Termus aquatics Polymerse chain reaction," *Analytical Biochemistry*, 1989, vol. 180, pp. 147-151.
Saiki, R.K. et al., "Primer-directed enzymatic amplification of DNA with a thermostable DNA Polymerase," Science, 1988, vol. 239, pp. 487-491.
Simon, R.J. et al., "Peptoids: a modular approach to drug discovery," *Proc. Natl. Acad. Sci.*, 1992, vol. 89, No. 2, pp. 9367-9371.
Tatusova, TA et al., "Erratum to BLAST 2 Sequences, a new tool for comparing protein and nucleotide sequences," *FEMS Microbiol. Lett.*, 1999, vol. 174, No. 2, pp. 247-250.
Yi, Y. et al., "Encapsulation of chlorophyllase in hydrophobically modified hydrogel," *J. Molecular Catalysis B: Enzymatic*, 2002, vol. 19, pp. 319-325.
NCBI GenBank accession No. NM_123753 *Arabidopsis thaliana* STCLH2; chlorophyllase (CLH2) mRNA, 2009.
NCBI Protein accession No. BAG91172 unnamed protein product [Oryza sativa Japonica Group], 2008.
NCBI Protein accession No. BAH19780 gene AT5G13800 *Arbidopsis thaliana*, 2009.
NCBI Protein accession No. CA099125 putative esterase [*Nicotiana tabacum*], 2007.
NCBI Protein accession No. NP_001057593 Os06g0354700 [Oryza sativa (japonica cultivar-group)], 2008.
NCBI Protein accession No. NP001141976 hypothetical protein LOC100274126 [*Zea mays*], 2009.
NCBI Protein accession No. NP_196884 GenBank ID No. G115240707 *Arabidopsis thaliana*, 2009.
NCBI Protein accession No. P59677-1 Chlorophyll-chlorophyllido hydrolase 1, 2009.
NCBI Protein accession No. P59678 Chlorophyll-chlorophyllido hydrolase 2, 2009.
NCBI Protein accession No. XP_001761725 predicted protin [Physcomitrella patens subsp. patents], 2009.
NCBI Protein accession No. XP_002271167 predicted: hypothetical protein [*Vitis vinifera*], 2009.
NCBI Protein accession No. XP_002314066 predicted protein [*Populus trichocarpa*], 2009.

\* cited by examiner

Figure 10
SEQ ID NO:1

```
  1 MEIISLNVVP QCSVVTWSSK LATKRLVPNR SSLLFSGVKK SRLVIRSGNS DGYVVGENDD
 61 LGRIARRGES TSKVLIPGLP DESNGEIAAR ISHSHCEWKP KLRVHYEKAG CDNLDAPAVL
121 FLPGFGVGSF HYEKQLTDLG RDYRVWAIDF LGQGLSLPTE DPTTMTEETS SSEDKEPFWG
181 FGDKTEPWAD QLVFSLDLWR DQVQYFVEEV IGEPVYIAGN SLGGYVALYF AATHPHLVKG
241 VTLLNATPFW GFFPNPVRSP KLARLFPWPG AFPLPERVKK ITELVWQKIS DPESIAEILK
301 QVYTDHSINV DKVFSRIVEV TQHPAAAASF ASIMLAPGGE LSFSEALSRC KENNVQICLM
361 YGREDPWVRP LWGKKIKKEI PNAPYYEISP AGHCPHDEVP EVVNYLMRGW IKHLESGGFE
421 ALPLLEDTEE DWEESRIGRE IEFPRDGWKK AVNLWLYGSN YTYWRGVRES FRSSFIRVFG
481 GKSA
```

Figure 11
SEQ ID NO:2

```
   1 aacccaattc ttctatttct tcttcacctt tagattttc ctcgcttaat ttctcaataa
  61 cgctctcaga gagaccattt gatgaagctt ctcgcttctg gaatttgaaa aggatttgat
 121 aagacgagtt catagaagat taccgcaagt tcatcaactt tttgaacttg ttatggagat
 181 aatctcactg aacgttgtgc cccagtgctc tgtggttact tggagtagta aattagcaac
 241 gaaaagattg gtcccaaatc ggtcaagttt gttattctca ggggtcaaaa aatccagact
 301 tgtgattcga agtggaaatt ccgatggtta tgttgttggt gagaatgatg acttgggtcg
 361 tatagccaga agaggagaat caacgtcaaa ggttttgatt cctggtttgc ctgatgaatc
 421 aaatggtgaa attgctgctc gaatcagtca ttctcactgc gagtggaagc caagcttag
 481 agtacattat gagaaagccg ttgtgacaa tctcgatgct cctgcggtgt tgtttcttcc
 541 tggctttggc gttggttcat tcactatga aagcagctt accgatttgg aagggatta
 601 tcgagtatgg gctattgatt tcttggaca gggtttatct ctccctactg aagatcctac
 661 taccatgact gaagaaacca gttcctcgga agataaggaa ccattttggg gatttggtga
 721 caaaactgaa ccgtgggctg atcaacttgt attctctctg gatctctgga gggatcaagt
 781 tcagtatttt gtagaagagg ttatcggtga gcctgtgtac attgcaggga actcacttgg
 841 agggtatgta gctctctact ttgcagcaac ccatcctcac ctggttaagg gtgttacctt
 901 gcttaatgca cacctttct ggggttttctt ccctaatcca gtaagatccc aaagctagc
 961 acgtctcttt ccatggcccg gagcattccc tctgccggaa agagtgaaaa aaatcacaga
1021 attggtgtgg caaaagataa gtgatcctga aagcatagct gagatactta acaggtcta
1081 cacagaccat tctatcaatg tggataaagt attctcacgt attgtggagg tcacacagca
1141 tccggctgct gcagcatcgt ttgcttcaat catgcttgct cctggtggag agctatcttt
1201 ctccgaagct tatctaggt gtaaggaaaa caatgttcag atatgtctca tgtatggaag
1261 agaagatcca tgggtgagac cgttatgggg aaagaagata agaaggaaa tccccaacgc
1321 tccatactac gagatcagcc cagcgggtca ctgcccacac gatgaagtcc ctgaggtggt
1381 gaactatctg atgcgcgggt ggatcaagca cctggagtct ggtggttttg aagcgctccc
1441 gcttttggag gacactgaag aagattggga ggagtccagg attggtagag aaattgagtt
1501 cccgagagat ggttggaaaa agcagtgaa tctgtggtta tagggtcaa actatacgta
1561 ctggagagga gttagagaat ctttcagatc cagttttata agggtgtttg gagggaagtc
1621 tgcatagaag aagcatggaa cagtcgtcta gtgtaaatta attgtaatct atgttgcatc
1681 cgatgctagc tatataatgt tgtctgtaga atcaagtttc taaaatgttc aaaaggaaaa
1741 gttagaaaaa tatctacttg atagttagtc acctaaatcg aaggaactcc tttcttgcat
1801 tgttgtatat aatccacagg ttcagattaa tataggaagg cgacattgca ggc
```

Figure 12

```
      T  S  V  A     V  E  K     R  S  G     N  S  D  G     Y  V  V     G  E  N     D  D  L  G     R  I  A     R  R  G     E  S  T  S
   1  ACTAGTGTCG CCGTCGAGAA GCGCAGCGGC AACAGCGACG GCTACGTCGT CGGCGAGAAC GACGACCTCG GCCGCATTGC CCGACGCGGC GAGAGCACCA
         K  V  L     I  P  G     L  P  P  D  E     S  N  G     E  I  A     A  R  I  S     H  S  H     C  E  W     K  P  K  L     R  V  H
 101  GCAAGGTCCT CATCCCCGGC CTCCCCGACG AGAGCAACGG CGAGATCGCC GCCACAGCCA CTCGCAGTGG AAGCCCAAGC TCCGCGTCCA
         Y  E  K     A  G  C  D     N  L  D     A  P  A     V  L  F  L     P  G  F     G  V  G     S  F  H  Y     E  K  Q     L  T  D
 201  CTACGAGAAG GCCGGCTGCG ACAACCTCGA CGCCCCCTGC GTCCTCTTCC TCCCCGGCTT CGGCGTCGGC AGCTTTCACT ACGAGAAGCA GCTCACCGAC
         L  G  R  D     Y  R  V     W  A  I     D  F  L  G     Q  G  L     S  L  P     T  E  D  P     T  T  M     T  E  E     T  S  S  S
 301  CTGGGCCGCG ACTACCGCGT CTGGGCCATC GACTTTCTCG GCCAGGGCCT CAGCCTCCCC ACCGAGGACC CCACCACCAT GACCGAGGAG ACCAGCAGCA
         E  D  K     E  P  F     W  G  F  G     D  K  T     E  P  W     A  D  Q  L     V  F  S     L  D  L     W  R  D  Q     V  Q  Y
 401  GCGAGGACAA GGAGCCCTTC TGGGGCTTCG GCGACAAGAC CGAGCCCTGG GCCGACCAGC TCGTCTTTAG CCTCGACCTC TGGCGCGACC AGGTCCAGTA
         F  V  E     E  V  I  G     E  P  V     Y  I  A     G  N  S  L     G  G  Y     V  A  L     Y  F  A  A     T  H  P     H  L  V
 501  CTTCGTCGAG GAGGTCATCG GCGAGCCCGT CTACATTGCC GGCAACAGCC TCGGCGGCTA CGTCGCCCTC TACTTCGCCG CCACCCACCC CCACCTCGTC
         K  G  V  T     L  L  N     A  T  P     F  W  G  F     F  P  N     P  V  R     S  P  K  L     A  R  L     F  P  W     P  G  A  F
 601  AAGGGCGTCA CCCTCCTCAA CGCCACCCCC TTTTGGGGCT TTTTCCCCAA CCCCGTCCGC AGCCCCAAGC TCGCCCGCCT CTTCCCTTGG CCTGGCGCCT
         P  L  P     E  R  V     K  K  I  T     E  L  V     W  Q  K     I  S  D  P     E  S  I     A  E  I     L  K  Q  V     Y  T  D
 701  TCCCGCTCCC CGAGCGCGTC AAGAAGATCA CCGAGCTGGT CTGGCAGAAG ATCAGCGACC CCGAGTCGAT CGCCGAGATC CTCAAGCAGG TCTACACCGA
         H  S  I     N  V  D  K     V  F  S     R  I  V     E  V  T  Q     H  R  A     A  A  A     S  F  A  S     I  M  L     A  P  G
 801  CCACAGCATC AACGTCGACA AGTTCTTTAG CCGCATCGTC GAGGTCACCC AGCACCGCGC CGCCGCTGCC AGCTTCGCCT CCATCATGCT GGCCCCTGGC
         G  E  L  S     F  S  E     A  L  S     R  C  K  E     N  N  V     Q  I  C     L  M  Y  G     R  E  D     P  W  V     R  P  L  W
 901  GGCGAGCTGA GCTTCAGCGA GGCCCTCAGC CGTTGCAAGG AGAACAACGT CCAGATCTGC CTCATGTACG GCCGCGAGGA CCCCTGGGTC CGCCCCCTCT
         G  K  K  I     I  K  K     E  I  P  N     A  P  Y     Y  E  I     S  P  A  G     H  C  P     H  D  E     V  P  E  V     V  N  Y
1001  GGGGCAAGAA GATCAAGAAG GAGATCCCCA ACGCCCCCTA CTACGAGATC AGCCCTGCCG GCCACTGCCC CCACGACGAG GTCCCCGAGG TCGTCAACTA
         L  M  R     G  W  I  K     H  L  E     S  G  G     F  E  A  L     P  L  L     E  D  T     E  E  D  W     E  E  S     R  I  G
1101  CCTCATGCGC GGCTGGATCA AGCACCTGGA GAGCGGCGGC TTCGAGGCCC TGCCCCTGCT CGAGGACACC GAGGAGGACT GGGAGGAGAG CCGCATCGGC
         R  E  I  E     F  P  R     D  G  W     N  K  K  A     V  N  L  W     L  Y  G     S  N  Y  T     Y  W  R     G  V  R     E  S  F  R
1201  CGCGAGATCG AGTTCCCCCG CGACGGCTGG AACAAGAAGG CCGTGAACCT CTGGCTCTAC GGCTCCAACT ACACCTACTG GCGCGGCGTC CGCGAGAGCT TCCGC
         S  S  F     I  R  V     F  G  G  K     S  A  *
1301  GCAGCAGCTT CATCCGCGTC TTTGGGGGCA AGAGCGCCTA ATAGGGCGCG CC
```

Figure 15

SEQ ID NO:5

```
  1  MMILAFFLIF MEFYFQLRRR YASYLLINMI LLITADQPFW GMEILTSSTA SCCLVVNLRW
 61  KLAENGSNSS QLKLPTSRER KILFARTNQR NGSLRFSSVD KFLKKLNHGK GSRSLDSFGG
121  LKNGNSKVFS GNSSSYVVGG EDDVGSITEN GESPTKVLIP GLPDESNGEY SAPVSSCFWK
181  WKPKLNVHYE KAGCENVNSP PVLFLPGFGV GSFHYEKQLK DLGRDYRVWA IDFLGQGMSL
241  PVENPTLFSK DGAASEGKDS IWGFGDEIEP WANDLVFSMD LWQDQVHNFI EEVIGEPVYI
301  VGNSLGGFVA LYFAARYPHL VKGVTLLNAT PFWGFLPNPI RSPRLARIFP WSGTFPLPAN
361  VRKLIAFFWQ KISDPKSIAE ILKQVYTDHS TNIDKVFSRI LEITQHPAAA ASFASIMFAP
421  QGQLSFRETL ARCKMSDTPI CLVYGKEDPW VKPVWGLQVK QQVPEAPYYE ISPAGHCPHD
481  EVPEAVNYLL RGWIKNLESH GSVALPLHED AEVVENSFAM DLEFVREGSR KSVIVRFFGS
541  RFSIWNSFSS YIKSQFKETT SRILTP
```

Figure 16

SEQ ID NO:6

```
  1  MEILSCHSAP CCKLVNLGGT SVHKSSGSSQ AKLPGSRNNR ILCARIGSKL GSSGYSNLDD
 61  FCTKNFGRHE GSRSLTAFKG SANVNSKALS ESYNGYVIDG KEGVGDISER GDLITQILIP
121  GLPDDSNDDS GAQISSCFWE WKPKLTVHYE KSGCENVNSP PVLFLPGFGV GSFHYEKQLK
181  DLGRDFRVWA VDFLGQGMSL PFEDPAPQSK KELDSERNDF SWGFGDETEP WANELVYSID
241  LWQDQVRYFI EQVIGEPVYI VGNSLGGFVA LYFAACNPQL VKGVTLLNAT PFWGFLPNPS
301  RSPSLARIFP WAGTFPLPAF VRKLTEFVWQ KISDPRSIGE VLKQVYADHS TKVDKVFSRI
361  LETTQHPAAA ASFASIMFAP QGQLSFSEAL SRCQMSNVPI CLMYGKEDPW VRPVWGLQVK
421  RQLLEAPYYE ISPAGHCPHD EVPEVVNYLL RGWIGNLESK GSVTLPLLDD PENIQYGTTK
481  DLEFVREGSK KSVRVHFYGS RFSLWNRIRS YVKSRFEALE INSR
```

Figure 17

SEQ ID NO:7

```
  1  MFSPCPLISS GQTQWLDLGM DILTFNVTTS HRTAHFGSKL VDKTKYSCKS KVSTIIKPQV
 61  FCARIDQSCG LLRFSSSNKF LDYPKKIEVS KKHNALKGIK VVNSKVLSGN YNGYVIEADE
121  DMESVSGSGE STPEILIPGL PNESSGECGA PINSCFWEWK PKLYVHYEKA GCENVKSPPV
181  LFLPGFGVGS FHFENQLKDL GRDYRVWAID FLGQGMSLPV ENPTLQLREG DILEGKNSFW
241  GFGDETEPWA NELVYSMDLW RDQVRYFIEE VIGEPVYVVG NSLGGFVAIY FAASNPQLVK
301  GVTLLNATPF WGFLPNPIRS PRLARIIPWS GTFPLPASVR KLTEFFWQKI SDPKSIAQVL
361  KQVYADHSTN VDQVFSRILK ITQHPAAAAS FASIMFAPQG QLSFRECLMR CKMNNLPICL
421  LYGREDPWVK PIWGLQVKRQ VPEASYYEIS PAGHCPHDEV PEVCSLSLFL VGIPLLFLVI
481  L
```

Figure 18

SEQ ID NO:8

```
  1   MEVVSSSHSC LAFNRTPSSA WRFPGNGLGP GHAKLTRPRS AILCVRSGTA SNPADSGKVH
 61   ASHGFYVSDV DAALQGIPKK VGEIEKMIIP SLPEGPESSL ISTGFWEWKP KLSVYYEKSG
121   IDNSKAPSVL FLPGFGVGTF HFEKQLKDLG RDYKVWTMDF LGQGMSLPCE DPAPKSTSGE
181   LDEDTYWGFG QELQPWAEEL VYSIDLWRDQ VQHFIEEVIG EPVYIVGNSL GGFVSLYLAA
241   SCPHLVKGVT LLNATPFWGF LPNPATSPRL SKIFPWAGTF PLPSFVRKLT ETVWQKISDP
301   RSIQGILKQV YADHSTNVDM VFSRIIETTQ HPAAAASFAS IMCAPKGQIS FEEALSRCQR
361   QGIPISLMYG REDPWVRPIW GIKVKQQVPE SPYYEISPAG HCPHDEVPEV INYLLRGWLK
421   NVESEGSVAV PFLEEPSYAE NGVSRELEFV RGGSKKSVHV RLFGSKISLW SQLRSLLKSN
481   TWVISR
```

Figure 19

SEQ ID NO:9

```
  1   MEVVSCSHSC SALHQTPAST WRLRGSALGL GLGHARPSRT RRYTVACVGT TSGASNPGGS
 61   GKVHAAQGFH VSDVDAALQG IPSMKAGEAE RVMIQGLPEG PDSSPISTGF WEWKPKLTVH
121   YERSGMKNSK APAVLFLPGF GVGTFHFEKQ LRDLGRDHRV WTMDFLGQGM SLPGEDPAPS
181   SIASEDAFWG FGQDSQPWAE ELVYSVDLWQ NQVQHFIEEV IREPVYIVGN SLGGFVALYF
241   AASSPHLVKG VTLLNATPFW GFFPNPATSP RLSKIFPWAG TFPLPSFVRK ITEAVWQKIS
301   DPKSIQDILK QVYADHSTNV DKVFSRIVEI TQHPAAAASF ASIMFAPRGQ ISFQEAISRC
361   QDQGIPISLM YGREDPWIRP IWGLKVKQQV PEAPYYEISP AGHCPHDEVP EVINYLLRGW
421   LKNLESEGSV DLPFLEERSY AERGVSRELE FVREGSRKSV SVRLYGTKIS LWSQLSSFLN
481   TRVPKSRIVL R
```

Figure 20

SEQ ID NO:10

```
  1   MEVHSCYSTT YYCIVNVSKC LISNQAKFPI VKERRLYSGL DVYSIKKKRT QRLTITALKG
 61   FDSVDSSLLS ESYNSDIIDG KVGTQDVIGS AKSVPKVIVP SLPDETKADS VAVVDSCLWE
121   WKPKLKVHYE KSGCQNVNSA PILFLPGFGV GSFHYEKQLK DLGCDHRIWA LDFLGQGKSL
181   PCEDPTLQSK RLDESERDGN NAVWGFGDEA EPWAKELVYS VDLWRDQVRY FIEEVIKEPV
241   YIVGNSLGGY VALYLAAYYP QLVKGVTLLN ATPFWGFLPN PVRSPRLSRL FPWAGTFPLP
301   DTIRKLTELV WQKISAPESI AEVLKQVYAD HTTKVDKVFS SILEVTEHPA AAASLASILF
361   APRGQLSFKE ALTGCRMNNV PVCLMYGKED PWVMPFWALQ VKRQLPEAPY YQISPAGHCP
421   HDEVPEIVNF LLRGWIKNIE SHSSVALPLL DSPESIEYDI VRDLEFVRQG MKKSVRVQFY
481   GSMTSQWEKL GMFLKSRFQY GVYSP
```

Figure 21

SEQ ID NO:11

```
  1   MEVVSSSHSC  LAFNRTPSSA  WRFPGNGLGP  GHAKLTRPRS  AILCVRSGTA  SNPADSGKVH
 61   ASHGFYVSDV  DAALQGIPKK  VGEIEKMIIP  SLPEGPESSL  ISTGFWEWKP  KLSVYYEKSG
121   IDNSKAPSVL  FLPGFGVGTF  HFEKQLKDLG  RDYKVWTMDF  LGQGMSLPCE  DPAPKSTSGE
181   LDEDTYWGFG  QELQPWAEEL  VYSIDLWRDQ  VQHFIEEVIG  EPVYIVGNSL  GGFVSLYLAA
241   SCPHLVKGVT  LLNATPFWGF  LPNPATSPRL  SKIFPWAGTF  PLPSFVRKLT  ETVWQKISDP
301   RSIQGILKQV  YADHSTNVDM  VFSRIIETTQ  HPAAAASFAS  IMCAPKGQIS  FEEALSRCQR
361   QGIPISLMYG  REDPWVRPIW  GIKVKQQVPE  SPYYEISPAG  HCPHDEVPEV  PGKSLAWWIT
421   GRLQAS
```

Figure 22a

SEQ ID NO:12

```
  1   IASHIWEWRH  RWNIHYECAG  TSLNTNAPAM  LLLPGFGVGS  FHYHQQLRDL  GQEYRVWAID
 61   FLGQGKSWPS  HDPAPEEAEE  VVEEIRHWSL  GKNPEPWAEG  LVYSVDTWRD  QVHAFIEKVI
121   GGPVYIVGNS  LGGYVGSYFA  ATNPELVKGV  TLLNATPFWA  FTPNSRRYPL  LSKLTPWGGL
181   LPVPIFAKAI  IRFWWDLLRN  PSTIRNMLGA  VYANRSAINK  KLITQIIEAT  DHPAAFAAFA
241   SIVFAPRAHT  DFGENLISLK  ERRMPMCMIY  GKEDPWVVPF  WGQRAKQRNP  DAIYYELSPA
301   GHCPHHEAPE  VLFPAQIVLL  ACMVQNIIGK  ARPLFKG
```

Figure 22b

SEQ ID NO:20

```
  1   MSSSSSRNAF  EDGKYKSNLL  TLDSSSRCCK  ITPSSRASPS  PPKQLLVATP  VEEGDYPVVM
 61   LLHGYLLYNS  FYSQLMLHVS  SHGFILIAPQ  LYSIAGPDTM  DEIKSTAEIM  DWLSVGLNHF
121   LPAQVTPNLS  KFALSGHSRG  GKTAFAVALK  KFGYSSNLKI  STLIGIDPVD  GTGKGKQTPP
181   PVLAYLPNSF  DLDKTPILVI  GSGLGETARN  PLFPPCAPPG  VNHREFFREC  QGPAWHFVAK
241   DYGHLDMLDD  DTKGIRGKSS  YCLCKNGEER  RPMRRFVGGL  VVSFLKAYLE  GDDRELVKIK
301   DGCHEDVPVE  IQEFEVIM
```

Figure 23

Figure 27
SEQ ID NO. 21

```
  1 MAAAAPAETM NKSAAGAEVP EAFTSVFQPG KLAVEAIQVD ENAAPTPPIP VLIVAPKDAG
 61 TYPVAMLLHG FFLHNHFYEH LLRHVASHGF IIVAPQFSIS IIPSGDAEDI AAAAKVADWL
121 PDGLPSVLPK GVEPELSKLA LAGHSRGGHT AFSLALGHAK TQLTFSALIG LDPVAGTGKS
181 SQLQPKILTY EPSSFGMAMP VLVIGTGLGE EKKNIFFPPC APKDVNHAEF YRECRPPCYY
241 FVTKDYGHLD MLDDDAPKFI TCVCKDGNGC KGKMRRCVAG IMVAFLNAAL GEKDADLEAI
301 LRDPAVAPTT LDPVEHRVA
```

Figure 28
SEQ ID No. 22

```
  1 GCGCGCAGGC TGCTGGAAAA ATGGCAGCGG CTGCCCCGGC CGAAACAATG AATAAAAGCG
 61 CAGCGGGTGC CGAAGTTCCT GAAGCATTTA CGTCTGTGTT TCAACCGGGC AAATTGGCTG
121 TCGAAGCCAT TCAGGTAGAC GAAAACGCTG CCCCTACACC GCCTATTCCG GTCCTGATCG
181 TAGCACCTAA AGATGCGGGA ACGTATCCGG TCGCGATGCT GCTTCATGGC TTTTTCCTGC
241 ATAACCATTT TTACGAACAT TTGTTGCGTC ATGTCGCGTC CCATGGATTT ATCATCGTAG
301 CTCCTCAATT TTCAATTAGC ATTATCCCGT CAGGCGACGC GGAAGATATC GCAGCGGCTG
361 CCAAAGTTGC TGACTGGCTG CCGGATGGCC TTCCTAGCGT TTTACCGAAA GGCGTTGAAC
421 CTGAACTTTC TAAACTGGCT CTTGCCGGAC ATTCCCGCGG CGGACATACA GCTTTTTCAT
481 TAGCCTTGGG CCATGCAAAA ACACAGTTAA CGTTTTCTGC CCTGATTGGA CTTGATCCGG
541 TTGCAGGTAC AGGCAAATCA AGCCAATTGC AGCCTAAAAT CCTGACGTAT GAACCGTCTT
601 CCTTTGGCAT GGCTATGCCT GTTCTTGTGA TTGGAACAGG TTTGGGCGAA GAAAAGAAAA
661 ATATTTTCTT TCCGCCGTGC GCCCCGAAAG ATGTTAACCA TGCAGAATTT TATCGTGAAT
721 GCCGGCCGCC TTGTTATTAC TTTGTGACAA AAGACTACGG ACATTTAGAT ATGTTGGATG
781 ACGATGCACC GAAATTTATT ACGTGCGTCT GTAAAGATGG AAATGGTTGC AAAGGTAAAA
841 TGAGACGCTG TGTCGCGGGC ATTATGGTAG CATTTCTGAA CGCAGCGCTG GGCGAAAAAG
901 ACGCGGATCT TGAAGCTATC TTAAGAGACC CGGCAGTTGC GCCGACAACG CTTGATCCGG
961 TTGAACATCG CGTGGCTTAA TTAA
```

Figure 29
SEQ ID No. 23
```
  1 MPSTQFLGAS TLLLFGLRAV MSSDDYIKRG DLPTSKWSGR VTLRVDSAMA VPLDVVITYP
 61 SSGAAAYPVL VMYNGFQAKA PWYRGIVDHV SSWGYTVVQY TNGGLFPIVV DRVELTYLEP
121 LLTWLETQSA DAKSPLYGRA DVSRLGTMGH SRGGKLAALQ FAGRTDVSGC VLFDPVDGSP
181 MTPESADYPS ATKALAAAGR SAGLVGAAIT GSCNPVGQNY PKFWGALAPG SWQMVLSQAG
241 HMQFARTGNP FLDWSLDRLC GRGTMMSSDV ITYSAAFTVA WFEGIFRPAQ SQMGISNFKT
301 WANTQVAARS ITFDIKPMQS PQ
```

Figure 30
SEQ ID No. 24
```
  1 GCGCGCAGGC TGCTGGAAAA ATGCCTTCTA CACAATTTCT TGGAGCATCC ACGCTGCTTT
 61 TATTTGGTTT ACGTGCGGTC ATGTCAAGCG ATGACTATAT TAAACGGGGT GATTTGCCGA
121 CATCAAAATG GAGCGGAAGA GTCACGTTGC GCGTAGATTC AGCTATGGCC GTTCCGCTGG
181 ACGTTGTGAT CACATATCCT TCTTCCGGCG CAGCGGCTTA TCCGGTCCTG GTAATGTACA
241 ATGGATTTCA GGCAAAAGCG CCGTGGTACA GAGGCATTGT TGATCATGTG TCAAGCTGGG
301 GATATACAGT CGTACAATAC ACGAACGGCG GACTTTTTCC TATCGTTGTG GACCGCGTCG
361 AACTTACATA TTTAGAACCG TTGCTGACAT GGTTAGAAAC GCAGTCTGCT GATGCCAAAT
421 CCCCGTTGTA CGGCAGAGCT GACGTATCAC GCCTGGGCAC AATGGGACAT AGCAGAGGTG
481 GCAAATTGGC CGCACTGCAA TTTGCGGGCC GCACGGATGT TCAGGATGC GTGCTTTTTG
541 ATCCTGTGGA CGGCAGCCCG ATGACACCTG AATCAGCTGA CTATCCGAGC GCTACGAAAG
601 CACTTGCGGC TGCCGGACGT TCTGCCGGTT TAGTTGGCGC AGCGATTACA GGTTCATGTA
661 ATCCGGTGGG CCAGAACTAC CCTAAATTTT GGGGAGCATT GGCGCCTGGT TCATGGCAAA
721 TGGTCCTGAG CCAGGCAGGC CATATGCAAT TTGCGAGAAC AGGAAATCCG TTTTTAGATT
781 GGAGCCTTGA CCGTTATGC GGACGGGGTA CGATGATGTC TTCCGATGTC ATCACATATT
841 CTGCTGCCTT TACGGTAGCT TGGTTTGAAG CATTTTTCG TCCGGCCCAA TCTCAGATGG
901 GAATCTCCAA TTTTAAAACA TGGGCAAACA CGCAAGTTGC AGCGCGGTCT ATTACATTTG
961 ATATCAAACC GATGCAATCC CCTCAGTAAT TAATTAA
``` aprEss-TRI CHL
1059 bp aprEss-CHL CHL
1068 bp

Figure 35
SEQ ID NO. 25

```
                AEVP EAFTSVFQPG KLAVEAIQVD ENAAPTPPIP VLIVAPKDAG
TYPVAMLLHG FFLHNHFYEH LLRHVASHGF IIVAPQFSIS IIPSGDAEDI AAAAKVADWL
PDGLPSVLPK GVEPELSKLA LAGHSRGGHT AFSLALGHAK TQLTFSALIG LDPVAGTGKS
SQLQPKILTY EPSSFGMAMP VLVIGTGLGE EKKNIFFPPC APKDVNHAEF YRECRPPCYY
FVTKDYGHLD MLDDDAPKFI TCVCKDGNGC KGKMRRCVAG IMVAFLNAAL GEKDADLEAI
LRDPAVAPTT LDPVEHRVA
```

Figure 36

SEQ ID No. 26

```
  1 GCGCGCAGGC TGCTGGAAAA GCCGAGGTCC GGAAGCCTT TACCAGCGTC TTCCAGCCTG
 61 GCAAGCTTGC CGTCGAGGCC ATCCAGGTCG ATGAAAACGC TGCTCCTACC CCGCCCATCC
121 CGGTCCTGAT TGTCGCTCCG AAAGACGCCG GCACGTACCC TGTCGCCATG CTGCTCCATG
181 GCTTTTTCCT CCACAACCAT TTTTATGAGC ACCTTCTGCG CCATGTCGCC TCCCACGGCT
241 TTATCATTGT CGCCCCTCAG TTCAGCATCT CCATCATTCC CTCTGGCGAT GCCGAAGACA
301 TTGCTGCCGC CGCCAAAGTC GCTGATTGGC TGCCTGATGG CCTCCCGAGC GTCCTTCCTA
361 AGGGCGTTGA GCCTGAACTC TCTAAACTCG CCCTTGCTGG CCATTCGCGC GGCGGCCATA
421 CAGCTTTTAG CCTGGCTCTG GGCCACGCCA AAACACAGCT GACCTTCAGC GCCCTTATTG
481 GCCTGGACCC GGTCGCTGGC ACAGGCAAGA GCTCCCAGCT CCAGCCCAAA ATTCTTACAT
541 ACGAGCCGTC TTCGTTCGGC ATGGCCATGC CGGTCCTGGT CATTGGCACA GGCCTCGGCG
601 AGGAAAAGAA AAACATCTTT TTCCCGCCCT GCGCCCCGAA GGATGTCAAC CATGCCGAGT
661 TTTACCGCGA ATGCCGCCCG CCTTGCTACT ATTTCGTCAC AAAAGATTAT GGCCACCTCG
721 ACATGCTTGA CGATGACGCC CCGAAGTTTA TTACCTGCGT CTGCAAAGAC GGCAACGGCT
781 GCAAGGGCAA AATGCGCAGA TGCGTCGCCG GCATCATGGT CGCCTTCCTG AACGCTGCTC
841 TGGGCGAGAA GGATGCTGAC CTTGAAGCCA TTCTGCGCGA TCCCGCCGTC GCTCCCACCA
901 CACTGGACCC TGTCGAACAC CGCGTCGCTT AATTAA
```

SEQUENCE LISTING

<160> NUMBER OF SEQ ID NOS: 83

<210> SEQ ID NO 1
<211> LENGTH: 484
<212> TYPE: PRT
<213> ORGANISM: Arabidopsis thaliana

<400> SEQUENCE: 1

```
Met Glu Ile Ile Ser Leu Asn Val Val Pro Gln Cys Ser Val Val Thr
1               5                   10                  15

Trp Ser Ser Lys Leu Ala Thr Lys Arg Leu Val Pro Asn Arg Ser Ser
            20                  25                  30

Leu Leu Phe Ser Gly Val Lys Lys Ser Arg Leu Val Ile Arg Ser Gly
        35                  40                  45

Asn Ser Asp Gly Tyr Val Val Gly Glu Asn Asp Asp Leu Gly Arg Ile
    50                  55                  60

Ala Arg Arg Gly Glu Ser Thr Ser Lys Val Leu Ile Pro Gly Leu Pro
65                  70                  75                  80

Asp Glu Ser Asn Gly Glu Ile Ala Ala Arg Ile Ser His Ser His Cys
                85                  90                  95

Glu Trp Lys Pro Lys Leu Arg Val His Tyr Glu Lys Ala Gly Cys Asp
            100                 105                 110

Asn Leu Asp Ala Pro Ala Val Leu Phe Leu Pro Gly Phe Gly Val Gly
        115                 120                 125

Ser Phe His Tyr Glu Lys Gln Leu Thr Asp Leu Gly Arg Asp Tyr Arg
    130                 135                 140

Val Trp Ala Ile Asp Phe Leu Gly Gln Gly Leu Ser Leu Pro Thr Glu
145                 150                 155                 160

Asp Pro Thr Thr Met Thr Glu Thr Ser Ser Glu Asp Lys Glu
                165                 170                 175

Pro Phe Trp Gly Phe Gly Asp Lys Thr Glu Pro Trp Ala Asp Gln Leu
            180                 185                 190

Val Phe Ser Leu Asp Leu Trp Arg Asp Gln Val Gln Tyr Phe Val Glu
        195                 200                 205

Glu Val Ile Gly Glu Pro Val Tyr Ile Ala Gly Asn Ser Leu Gly Gly
    210                 215                 220

Tyr Val Ala Leu Tyr Phe Ala Ala Thr His Pro His Leu Val Lys Gly
225                 230                 235                 240

Val Thr Leu Leu Asn Ala Thr Pro Phe Trp Gly Phe Pro Asn Pro
                245                 250                 255

Val Arg Ser Pro Lys Leu Ala Arg Leu Phe Pro Trp Pro Gly Ala Phe
            260                 265                 270

Pro Leu Pro Glu Arg Val Lys Lys Ile Thr Glu Leu Val Trp Gln Lys
        275                 280                 285

Ile Ser Asp Pro Glu Ser Ile Ala Glu Ile Leu Lys Gln Val Tyr Thr
    290                 295                 300

Asp His Ser Ile Asn Val Asp Lys Val Phe Ser Arg Ile Val Glu Val
305                 310                 315                 320
```

```
Thr Gln His Pro Ala Ala Ala Ser Phe Ala Ser Ile Met Leu Ala
            325                 330                 335

Pro Gly Gly Glu Leu Ser Phe Ser Glu Ala Leu Ser Arg Cys Lys Glu
        340                 345                 350

Asn Asn Val Gln Ile Cys Leu Met Tyr Gly Arg Glu Asp Pro Trp Val
        355                 360                 365

Arg Pro Leu Trp Gly Lys Lys Ile Lys Lys Glu Ile Pro Asn Ala Pro
    370                 375                 380

Tyr Tyr Glu Ile Ser Pro Ala Gly His Cys Pro His Asp Glu Val Pro
385                 390                 395                 400

Glu Val Val Asn Tyr Leu Met Arg Gly Trp Ile Lys His Leu Glu Ser
                405                 410                 415

Gly Gly Phe Glu Ala Leu Pro Leu Leu Glu Asp Thr Glu Glu Asp Trp
            420                 425                 430

Glu Glu Ser Arg Ile Gly Arg Glu Ile Glu Phe Pro Arg Asp Gly Trp
        435                 440                 445

Lys Lys Ala Val Asn Leu Trp Leu Tyr Gly Ser Asn Tyr Thr Tyr Trp
    450                 455                 460

Arg Gly Val Arg Glu Ser Phe Arg Ser Ser Phe Ile Arg Val Phe Gly
465                 470                 475                 480

Gly Lys Ser Ala

<210> SEQ ID NO 2
<211> LENGTH: 1853
<212> TYPE: DNA
<213> ORGANISM: Arabidopsis thaliana

<400> SEQUENCE: 2
aacccaattc ttctatttct tcttcacctt tagattttc  ctcgcttaat ttctcaataa    60
cgctctcaga gagaccattt gatgaagctt ctcgcttctg aatttgaaa  aggatttgat   120 aagacgagtt catagaagat taccgcaagt tcatcaactt tttgaacttg ttatggagat   180
aatctcactg aacgttgtgc cccagtgctc tgtggttact tggagtagta aattagcaac   240
gaaaagattg gtcccaaatc ggtcaagttt gttattctca ggggtcaaaa atccagact    300 tgtgattcga agtggaaatt ccgatggtta tgttgttggt gagaatgatg acttgggtcg   360
tatagccaga gaggagaat  caacgtcaaa ggttttgatt cctggtttgc ctgatgaatc   420
aaatggtgaa attgctgctc gaatcagtca ttctcactgc gagtggaagc ccaagcttag   480
agtacattat gagaaagccg ttgtgcacaa tctcgatgct cctgcggtgt tgtttcttcc   540
tggctttggc gttggttcat tcactatga  gaagcagctt accgatttgg gaagggatta   600
tcgagtatgg gctattgatt tcttggaca  gggtttatct ctccctactg aagatcctac   660
taccatgact gaagaaacca gttcctcgga agataaggaa ccattttggg gatttggtga   720
caaaactgaa ccgtgggctg atcaacttgt attctctctg gatctctgga gggatcaagt   780
tcagtatttt gtagaagagg ttatcggtga gcctgtgtac attgcaggga actcacttgg   840
agggtatgta gctctctact ttgcagcaac ccatcctcac ctggttaagg gtgttacctt   900
gcttaatgca acacctttct ggggtttctt ccctaatcca gtaagatccc caaagctagc   960
acgtctcttt ccatggcccg gagcattccc tctgccggaa agagtgaaaa aaatcacaga  1020
attggtgtgg caaaagataa gtgatcctga aagcatagct gagatactta acaggtcta   1080 cacagaccat tctatcaatg tggataaagt attctcacgt attgtggagg tcacacagca  1140
tccggctgct gcagcatcgt ttgcttcaat catgcttgct cctggtggag agctatcttt  1200
```

```
ctccgaagct ttatctaggt gtaaggaaaa caatgttcag atatgtctca tgtatggaag    1260
agaagatcca tgggtgagac cgttatgggg aaagaagata agaaggaaa tccccaacgc    1320 tccatactac gagatcagcc cagcgggtca ctgcccacac gatgaagtcc ctgaggtggt    1380
gaactatctg atgcgcgggt ggatcaagca cctggagtct ggtggttttg aagcgctccc    1440
gcttttggag acactgaag aagattggga ggagtccagg attggtagag aaattgagtt    1500
cccgagagat ggttggaaaa aagcagtgaa tctgtggtta tatgggtcaa actatacgta    1560
ctggagagga gttagagaat ctttcagatc cagtttata agggtgtttg agggaagtc    1620 tgcatagaag aagcatggaa cagtcgtcta gtgtaaatta attgtaatct atgttgcatc    1680
cgatgctagc tatataatgt tgtctgtaga atcaagtttc taaatgttc aaaaggaaaa    1740 gttagaaaaa tatctacttg atagttagtc acctaaatcg aaggaactcc tttcttgcat    1800
tgttgtatat aatccacagg ttcagattaa ataggaagg cgacattgca ggc            1853
```

<210> SEQ ID NO 3
<211> LENGTH: 1352
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(1344)

<400> SEQUENCE: 3

```
act agt gtc gcc gtc gag aag cgc agc ggc aac agc gac ggc tac gtc     48
Thr Ser Val Ala Val Glu Lys Arg Ser Gly Asn Ser Asp Gly Tyr Val
1               5                   10                  15 gtc ggc gag aac gac gac ctc ggc cgc att gcc cga cgc ggc gag agc     96
Val Gly Glu Asn Asp Asp Leu Gly Arg Ile Ala Arg Arg Gly Glu Ser
            20                  25                  30 acc agc aag gtc ctc atc ccc ggc ctc ccc gac gag agc aac ggc gag    144
Thr Ser Lys Val Leu Ile Pro Gly Leu Pro Asp Glu Ser Asn Gly Glu
        35                  40                  45 atc gcc gcc cgc atc agc cac agc cac tgc gag tgg aag ccc aag ctc    192
Ile Ala Ala Arg Ile Ser His Ser His Cys Glu Trp Lys Pro Lys Leu
    50                  55                  60 cgc gtc cac tac gag aag gcc ggc tgc gac aac ctc gac gcc cct gcc    240
Arg Val His Tyr Glu Lys Ala Gly Cys Asp Asn Leu Asp Ala Pro Ala
65                  70                  75                  80 gtc ctc ttc ctc ccc ggc ttc ggc gtc ggc agc ttt cac tac gag aag    288
Val Leu Phe Leu Pro Gly Phe Gly Val Gly Ser Phe His Tyr Glu Lys
                85                  90                  95 cag ctc acc gac ctg ggc cgc gac tac cgc gtc tgg gcc atc gac ttt    336
Gln Leu Thr Asp Leu Gly Arg Asp Tyr Arg Val Trp Ala Ile Asp Phe
            100                 105                 110 ctc ggc cag ggc ctc agc ctc ccc acc gag gac ccc acc acc atg acc    384
Leu Gly Gln Gly Leu Ser Leu Pro Thr Glu Asp Pro Thr Thr Met Thr
        115                 120                 125 gag gag acc agc agc agc gag gac aag gag ccc ttc tgg ggc ttc ggc    432
Glu Glu Thr Ser Ser Ser Glu Asp Lys Glu Pro Phe Trp Gly Phe Gly
    130                 135                 140 gac aag acc gag ccc tgg gcc gac cag ctc gtc ttt agc ctc gac ctc    480
Asp Lys Thr Glu Pro Trp Ala Asp Gln Leu Val Phe Ser Leu Asp Leu
145                 150                 155                 160 tgg cgc gac cag gtc cag tac ttc gtc gag gag gtc atc ggc gag ccc    528
Trp Arg Asp Gln Val Gln Tyr Phe Val Glu Glu Val Ile Gly Glu Pro
```

```
                              165                 170                 175
gtc tac att gcc ggc aac agc ctc ggc ggc tac gtc gcc ctc tac ttc        576
Val Tyr Ile Ala Gly Asn Ser Leu Gly Gly Tyr Val Ala Leu Tyr Phe
            180                 185                 190 gcc gcc acc cac ccc cac ctc gtc aag ggc gtc acc ctc ctc aac gcc        624
Ala Ala Thr His Pro His Leu Val Lys Gly Val Thr Leu Leu Asn Ala
            195                 200                 205 acc ccc ttt tgg ggc ttt ttc ccc aac ccc gtc cgc agc ccc aag ctc        672
Thr Pro Phe Trp Gly Phe Phe Pro Asn Pro Val Arg Ser Pro Lys Leu
210                 215                 220 gcc cgc ctc ttc cct tgg cct ggc gcc ttc ccg ctc ccc gag cgc gtc        720
Ala Arg Leu Phe Pro Trp Pro Gly Ala Phe Pro Leu Pro Glu Arg Val
225                 230                 235                 240 aag aag atc acc gag ctg gtc tgg cag aag atc agc gac ccc gag tcg        768
Lys Lys Ile Thr Glu Leu Val Trp Gln Lys Ile Ser Asp Pro Glu Ser
                245                 250                 255 atc gcc gag atc ctc aag cag gtc tac acc gac cac agc atc aac gtc        816
Ile Ala Glu Ile Leu Lys Gln Val Tyr Thr Asp His Ser Ile Asn Val
            260                 265                 270 gac aag gtc ttt agc cgc atc gtc gag gtc acc cag cac ccg gcc gcc        864
Asp Lys Val Phe Ser Arg Ile Val Glu Val Thr Gln His Pro Ala Ala
            275                 280                 285 gct gcc agc ttc gcc tcc atc atg ctg gcc cct ggc ggc gag ctg agc        912
Ala Ala Ser Phe Ala Ser Ile Met Leu Ala Pro Gly Gly Glu Leu Ser
290                 295                 300 ttc agc gag gcc ctc agc cgc tgc aag gag aac aac gtc cag atc tgc        960
Phe Ser Glu Ala Leu Ser Arg Cys Lys Glu Asn Asn Val Gln Ile Cys
305                 310                 315                 320 ctc atg tac ggc cgc gag gac ccc tgg gtc cgc ccc ctc tgg ggc aag       1008
Leu Met Tyr Gly Arg Glu Asp Pro Trp Val Arg Pro Leu Trp Gly Lys
                325                 330                 335 aag atc aag aag gag atc ccc aac gcc ccc tac tac gag atc agc cct       1056
Lys Ile Lys Lys Glu Ile Pro Asn Ala Pro Tyr Tyr Glu Ile Ser Pro
            340                 345                 350 gcc ggc cac tgc ccc cac gac gag gtc ccc gag gtc gtc aac tac ctc       1104
Ala Gly His Cys Pro His Asp Glu Val Pro Glu Val Val Asn Tyr Leu
            355                 360                 365 atg cgc ggc tgg atc aag cac ctg gag agc ggc ggc ttc gag gcc ctg       1152
Met Arg Gly Trp Ile Lys His Leu Glu Ser Gly Gly Phe Glu Ala Leu
370                 375                 380 ccc ctg ctc gag gac acc gag gag gac tgg gag gag agc cgc atc ggc       1200
Pro Leu Leu Glu Asp Thr Glu Glu Asp Trp Glu Glu Ser Arg Ile Gly
385                 390                 395                 400 cgc gag atc gag ttc ccc cgc gac ggc tgg aag aag gcc gtc aac ctc       1248
Arg Glu Ile Glu Phe Pro Arg Asp Gly Trp Lys Lys Ala Val Asn Leu
                405                 410                 415 tgg ctc tac ggc agc aac tac acc tac tgg cgc ggc gtc cgc gag agc       1296
Trp Leu Tyr Gly Ser Asn Tyr Thr Tyr Trp Arg Gly Val Arg Glu Ser
            420                 425                 430 ttc cgc agc agc ttc atc cgc gtc ttt ggc ggc aag agc gcc taa tag       1344
Phe Arg Ser Ser Phe Ile Arg Val Phe Gly Gly Lys Ser Ala
            435                 440                 445 ggcgcgcc                                                               1352

<210> SEQ ID NO 4
<211> LENGTH: 446
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 4

```
Thr Ser Val Ala Val Glu Lys Arg Ser Gly Asn Ser Asp Gly Tyr Val
1               5                   10                  15

Val Gly Glu Asn Asp Asp Leu Gly Arg Ile Ala Arg Gly Glu Ser
            20                  25                  30

Thr Ser Lys Val Leu Ile Pro Gly Leu Pro Asp Glu Ser Asn Gly Glu
        35                  40                  45

Ile Ala Ala Arg Ile Ser His Ser His Cys Glu Trp Lys Pro Lys Leu
    50                  55                  60

Arg Val His Tyr Glu Lys Ala Gly Cys Asp Asn Leu Asp Ala Pro Ala
65                  70                  75                  80

Val Leu Phe Leu Pro Gly Phe Gly Val Gly Ser Phe His Tyr Glu Lys
                85                  90                  95

Gln Leu Thr Asp Leu Gly Arg Asp Tyr Arg Val Trp Ala Ile Asp Phe
            100                 105                 110

Leu Gly Gln Gly Leu Ser Leu Pro Thr Glu Asp Pro Thr Thr Met Thr
        115                 120                 125

Glu Glu Thr Ser Ser Glu Asp Lys Glu Pro Phe Trp Gly Phe Gly
130                 135                 140

Asp Lys Thr Glu Pro Trp Ala Asp Gln Leu Val Phe Ser Leu Asp Leu
145                 150                 155                 160

Trp Arg Asp Gln Val Gln Tyr Phe Val Glu Glu Val Ile Gly Glu Pro
                165                 170                 175

Val Tyr Ile Ala Gly Asn Ser Leu Gly Gly Tyr Val Ala Leu Tyr Phe
            180                 185                 190

Ala Ala Thr His Pro His Leu Val Lys Gly Val Thr Leu Leu Asn Ala
        195                 200                 205

Thr Pro Phe Trp Gly Phe Phe Pro Asn Pro Val Arg Ser Pro Lys Leu
    210                 215                 220

Ala Arg Leu Phe Pro Trp Pro Gly Ala Phe Pro Leu Pro Glu Arg Val
225                 230                 235                 240

Lys Lys Ile Thr Glu Leu Val Trp Gln Lys Ile Ser Asp Pro Glu Ser
                245                 250                 255

Ile Ala Glu Ile Leu Lys Gln Val Tyr Thr Asp His Ser Ile Asn Val
            260                 265                 270

Asp Lys Val Phe Ser Arg Ile Val Glu Val Thr Gln His Pro Ala Ala
        275                 280                 285

Ala Ala Ser Phe Ala Ser Ile Met Leu Ala Pro Gly Gly Glu Leu Ser
    290                 295                 300

Phe Ser Glu Ala Leu Ser Arg Cys Lys Glu Asn Asn Val Gln Ile Cys
305                 310                 315                 320

Leu Met Tyr Gly Arg Glu Asp Pro Trp Val Arg Pro Leu Trp Gly Lys
                325                 330                 335

Lys Ile Lys Lys Glu Ile Pro Asn Ala Pro Tyr Tyr Glu Ile Ser Pro
            340                 345                 350

Ala Gly His Cys Pro His Asp Glu Val Pro Glu Val Val Asn Tyr Leu
        355                 360                 365

Met Arg Gly Trp Ile Lys His Leu Glu Ser Gly Gly Phe Glu Ala Leu
    370                 375                 380

Pro Leu Leu Glu Asp Thr Glu Glu Asp Trp Glu Glu Ser Arg Ile Gly
385                 390                 395                 400
```

```
Arg Glu Ile Glu Phe Pro Arg Asp Gly Trp Lys Lys Ala Val Asn Leu
                405                 410                 415

Trp Leu Tyr Gly Ser Asn Tyr Thr Tyr Trp Arg Gly Val Arg Glu Ser
            420                 425                 430

Phe Arg Ser Ser Phe Ile Arg Val Phe Gly Gly Lys Ser Ala
        435                 440                 445

<210> SEQ ID NO 5
<211> LENGTH: 566
<212> TYPE: PRT
<213> ORGANISM: Populus trichocarpa

<400> SEQUENCE: 5

Met Met Ile Leu Ala Phe Phe Leu Ile Phe Met Glu Phe Tyr Phe Gln
1               5                   10                  15

Leu Arg Arg Arg Tyr Ala Ser Tyr Leu Leu Ile Asn Met Ile Leu Leu
            20                  25                  30

Ile Thr Ala Asp Gln Pro Phe Trp Gly Met Glu Ile Leu Thr Ser Ser
        35                  40                  45

Thr Ala Ser Cys Cys Leu Val Val Asn Leu Arg Trp Lys Leu Ala Glu
    50                  55                  60

Asn Gly Ser Asn Ser Ser Gln Leu Lys Leu Pro Thr Ser Arg Glu Arg
65                  70                  75                  80

Lys Ile Leu Phe Ala Arg Thr Asn Gln Arg Asn Gly Ser Leu Arg Phe
                85                  90                  95

Ser Ser Val Asp Lys Phe Leu Lys Lys Leu Asn His Gly Lys Gly Ser
            100                 105                 110

Arg Ser Leu Asp Ser Phe Gly Gly Leu Lys Asn Gly Asn Ser Lys Val
        115                 120                 125

Phe Ser Gly Asn Ser Ser Tyr Val Val Gly Gly Glu Asp Asp Val
    130                 135                 140

Gly Ser Ile Thr Glu Asn Gly Glu Ser Pro Thr Lys Val Leu Ile Pro
145                 150                 155                 160

Gly Leu Pro Asp Glu Ser Asn Gly Glu Tyr Ser Ala Pro Val Ser Ser
                165                 170                 175

Cys Phe Trp Lys Trp Lys Pro Lys Leu Asn Val His Tyr Glu Lys Ala
            180                 185                 190

Gly Cys Glu Asn Val Asn Ser Pro Pro Val Leu Phe Leu Pro Gly Phe
        195                 200                 205

Gly Val Gly Ser Phe His Tyr Glu Lys Gln Leu Lys Asp Leu Gly Arg
    210                 215                 220

Asp Tyr Arg Val Trp Ala Ile Asp Phe Leu Gly Gln Gly Met Ser Leu
225                 230                 235                 240

Pro Val Glu Asn Pro Thr Leu Phe Ser Lys Asp Gly Ala Ala Ser Glu
                245                 250                 255

Gly Lys Asp Ser Ile Trp Gly Phe Gly Asp Glu Ile Glu Pro Trp Ala
            260                 265                 270

Asn Asp Leu Val Phe Ser Met Asp Leu Trp Gln Asp Gln Val His Asn
        275                 280                 285

Phe Ile Glu Glu Val Ile Gly Glu Pro Val Tyr Ile Val Gly Asn Ser
    290                 295                 300

Leu Gly Gly Phe Val Ala Leu Tyr Phe Ala Ala Arg Tyr Pro His Leu
305                 310                 315                 320

Val Lys Gly Val Thr Leu Leu Asn Ala Thr Pro Phe Trp Gly Phe Leu
                325                 330                 335
```

```
Pro Asn Pro Ile Arg Ser Pro Arg Leu Ala Arg Ile Phe Pro Trp Ser
            340                 345                 350

Gly Thr Phe Pro Leu Pro Ala Asn Val Arg Lys Leu Ile Ala Phe Phe
        355                 360                 365

Trp Gln Lys Ile Ser Asp Pro Lys Ser Ile Ala Glu Ile Leu Lys Gln
370                 375                 380

Val Tyr Thr Asp His Ser Thr Asn Ile Asp Lys Val Phe Ser Arg Ile
385                 390                 395                 400

Leu Glu Ile Thr Gln His Pro Ala Ala Ala Ser Phe Ala Ser Ile
                405                 410                 415

Met Phe Ala Pro Gln Gly Gln Leu Ser Phe Arg Glu Thr Leu Ala Arg
            420                 425                 430

Cys Lys Met Ser Asp Thr Pro Ile Cys Leu Val Tyr Gly Lys Glu Asp
            435                 440                 445

Pro Trp Val Lys Pro Val Trp Gly Leu Gln Val Lys Gln Gln Val Pro
        450                 455                 460

Glu Ala Pro Tyr Tyr Glu Ile Ser Pro Ala Gly His Cys Pro His Asp
465                 470                 475                 480

Glu Val Pro Glu Ala Val Asn Tyr Leu Leu Arg Gly Trp Ile Lys Asn
                485                 490                 495

Leu Glu Ser His Gly Ser Val Ala Leu Pro Leu His Glu Asp Ala Glu
            500                 505                 510

Val Val Glu Asn Ser Phe Ala Met Asp Leu Glu Phe Val Arg Glu Gly
            515                 520                 525

Ser Arg Lys Ser Val Ile Val Arg Phe Phe Gly Ser Arg Phe Ser Ile
        530                 535                 540

Trp Asn Ser Phe Ser Ser Tyr Ile Lys Ser Gln Phe Lys Glu Thr Thr
545                 550                 555                 560

Ser Arg Ile Leu Thr Pro
                565

<210> SEQ ID NO 6
<211> LENGTH: 524
<212> TYPE: PRT
<213> ORGANISM: Vitis vinifera

<400> SEQUENCE: 6

Met Glu Ile Leu Ser Cys His Ser Ala Pro Cys Cys Lys Leu Val Asn
1               5                   10                  15

Leu Gly Gly Thr Ser Val His Lys Ser Ser Gly Ser Ser Gln Ala Lys
            20                  25                  30

Leu Pro Gly Ser Arg Asn Asn Arg Ile Leu Cys Ala Arg Ile Gly Ser
        35                  40                  45

Lys Leu Gly Ser Ser Gly Tyr Ser Asn Leu Asp Asp Phe Cys Thr Lys
50                  55                  60

Asn Phe Gly Arg His Glu Gly Ser Arg Ser Leu Thr Ala Phe Lys Gly
65                  70                  75                  80

Ser Ala Asn Val Asn Ser Lys Ala Leu Ser Glu Ser Tyr Asn Gly Tyr
                85                  90                  95

Val Ile Asp Gly Lys Glu Gly Val Gly Asp Ile Ser Glu Arg Gly Asp
            100                 105                 110

Leu Ile Thr Gln Ile Leu Ile Pro Gly Leu Pro Asp Asp Ser Asn Asp
        115                 120                 125

Asp Ser Gly Ala Gln Ile Ser Ser Cys Phe Trp Glu Trp Lys Pro Lys
```

```
                130             135             140
Leu Thr Val His Tyr Glu Lys Ser Gly Cys Glu Asn Val Asn Ser Pro
145                 150                 155                 160

Pro Val Leu Phe Leu Pro Gly Phe Gly Val Gly Ser Phe His Tyr Glu
                165                 170                 175

Lys Gln Leu Lys Asp Leu Gly Arg Asp Phe Arg Val Trp Ala Val Asp
            180                 185                 190

Phe Leu Gly Gln Gly Met Ser Leu Pro Phe Glu Asp Pro Ala Pro Gln
        195                 200                 205

Ser Lys Lys Glu Leu Asp Ser Glu Arg Asn Asp Phe Ser Trp Gly Phe
210                 215                 220

Gly Asp Glu Thr Glu Pro Trp Ala Asn Glu Leu Val Tyr Ser Ile Asp
225                 230                 235                 240

Leu Trp Gln Asp Gln Val Arg Tyr Phe Ile Glu Gln Val Ile Gly Glu
                245                 250                 255

Pro Val Tyr Ile Val Gly Asn Ser Leu Gly Gly Phe Val Ala Leu Tyr
                260                 265                 270

Phe Ala Ala Cys Asn Pro Gln Leu Val Lys Gly Val Thr Leu Leu Asn
            275                 280                 285

Ala Thr Pro Phe Trp Gly Phe Leu Pro Asn Pro Ser Arg Ser Pro Ser
        290                 295                 300

Leu Ala Arg Ile Phe Pro Trp Ala Gly Thr Phe Pro Leu Pro Ala Phe
305                 310                 315                 320

Val Arg Lys Leu Thr Glu Phe Val Trp Gln Lys Ile Ser Asp Pro Arg
                325                 330                 335

Ser Ile Gly Glu Val Leu Lys Gln Val Tyr Ala Asp His Ser Thr Lys
                340                 345                 350

Val Asp Lys Val Phe Ser Arg Ile Leu Glu Thr Thr Gln His Pro Ala
            355                 360                 365

Ala Ala Ala Ser Phe Ala Ser Ile Met Phe Ala Pro Gln Gly Gln Leu
        370                 375                 380

Ser Phe Ser Glu Ala Leu Ser Arg Cys Gln Met Ser Asn Val Pro Ile
385                 390                 395                 400

Cys Leu Met Tyr Gly Lys Glu Asp Pro Trp Val Arg Pro Val Trp Gly
                405                 410                 415

Leu Gln Val Lys Arg Gln Leu Leu Glu Ala Pro Tyr Tyr Glu Ile Ser
                420                 425                 430

Pro Ala Gly His Cys Pro His Asp Glu Val Pro Glu Val Val Asn Tyr
            435                 440                 445

Leu Leu Arg Gly Trp Ile Gly Asn Leu Glu Ser Lys Gly Ser Val Thr
        450                 455                 460

Leu Pro Leu Leu Asp Asp Pro Glu Asn Ile Gln Tyr Gly Thr Thr Lys
465                 470                 475                 480

Asp Leu Glu Phe Val Arg Glu Gly Ser Lys Lys Ser Val Arg Val His
                485                 490                 495

Phe Tyr Gly Ser Arg Phe Ser Leu Trp Asn Arg Ile Arg Ser Tyr Val
                500                 505                 510

Lys Ser Arg Phe Glu Ala Leu Glu Ile Asn Ser Arg
            515                 520

<210> SEQ ID NO 7
<211> LENGTH: 481
<212> TYPE: PRT
<213> ORGANISM: Ricinus communis
```

<400> SEQUENCE: 7

Met Phe Ser Pro Cys Pro Leu Ile Ser Ser Gly Gln Thr Gln Trp Leu
1               5                   10                  15

Asp Leu Gly Met Asp Ile Leu Thr Phe Asn Val Thr Thr Ser His Arg
            20                  25                  30

Thr Ala His Phe Gly Ser Lys Leu Val Asp Lys Thr Lys Tyr Ser Cys
        35                  40                  45

Lys Ser Lys Val Ser Thr Ile Ile Lys Pro Gln Val Phe Cys Ala Arg
    50                  55                  60

Ile Asp Gln Ser Cys Gly Leu Leu Arg Phe Ser Ser Asn Lys Phe
65                  70                  75                  80

Leu Asp Tyr Pro Lys Lys Ile Glu Val Ser Lys His Asn Ala Leu
                85                  90                  95

Lys Gly Ile Lys Val Val Asn Ser Lys Val Leu Ser Gly Asn Tyr Asn
            100                 105                 110

Gly Tyr Val Ile Glu Ala Asp Glu Asp Met Glu Ser Val Ser Gly Ser
        115                 120                 125

Gly Glu Ser Thr Pro Glu Ile Leu Ile Pro Gly Leu Pro Asn Glu Ser
130                 135                 140

Ser Gly Glu Cys Gly Ala Pro Ile Asn Ser Cys Phe Trp Glu Trp Lys
145                 150                 155                 160

Pro Lys Leu Tyr Val His Tyr Glu Lys Ala Gly Cys Glu Asn Val Lys
                165                 170                 175

Ser Pro Pro Val Leu Phe Leu Pro Gly Phe Gly Val Gly Ser Phe His
            180                 185                 190

Phe Glu Asn Gln Leu Lys Asp Leu Gly Arg Asp Tyr Arg Val Trp Ala
        195                 200                 205

Ile Asp Phe Leu Gly Gln Gly Met Ser Leu Pro Val Glu Asn Pro Thr
    210                 215                 220

Leu Gln Leu Arg Glu Gly Asp Ile Leu Glu Gly Lys Asn Ser Phe Trp
225                 230                 235                 240

Gly Phe Gly Asp Glu Thr Glu Pro Trp Ala Asn Glu Leu Val Tyr Ser
                245                 250                 255

Met Asp Leu Trp Arg Asp Gln Val Arg Tyr Phe Ile Glu Glu Val Ile
            260                 265                 270

Gly Glu Pro Val Tyr Val Gly Asn Ser Leu Gly Gly Phe Val Ala
        275                 280                 285

Ile Tyr Phe Ala Ala Ser Asn Pro Gln Leu Val Lys Gly Val Thr Leu
    290                 295                 300

Leu Asn Ala Thr Pro Phe Trp Gly Phe Leu Pro Asn Pro Ile Arg Ser
305                 310                 315                 320

Pro Arg Leu Ala Arg Ile Ile Pro Trp Ser Gly Thr Phe Pro Leu Pro
                325                 330                 335

Ala Ser Val Arg Lys Leu Thr Glu Phe Phe Trp Gln Lys Ile Ser Asp
            340                 345                 350

Pro Lys Ser Ile Ala Gln Val Leu Lys Gln Val Tyr Ala Asp His Ser
        355                 360                 365

Thr Asn Val Asp Gln Val Phe Ser Arg Ile Leu Lys Ile Thr Gln His
    370                 375                 380

Pro Ala Ala Ala Ala Ser Phe Ala Ser Ile Met Phe Ala Pro Gln Gly
385                 390                 395                 400

Gln Leu Ser Phe Arg Glu Cys Leu Met Arg Cys Lys Met Asn Asn Leu

-continued

```
                405                 410                 415
Pro Ile Cys Leu Leu Tyr Gly Arg Glu Asp Pro Trp Val Lys Pro Ile
            420                 425                 430
Trp Gly Leu Gln Val Lys Arg Gln Val Pro Glu Ala Ser Tyr Tyr Glu
            435                 440                 445
Ile Ser Pro Ala Gly His Cys Pro His Asp Glu Val Pro Glu Val Cys
            450                 455                 460
Ser Leu Ser Leu Phe Leu Val Gly Ile Pro Leu Leu Phe Leu Val Ile
465                 470                 475                 480
Leu

<210> SEQ ID NO 8
<211> LENGTH: 486
<212> TYPE: PRT
<213> ORGANISM: Oryza sativa

<400> SEQUENCE: 8

Met Glu Val Val Ser Ser His Ser Cys Leu Ala Phe Asn Arg Thr
1               5                   10                  15
Pro Ser Ser Ala Trp Arg Phe Pro Gly Asn Gly Leu Gly Pro Gly His
            20                  25                  30
Ala Lys Leu Thr Arg Pro Arg Ser Ala Ile Leu Cys Val Arg Ser Gly
        35                  40                  45
Thr Ala Ser Asn Pro Ala Asp Ser Gly Lys Val His Ala Ser His Gly
    50                  55                  60
Phe Tyr Val Ser Asp Val Asp Ala Ala Leu Gln Gly Ile Pro Lys Lys
65                  70                  75                  80
Val Gly Glu Ile Glu Lys Met Ile Ile Pro Ser Leu Pro Glu Gly Pro
                85                  90                  95
Glu Ser Ser Leu Ile Ser Thr Gly Phe Trp Glu Trp Lys Pro Lys Leu
            100                 105                 110
Ser Val Tyr Tyr Glu Lys Ser Gly Ile Asp Asn Ser Lys Ala Pro Ser
        115                 120                 125
Val Leu Phe Leu Pro Gly Phe Gly Val Gly Thr Phe His Phe Glu Lys
    130                 135                 140
Gln Leu Lys Asp Leu Gly Arg Asp Tyr Lys Val Trp Thr Met Asp Phe
145                 150                 155                 160
Leu Gly Gln Gly Met Ser Leu Pro Cys Glu Asp Pro Ala Pro Lys Ser
                165                 170                 175
Thr Ser Gly Glu Leu Asp Glu Asp Thr Tyr Trp Gly Phe Gly Gln Glu
            180                 185                 190
Leu Gln Pro Trp Ala Glu Glu Leu Val Tyr Ser Ile Asp Leu Trp Arg
        195                 200                 205
Asp Gln Val Gln His Phe Ile Glu Glu Val Ile Gly Glu Pro Val Tyr
    210                 215                 220
Ile Val Gly Asn Ser Leu Gly Gly Phe Val Ser Leu Tyr Leu Ala Ala
225                 230                 235                 240
Ser Cys Pro His Leu Val Lys Gly Val Thr Leu Leu Asn Ala Thr Pro
                245                 250                 255
Phe Trp Gly Phe Leu Pro Asn Pro Ala Thr Ser Pro Arg Leu Ser Lys
            260                 265                 270
Ile Phe Pro Trp Ala Gly Thr Phe Pro Leu Pro Ser Phe Val Arg Lys
        275                 280                 285
Leu Thr Glu Thr Val Trp Gln Lys Ile Ser Asp Pro Arg Ser Ile Gln
```

```
                290                 295                 300
Gly Ile Leu Lys Gln Val Tyr Ala Asp His Ser Thr Asn Val Asp Met
305                 310                 315                 320

Val Phe Ser Arg Ile Ile Glu Thr Thr Gln His Pro Ala Ala Ala Ala
                325                 330                 335

Ser Phe Ala Ser Ile Met Cys Ala Pro Lys Gly Gln Ile Ser Phe Glu
                340                 345                 350

Glu Ala Leu Ser Arg Cys Gln Arg Gln Gly Ile Pro Ile Ser Leu Met
                355                 360                 365

Tyr Gly Arg Glu Asp Pro Trp Val Arg Pro Ile Trp Gly Ile Lys Val
                370                 375                 380

Lys Gln Gln Val Pro Glu Ser Pro Tyr Tyr Glu Ile Ser Pro Ala Gly
385                 390                 395                 400

His Cys Pro His Asp Glu Val Pro Glu Val Ile Asn Tyr Leu Leu Arg
                405                 410                 415

Gly Trp Leu Lys Asn Val Glu Ser Glu Gly Ser Val Ala Val Pro Phe
                420                 425                 430

Leu Glu Glu Pro Ser Tyr Ala Glu Asn Gly Val Ser Arg Glu Leu Glu
                435                 440                 445

Phe Val Arg Gly Gly Ser Lys Lys Ser Val His Val Arg Leu Phe Gly
                450                 455                 460

Ser Lys Ile Ser Leu Trp Ser Gln Leu Arg Ser Leu Leu Lys Ser Asn
465                 470                 475                 480

Thr Trp Val Ile Ser Arg
                485

<210> SEQ ID NO 9
<211> LENGTH: 491
<212> TYPE: PRT
<213> ORGANISM: Zea mays

<400> SEQUENCE: 9

Met Glu Val Val Ser Cys Ser His Ser Cys Ser Ala Leu His Gln Thr
1               5                   10                  15

Pro Ala Ser Thr Trp Arg Leu Arg Gly Ser Ala Leu Gly Leu Gly Leu
                20                  25                  30

Gly His Ala Arg Pro Ser Arg Thr Arg Arg Tyr Thr Val Ala Cys Val
                35                  40                  45

Gly Thr Thr Ser Gly Ala Ser Asn Pro Gly Gly Ser Gly Lys Val His
                50                  55                  60

Ala Ala Gln Gly Phe His Val Ser Asp Val Asp Ala Ala Leu Gln Gly
65              70                  75                  80

Ile Pro Ser Met Lys Ala Gly Glu Ala Glu Arg Val Met Ile Gln Gly
                85                  90                  95

Leu Pro Glu Gly Pro Asp Ser Ser Pro Ile Ser Thr Gly Phe Trp Glu
                100                 105                 110

Trp Lys Pro Lys Leu Thr Val His Tyr Glu Arg Ser Gly Met Lys Asn
                115                 120                 125

Ser Lys Ala Pro Ala Val Leu Phe Leu Pro Gly Phe Gly Val Gly Thr
                130                 135                 140

Phe His Phe Glu Lys Gln Leu Arg Asp Leu Gly Arg Asp His Arg Val
145                 150                 155                 160

Trp Thr Met Asp Phe Leu Gly Gln Gly Met Ser Leu Pro Gly Glu Asp
                165                 170                 175
```

-continued

Pro Ala Pro Ser Ser Ile Ala Ser Glu Asp Ala Phe Trp Gly Phe Gly
            180                 185                 190

Gln Asp Ser Gln Pro Trp Ala Glu Glu Leu Val Tyr Ser Val Asp Leu
        195                 200                 205

Trp Gln Asn Gln Val Gln His Phe Ile Glu Glu Val Ile Arg Glu Pro
    210                 215                 220

Val Tyr Ile Val Gly Asn Ser Leu Gly Gly Phe Val Ala Leu Tyr Phe
225                 230                 235                 240

Ala Ala Ser Ser Pro His Leu Val Lys Gly Val Thr Leu Leu Asn Ala
                245                 250                 255

Thr Pro Phe Trp Gly Phe Phe Pro Asn Pro Ala Thr Ser Pro Arg Leu
            260                 265                 270

Ser Lys Ile Phe Pro Trp Ala Gly Thr Phe Pro Leu Pro Ser Phe Val
        275                 280                 285

Arg Lys Ile Thr Glu Ala Val Trp Gln Lys Ile Ser Asp Pro Lys Ser
    290                 295                 300

Ile Gln Asp Ile Leu Lys Gln Val Tyr Ala Asp His Ser Thr Asn Val
305                 310                 315                 320

Asp Lys Val Phe Ser Arg Ile Val Glu Ile Thr Gln His Pro Ala Ala
                325                 330                 335

Ala Ala Ser Phe Ala Ser Ile Met Phe Ala Pro Arg Gly Gln Ile Ser
            340                 345                 350

Phe Gln Glu Ala Ile Ser Arg Cys Gln Asp Gln Gly Ile Pro Ile Ser
        355                 360                 365

Leu Met Tyr Gly Arg Glu Asp Pro Trp Ile Arg Pro Ile Trp Gly Leu
    370                 375                 380

Lys Val Lys Gln Gln Val Pro Glu Ala Pro Tyr Tyr Glu Ile Ser Pro
385                 390                 395                 400

Ala Gly His Cys Pro His Asp Glu Val Pro Glu Val Ile Asn Tyr Leu
                405                 410                 415

Leu Arg Gly Trp Leu Lys Asn Leu Glu Ser Gly Ser Val Asp Leu
            420                 425                 430

Pro Phe Leu Glu Glu Arg Ser Tyr Ala Glu Arg Gly Val Ser Arg Glu
        435                 440                 445

Leu Glu Phe Val Arg Glu Gly Ser Arg Lys Ser Val Ser Val Arg Leu
    450                 455                 460

Tyr Gly Thr Lys Ile Ser Leu Trp Ser Gln Leu Ser Ser Phe Leu Asn
465                 470                 475                 480

Thr Arg Val Pro Lys Ser Arg Ile Val Leu Arg
                485                 490

<210> SEQ ID NO 10
<211> LENGTH: 505
<212> TYPE: PRT
<213> ORGANISM: Nicotiana tabacum

<400> SEQUENCE: 10

Met Glu Val His Ser Cys Tyr Ser Thr Thr Tyr Tyr Cys Ile Val Asn
1               5                   10                  15

Val Ser Lys Cys Leu Ile Ser Asn Gln Ala Lys Phe Pro Ile Val Lys
            20                  25                  30

Glu Arg Arg Leu Tyr Ser Gly Leu Asp Val Tyr Ser Ile Lys Lys Lys
        35                  40                  45

Arg Thr Gln Arg Leu Thr Ile Thr Ala Leu Lys Gly Phe Asp Ser Val
    50                  55                  60

```
Asp Ser Ser Leu Leu Ser Glu Ser Tyr Asn Ser Asp Ile Ile Asp Gly
 65                  70                  75                  80

Lys Val Gly Thr Gln Asp Val Ile Gly Ser Ala Lys Ser Val Pro Lys
                 85                  90                  95

Val Ile Val Pro Ser Leu Pro Asp Glu Thr Lys Ala Asp Ser Val Ala
            100                 105                 110

Val Val Asp Ser Cys Leu Trp Glu Trp Lys Pro Lys Leu Lys Val His
            115                 120                 125

Tyr Glu Lys Ser Gly Cys Gln Asn Val Asn Ser Ala Pro Ile Leu Phe
            130                 135                 140

Leu Pro Gly Phe Gly Val Gly Ser Phe His Tyr Glu Lys Gln Leu Lys
145                 150                 155                 160

Asp Leu Gly Cys Asp His Arg Ile Trp Ala Leu Asp Phe Leu Gly Gln
                165                 170                 175

Gly Lys Ser Leu Pro Cys Glu Asp Pro Thr Leu Gln Ser Lys Arg Leu
            180                 185                 190

Asp Glu Ser Glu Arg Asp Gly Asn Asn Ala Val Trp Gly Phe Gly Asp
            195                 200                 205

Glu Ala Glu Pro Trp Ala Lys Glu Leu Val Tyr Ser Val Asp Leu Trp
210                 215                 220

Arg Asp Gln Val Arg Tyr Phe Ile Glu Glu Val Ile Lys Glu Pro Val
225                 230                 235                 240

Tyr Ile Val Gly Asn Ser Leu Gly Gly Tyr Val Ala Leu Tyr Leu Ala
                245                 250                 255

Ala Tyr Tyr Pro Gln Leu Val Lys Gly Val Thr Leu Leu Asn Ala Thr
                260                 265                 270

Pro Phe Trp Gly Phe Leu Pro Asn Pro Val Arg Ser Pro Arg Leu Ser
            275                 280                 285

Arg Leu Phe Pro Trp Ala Gly Thr Phe Pro Leu Pro Asp Thr Ile Arg
290                 295                 300

Lys Leu Thr Glu Leu Val Trp Gln Lys Ile Ser Ala Pro Glu Ser Ile
305                 310                 315                 320

Ala Glu Val Leu Lys Gln Val Tyr Ala Asp His Thr Thr Lys Val Asp
                325                 330                 335

Lys Val Phe Ser Ser Ile Leu Gly Val Thr Glu His Pro Ala Ala Ala
            340                 345                 350

Ala Ser Leu Ala Ser Ile Leu Phe Ala Pro Arg Gly Gln Leu Ser Phe
            355                 360                 365

Lys Glu Ala Leu Thr Gly Cys Arg Met Asn Asn Val Pro Val Cys Leu
            370                 375                 380

Met Tyr Gly Lys Glu Asp Pro Trp Val Met Pro Phe Trp Ala Leu Gln
385                 390                 395                 400

Val Lys Arg Gln Leu Pro Glu Ala Pro Tyr Tyr Gln Ile Ser Pro Ala
                405                 410                 415

Gly His Cys Pro His Asp Glu Val Pro Glu Ile Val Asn Phe Leu Leu
                420                 425                 430

Arg Gly Trp Ile Lys Asn Ile Glu Ser His Ser Ser Val Ala Leu Pro
            435                 440                 445

Leu Leu Asp Ser Pro Glu Ser Ile Glu Tyr Asp Ile Val Arg Asp Leu
            450                 455                 460

Glu Phe Val Arg Gln Gly Met Lys Lys Ser Val Arg Val Gln Phe Tyr
465                 470                 475                 480
```

```
Gly Ser Met Thr Ser Gln Trp Glu Lys Leu Gly Met Phe Leu Lys Ser
                485                 490                 495

Arg Phe Gln Tyr Gly Val Tyr Ser Pro
                500             505

<210> SEQ ID NO 11
<211> LENGTH: 426
<212> TYPE: PRT
<213> ORGANISM: Oryza sativa

<400> SEQUENCE: 11

Met Glu Val Val Ser Ser His Ser Cys Leu Ala Phe Asn Arg Thr
1               5                   10                  15

Pro Ser Ser Ala Trp Arg Phe Pro Gly Asn Gly Leu Gly Pro Gly His
                20                  25                  30

Ala Lys Leu Thr Arg Pro Arg Ser Ala Ile Leu Cys Val Arg Ser Gly
                35                  40                  45

Thr Ala Ser Asn Pro Ala Asp Ser Gly Lys Val His Ala Ser His Gly
        50                  55                  60

Phe Tyr Val Ser Asp Val Asp Ala Ala Leu Gln Gly Ile Pro Lys Lys
65                  70                  75                  80

Val Gly Glu Ile Glu Lys Met Ile Ile Pro Ser Leu Pro Glu Gly Pro
                85                  90                  95

Glu Ser Ser Leu Ile Ser Thr Gly Phe Trp Glu Trp Lys Pro Lys Leu
                100                 105                 110

Ser Val Tyr Tyr Glu Lys Ser Gly Ile Asp Asn Ser Lys Ala Pro Ser
                115                 120                 125

Val Leu Phe Leu Pro Gly Phe Gly Val Gly Thr Phe His Phe Glu Lys
        130                 135                 140

Gln Leu Lys Asp Leu Gly Arg Asp Tyr Lys Val Trp Thr Met Asp Phe
145                 150                 155                 160

Leu Gly Gln Gly Met Ser Leu Pro Cys Glu Asp Pro Ala Pro Lys Ser
                165                 170                 175

Thr Ser Gly Glu Leu Asp Glu Asp Thr Tyr Trp Gly Phe Gly Gln Glu
                180                 185                 190

Leu Gln Pro Trp Ala Glu Glu Leu Val Tyr Ser Ile Asp Leu Trp Arg
                195                 200                 205

Asp Gln Val Gln His Phe Ile Glu Glu Val Ile Gly Glu Pro Val Tyr
        210                 215                 220

Ile Val Gly Asn Ser Leu Gly Gly Phe Val Ser Leu Tyr Leu Ala Ala
225                 230                 235                 240

Ser Cys Pro His Leu Val Lys Gly Val Thr Leu Leu Asn Ala Thr Pro
                245                 250                 255

Phe Trp Gly Phe Leu Pro Asn Pro Ala Thr Ser Pro Arg Leu Ser Lys
                260                 265                 270

Ile Phe Pro Trp Ala Gly Thr Phe Pro Leu Pro Ser Phe Val Arg Lys
                275                 280                 285

Leu Thr Glu Thr Val Trp Gln Lys Ile Ser Asp Pro Arg Ser Ile Gln
        290                 295                 300

Gly Ile Leu Lys Gln Val Tyr Ala Asp His Ser Thr Asn Val Asp Met
305                 310                 315                 320

Val Phe Ser Arg Ile Ile Glu Thr Thr Gln His Pro Ala Ala Ala Ala
                325                 330                 335

Ser Phe Ala Ser Ile Met Cys Ala Pro Lys Gly Gln Ile Ser Phe Glu
                340                 345                 350
```

```
Glu Ala Leu Ser Arg Cys Gln Arg Gln Gly Ile Pro Ile Ser Leu Met
            355                 360                 365

Tyr Gly Arg Glu Asp Pro Trp Val Arg Pro Ile Trp Gly Ile Lys Val
        370                 375                 380

Lys Gln Gln Val Pro Glu Ser Pro Tyr Glu Ile Ser Pro Ala Gly
385                 390                 395                 400

His Cys Pro His Asp Glu Val Pro Glu Val Pro Gly Lys Ser Leu Ala
                405                 410                 415

Trp Trp Ile Thr Gly Arg Leu Gln Ala Ser
            420                 425

<210> SEQ ID NO 12
<211> LENGTH: 337
<212> TYPE: PRT
<213> ORGANISM: Physcomitrella patens
<220> FEATURE:
<223> OTHER INFORMATION: subsp. patens

<400> SEQUENCE: 12

Ile Ala Ser His Ile Trp Glu Trp Arg His Arg Trp Asn Ile His Tyr
1               5                   10                  15

Glu Cys Ala Gly Thr Ser Leu Asn Thr Asn Ala Pro Ala Met Leu Leu
            20                  25                  30

Leu Pro Gly Phe Gly Val Gly Ser Phe His Tyr His Gln Gln Leu Arg
        35                  40                  45

Asp Leu Gly Gln Glu Tyr Arg Val Trp Ala Ile Asp Phe Leu Gly Gln
    50                  55                  60

Gly Lys Ser Trp Pro Ser His Asp Pro Ala Pro Glu Glu Ala Glu Glu
65                  70                  75                  80

Val Val Glu Glu Ile Arg His Trp Ser Leu Gly Lys Asn Pro Glu Pro
                85                  90                  95

Trp Ala Glu Gly Leu Val Tyr Ser Val Asp Thr Trp Arg Asp Gln Val
            100                 105                 110

His Ala Phe Ile Glu Lys Val Ile Gly Gly Pro Val Tyr Ile Val Gly
        115                 120                 125

Asn Ser Leu Gly Gly Tyr Val Gly Ser Tyr Phe Ala Ala Thr Asn Pro
    130                 135                 140

Glu Leu Val Lys Gly Val Thr Leu Leu Asn Ala Thr Pro Phe Trp Ala
145                 150                 155                 160

Phe Thr Pro Asn Ser Arg Arg Tyr Pro Leu Leu Ser Lys Leu Thr Pro
                165                 170                 175

Trp Gly Gly Leu Leu Pro Val Pro Ile Phe Ala Lys Ala Ile Ile Arg
            180                 185                 190

Phe Trp Trp Asp Leu Leu Arg Asn Pro Ser Thr Ile Arg Asn Met Leu
        195                 200                 205

Gly Ala Val Tyr Ala Asn Arg Ser Ala Ile Asn Lys Lys Leu Ile Thr
    210                 215                 220

Gln Ile Ile Glu Ala Thr Asp His Pro Ala Ala Phe Ala Ala Phe Ala
225                 230                 235                 240

Ser Ile Val Phe Ala Pro Arg Ala His Thr Asp Phe Gly Glu Asn Leu
                245                 250                 255

Ile Ser Leu Lys Glu Arg Arg Met Pro Met Cys Met Ile Tyr Gly Lys
            260                 265                 270

Glu Asp Pro Trp Val Val Pro Phe Trp Gly Gln Arg Ala Lys Gln Arg
        275                 280                 285
```

-continued

```
Asn Pro Asp Ala Ile Tyr Tyr Glu Leu Ser Pro Ala Gly His Cys Pro
    290                 295                 300

His His Glu Ala Pro Glu Val Leu Phe Pro Ala Gln Ile Val Leu Leu
305                 310                 315                 320

Ala Cys Met Val Gln Asn Ile Ile Gly Lys Ala Arg Pro Leu Phe Lys
                325                 330                 335

Gly

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      Conserved amino acid sequence

<400> SEQUENCE: 13

Leu Pro Gly Phe Gly Val Gly
1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      Conserved amino acid sequence

<400> SEQUENCE: 14

Asp Phe Leu Gly Gln Gly
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      Conserved amino acid sequence

<400> SEQUENCE: 15

Gly Asn Ser Leu Gly Gly
1               5

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      Conserved amino acid sequence

<400> SEQUENCE: 16

Leu Val Lys Gly Val Thr Leu Leu Asn Ala Thr Pro Phe Trp
1               5                   10

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      Conserved amino acid sequence

<400> SEQUENCE: 17
```

His Pro Ala Ala
1

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      Conserved amino acid sequence

<400> SEQUENCE: 18

Glu Asp Pro Trp
1

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      Conserved amino acid sequence

<400> SEQUENCE: 19

Ser Pro Ala Gly His Cys Pro His
1               5

<210> SEQ ID NO 20
<211> LENGTH: 318
<212> TYPE: PRT
<213> ORGANISM: Arabidopsis thaliana

<400> SEQUENCE: 20

Met Ser Ser Ser Ser Arg Asn Ala Phe Glu Asp Gly Lys Tyr Lys
1               5                   10                  15

Ser Asn Leu Leu Thr Leu Asp Ser Ser Arg Cys Cys Lys Ile Thr
                20                  25                  30

Pro Ser Ser Arg Ala Ser Pro Ser Pro Lys Gln Leu Leu Val Ala
                35                  40                  45

Thr Pro Val Glu Glu Gly Asp Tyr Pro Val Val Met Leu Leu His Gly
        50                  55                  60

Tyr Leu Leu Tyr Asn Ser Phe Tyr Ser Gln Leu Met Leu His Val Ser
65                  70                  75                  80

Ser His Gly Phe Ile Leu Ile Ala Pro Gln Leu Tyr Ser Ile Ala Gly
                    85                  90                  95

Pro Asp Thr Met Asp Glu Ile Lys Ser Thr Ala Glu Ile Met Asp Trp
                100                 105                 110

Leu Ser Val Gly Leu Asn His Phe Leu Pro Ala Gln Val Thr Pro Asn
            115                 120                 125

Leu Ser Lys Phe Ala Leu Ser Gly His Ser Arg Gly Gly Lys Thr Ala
        130                 135                 140

Phe Ala Val Ala Leu Lys Lys Phe Gly Tyr Ser Ser Asn Leu Lys Ile
145                 150                 155                 160

Ser Thr Leu Ile Gly Ile Asp Pro Val Asp Gly Thr Gly Lys Gly Lys
                    165                 170                 175

Gln Thr Pro Pro Pro Val Leu Ala Tyr Leu Pro Asn Ser Phe Asp Leu
                180                 185                 190

Asp Lys Thr Pro Ile Leu Val Ile Gly Ser Gly Leu Gly Glu Thr Ala
            195                 200                 205

Arg Asn Pro Leu Phe Pro Pro Cys Ala Pro Pro Gly Val Asn His Arg

```
                210                 215                 220
Glu Phe Phe Arg Glu Cys Gln Gly Pro Ala Trp His Phe Val Ala Lys
225                 230                 235                 240

Asp Tyr Gly His Leu Asp Met Leu Asp Asp Thr Lys Gly Ile Arg
                245                 250                 255

Gly Lys Ser Ser Tyr Cys Leu Cys Lys Asn Gly Glu Glu Arg Arg Pro
            260                 265                 270

Met Arg Arg Phe Val Gly Gly Leu Val Val Ser Phe Leu Lys Ala Tyr
                275                 280                 285

Leu Glu Gly Asp Asp Arg Glu Leu Val Lys Ile Lys Asp Gly Cys His
                290                 295                 300

Glu Asp Val Pro Val Glu Ile Gln Glu Phe Glu Val Ile Met
305                 310                 315

<210> SEQ ID NO 21
<211> LENGTH: 319
<212> TYPE: PRT
<213> ORGANISM: Triticum aestivum

<400> SEQUENCE: 21

Met Ala Ala Ala Ala Pro Ala Glu Thr Met Asn Lys Ser Ala Ala Gly
1               5                   10                  15

Ala Glu Val Pro Glu Ala Phe Thr Ser Val Phe Gln Pro Gly Lys Leu
                20                  25                  30

Ala Val Glu Ala Ile Gln Val Asp Glu Asn Ala Ala Pro Thr Pro Pro
            35                  40                  45

Ile Pro Val Leu Ile Val Ala Pro Lys Asp Ala Gly Thr Tyr Pro Val
50                  55                  60

Ala Met Leu Leu His Gly Phe Phe Leu His Asn His Phe Tyr Glu His
65                  70                  75                  80

Leu Leu Arg His Val Ala Ser His Gly Phe Ile Ile Val Ala Pro Gln
                85                  90                  95

Phe Ser Ile Ser Ile Ile Pro Ser Gly Asp Ala Glu Asp Ile Ala Ala
                100                 105                 110

Ala Ala Lys Val Ala Asp Trp Leu Pro Asp Gly Leu Pro Ser Val Leu
            115                 120                 125

Pro Lys Gly Val Glu Pro Glu Leu Ser Lys Leu Ala Leu Ala Gly His
130                 135                 140

Ser Arg Gly Gly His Thr Ala Phe Ser Leu Ala Leu Gly His Ala Lys
145                 150                 155                 160

Thr Gln Leu Thr Phe Ser Ala Leu Ile Gly Leu Asp Pro Val Ala Gly
                165                 170                 175

Thr Gly Lys Ser Ser Gln Leu Gln Pro Lys Ile Leu Thr Tyr Glu Pro
            180                 185                 190

Ser Ser Phe Gly Met Ala Met Pro Val Leu Val Ile Gly Thr Gly Leu
            195                 200                 205

Gly Glu Glu Lys Lys Asn Ile Phe Phe Pro Cys Ala Pro Lys Asp
210                 215                 220

Val Asn His Ala Glu Phe Tyr Arg Glu Cys Arg Pro Pro Cys Tyr Tyr
225                 230                 235                 240

Phe Val Thr Lys Asp Tyr Gly His Leu Asp Met Leu Asp Asp Asp Ala
                245                 250                 255

Pro Lys Phe Ile Thr Cys Val Cys Lys Asp Gly Asn Gly Cys Lys Gly
            260                 265                 270
```

Lys Met Arg Arg Cys Val Ala Gly Ile Met Val Ala Phe Leu Asn Ala
                275                 280                 285

Ala Leu Gly Glu Lys Asp Ala Asp Leu Glu Ala Ile Leu Arg Asp Pro
            290                 295                 300

Ala Val Ala Pro Thr Thr Leu Asp Pro Val Glu His Arg Val Ala
305                 310                 315

<210> SEQ ID NO 22
<211> LENGTH: 984
<212> TYPE: DNA
<213> ORGANISM: Triticum aestivum

<400> SEQUENCE: 22

```
gcgcgcaggc tgctggaaaa atggcagcgg ctgccccggc cgaaacaatg aataaaagcg      60
cagcgggtgc cgaagttcct gaagcattta cgtctgtgtt tcaaccgggc aaattggctg     120
tcgaagccat tcaggtagac gaaaacgctg ccctacacc gcctattccg gtcctgatcg      180
tagcaccta agatgcggga acgtatccg tcgcgatgct gcttcatggc ttttcctgc        240
ataaccattt ttacgaacat tgttgcgtc atgtcgcgtc ccatggattt atcatcgtag      300
ctcctcaatt tcaattagc attatcccgt caggcgacgc ggaagatatc gcagcggctg      360
ccaaagttgc tgactggctg ccggatggcc ttcctagcgt tttaccgaaa ggcgttgaac      420
ctgaactttc taaactggct cttgccggac attcccgcgg cggacataca gcttttcat     480
tagccttggg ccatgcaaaa acacagttaa cgttttctgc cctgattgga cttgatccgg      540
ttgcaggtac aggcaaatca agccaattgc agcctaaaat cctgacgtat gaaccgtctt      600
cctttggcat ggctatgcct gttcttgtga ttggaacagg tttgggcgaa gaaaagaaaa      660
atattttctt tccgccgtgc gccccgaaag atgttaacca tgcagaattt atcgtgaat      720
gccggccgcc ttgttattac tttgtgacaa aagactacga catttagat atgttggatg      780
acgatgcacc gaaatttatt acgtgcgtct gtaaagatgg aaatggttgc aaaggtaaaa      840
tgagacgctg tgtcgcgggc attatggtag catttctgaa cgcagcgctg ggcgaaaaag      900
acgcggatct tgaagctatc ttaagagacc cggcagttgc gccgacaacg cttgatccgg      960
ttgaacatcg cgtggcttaa ttaa                                            984
```

<210> SEQ ID NO 23
<211> LENGTH: 322
<212> TYPE: PRT
<213> ORGANISM: Chlamydomonas reinhardtii

<400> SEQUENCE: 23

Met Pro Ser Thr Gln Phe Leu Gly Ala Ser Thr Leu Leu Leu Phe Gly
1               5                   10                  15

Leu Arg Ala Val Met Ser Ser Asp Asp Tyr Ile Lys Arg Gly Asp Leu
            20                  25                  30

Pro Thr Ser Lys Trp Ser Gly Arg Val Thr Leu Arg Val Asp Ser Ala
        35                  40                  45

Met Ala Val Pro Leu Asp Val Val Ile Thr Tyr Pro Ser Ser Gly Ala
    50                  55                  60

Ala Ala Tyr Pro Val Leu Val Met Tyr Asn Gly Phe Gln Ala Lys Ala
65                  70                  75                  80

Pro Trp Tyr Arg Gly Ile Val Asp His Val Ser Ser Trp Gly Tyr Thr
                85                  90                  95

Val Val Gln Tyr Thr Asn Gly Gly Leu Phe Pro Ile Val Val Asp Arg
            100                 105                 110

Val Glu Leu Thr Tyr Leu Glu Pro Leu Leu Thr Trp Leu Glu Thr Gln
             115                 120                 125

Ser Ala Asp Ala Lys Ser Pro Leu Tyr Gly Arg Ala Asp Val Ser Arg
         130                 135                 140

Leu Gly Thr Met Gly His Ser Arg Gly Lys Leu Ala Ala Leu Gln
145                 150                 155                 160

Phe Ala Gly Arg Thr Asp Val Ser Gly Cys Val Leu Phe Asp Pro Val
                 165                 170                 175

Asp Gly Ser Pro Met Thr Pro Glu Ser Ala Asp Tyr Pro Ser Ala Thr
             180                 185                 190

Lys Ala Leu Ala Ala Gly Arg Ser Ala Gly Leu Val Gly Ala Ala
         195                 200                 205

Ile Thr Gly Ser Cys Asn Pro Val Gly Gln Asn Tyr Pro Lys Phe Trp
         210                 215                 220

Gly Ala Leu Ala Pro Gly Ser Trp Gln Met Val Leu Ser Gln Ala Gly
225                 230                 235                 240

His Met Gln Phe Ala Arg Thr Gly Asn Pro Phe Leu Asp Trp Ser Leu
                 245                 250                 255

Asp Arg Leu Cys Gly Arg Gly Thr Met Met Ser Ser Asp Val Ile Thr
             260                 265                 270

Tyr Ser Ala Ala Phe Thr Val Ala Trp Phe Glu Gly Ile Phe Arg Pro
         275                 280                 285

Ala Gln Ser Gln Met Gly Ile Ser Asn Phe Lys Thr Trp Ala Asn Thr
         290                 295                 300

Gln Val Ala Ala Arg Ser Ile Thr Phe Asp Ile Lys Pro Met Gln Ser
305                 310                 315                 320

Pro Gln

<210> SEQ ID NO 24
<211> LENGTH: 997
<212> TYPE: DNA
<213> ORGANISM: Chlamydomonas reinhardtii

<400> SEQUENCE: 24
gcgcgcaggc tgctggaaaa atgccttcta cacaatttct tggagcatcc acgctgcttt      60
tatttggttt acgtgcggtc atgtcaagcg atgactatat aaacggggt gatttgccga      120 catcaaaatg gagcggaaga gtcacgttgc gcgtagattc agctatggcc gttccgctgg      180
acgttgtgat cacatatcct tcttccggcg cagcggctta ccggtcctg gtaatgtaca      240 atggatttca ggcaaaagcg ccgtggtaca gaggcattgt tgatcatgtg tcaagctggg      300
gatatacagt cgtacaatac acgaacggcg gactttttcc tatcgttgtg gaccgcgtcg      360
aacttacata tttagaaccg ttgctgacat ggttagaaac gcagtctgct gatgccaaat      420
ccccgttgta cggcagagct gacgtatcac gcctgggcac aatgggacat agcagaggtg      480
gcaaattggc cgcactgcaa tttgcgggcc gcacggatgt ttcaggatgc gtgctttttg      540
atcctgtgga cggcagcccg atgacacctg aatcagctga ctatccgagc gctacgaaag      600
cacttgcggc tgccggacgt tctgccggtt tagttggcgc agcgattaca ggttcatgta      660
atccggtggg ccagaactac cctaaatttt ggggagcatt ggcgcctggt tcatggcaaa      720
tggtcctgag ccaggcaggc catatgcaat ttgcgagaac aggaaatccg tttttagatt      780
ggagccttga ccgtttatgc ggacggggta cgatgatgtc ttccgatgtc atacatatt      840 ctgctgcctt tacggtagct tggtttgaag gcattttctcg tccggcccaa tctcagatgg      900

```
gaatctccaa ttttaaaaca tgggcaaaca cgcaagttgc agcgcggtct attacatttg    960
atatcaaacc gatgcaatcc cctcagtaat taattaa                             997
```

<210> SEQ ID NO 25
<211> LENGTH: 303
<212> TYPE: PRT
<213> ORGANISM: Triticum aestivum

<400> SEQUENCE: 25

```
Ala Glu Val Pro Glu Ala Phe Thr Ser Val Phe Gln Pro Gly Lys Leu
1               5                   10                  15

Ala Val Glu Ala Ile Gln Val Asp Glu Asn Ala Ala Pro Thr Pro Pro
            20                  25                  30

Ile Pro Val Leu Ile Val Ala Pro Lys Asp Ala Gly Thr Tyr Pro Val
        35                  40                  45

Ala Met Leu Leu His Gly Phe Phe Leu His Asn His Phe Tyr Glu His
    50                  55                  60

Leu Leu Arg His Val Ala Ser His Gly Phe Ile Val Ala Pro Gln
65                  70                  75                  80

Phe Ser Ile Ser Ile Pro Ser Gly Asp Ala Glu Asp Ile Ala Ala
                85                  90                  95

Ala Ala Lys Val Ala Asp Trp Leu Pro Asp Gly Leu Pro Ser Val Leu
            100                 105                 110

Pro Lys Gly Val Glu Pro Glu Leu Ser Lys Leu Ala Leu Ala Gly His
        115                 120                 125

Ser Arg Gly Gly His Thr Ala Phe Ser Leu Ala Leu Gly His Ala Lys
    130                 135                 140

Thr Gln Leu Thr Phe Ser Ala Leu Ile Gly Leu Asp Pro Val Ala Gly
145                 150                 155                 160

Thr Gly Lys Ser Ser Gln Leu Gln Pro Lys Ile Leu Thr Tyr Glu Pro
                165                 170                 175

Ser Ser Phe Gly Met Ala Met Pro Val Leu Val Ile Gly Thr Gly Leu
            180                 185                 190

Gly Glu Glu Lys Lys Asn Ile Phe Phe Pro Pro Cys Ala Pro Lys Asp
        195                 200                 205

Val Asn His Ala Glu Phe Tyr Arg Glu Cys Arg Pro Pro Cys Tyr Tyr
    210                 215                 220

Phe Val Thr Lys Asp Tyr Gly His Leu Asp Met Leu Asp Asp Asp Ala
225                 230                 235                 240

Pro Lys Phe Ile Thr Cys Val Cys Lys Asp Gly Asn Gly Cys Lys Gly
                245                 250                 255

Lys Met Arg Arg Cys Val Ala Gly Ile Met Val Ala Phe Leu Asn Ala
            260                 265                 270

Ala Leu Gly Glu Lys Asp Ala Asp Leu Glu Ala Ile Leu Arg Asp Pro
        275                 280                 285

Ala Val Ala Pro Thr Thr Leu Asp Pro Val Glu His Arg Val Ala
    290                 295                 300
```

<210> SEQ ID NO 26
<211> LENGTH: 936
<212> TYPE: DNA
<213> ORGANISM: Triticum aestivum

<400> SEQUENCE: 26

```
gcgcgcaggc tgctggaaaa gccgaggtcc cggaagcctt taccagcgtc ttccagcctg    60
```

```
gcaagcttgc cgtcgaggcc atccaggtcg atgaaaacgc tgctcctacc ccgcccatcc      120
cggtcctgat tgtcgctccg aaagacgccg gcacgtaccc tgtcgccatg ctgctccatg      180 gcttttcct ccacaaccat ttttatgagc accttctgcg ccatgtcgcc tcccacggct       240
ttatcattgt cgcccctcag ttcagcatct ccatcattcc ctctggcgat gccgaagaca      300
ttgctgccgc cgccaaagtc gctgattggc tgcctgatgg cctcccgagc gtccttccta      360
agggcgtcga gcctgaactc tctaaactcg cccttgctgg ccattcgcgc ggcggccata      420
cagcttttag cctggctctg ggccacgcca aaacacagct gaccttcagc gcccttattg      480
gcctggaccc ggtcgctggc acaggcaaga gctcccagct ccagcccaaa attcttacat      540
acgagccgtc ttcgttcggc atggccatgc cggtcctggt cattggcaca ggcctcggcg      600
aggaaaagaa aaacatcttt ttcccgccct gcgccccgaa ggatgtcaac catgccgagt      660
tttaccgcga atgccgcccg ccttgctact atttcgtcac aaaagattat ggccacctcg      720
acatgcttga cgatgacgcc ccgaagttta ttacctgcgt ctgcaaagac ggcaacggct      780
gcaagggcaa aatgcgcaga tgcgtcgccg gcatcatggt cgccttcctg aacgctgctc      840
tgggcgagaa ggatgctgac cttgaagcca ttctgcgcga tcccgccgtc gctcccacca      900
cactggaccc tgtcgaacac cgcgtcgctt aattaa                                936
```

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      Kexin linker sequence

<400> SEQUENCE: 27

Thr Ser Val Ala Val Glu Lys Arg
1               5

<210> SEQ ID NO 28
<211> LENGTH: 136
<212> TYPE: PRT
<213> ORGANISM: Arabidopsis thaliana

<400> SEQUENCE: 28

Glu Ser Thr Ser Lys Val Leu Ile Pro Gly Leu Pro Asp Glu Ser Asn
1               5                   10                  15

Gly Glu Ile Ala Ala Arg Ile Ser His Ser Cys Glu Trp Lys Pro
            20                  25                  30

Lys Leu Arg Val His Tyr Glu Lys Ala Gly Cys Asp Asn Leu Asp Ala
        35                  40                  45

Pro Ala Val Leu Phe Leu Pro Gly Phe Gly Val Gly Ser Phe His Tyr
    50                  55                  60

Glu Lys Gln Leu Thr Asp Leu Gly Arg Asp Tyr Arg Val Trp Ala Ile
65                  70                  75                  80

Asp Phe Leu Gly Gln Gly Leu Ser Leu Pro Thr Glu Asp Pro Thr Thr
                85                  90                  95

Met Thr Glu Glu Thr Ser Ser Glu Asp Lys Glu Pro Phe Trp Gly
            100                 105                 110

Phe Gly Asp Lys Thr Glu Pro Trp Ala Asp Gln Leu Val Phe Ser Leu
        115                 120                 125

Asp Leu Trp Arg Asp Gln Val Gln
    130                 135

```
<210> SEQ ID NO 29
<211> LENGTH: 131
<212> TYPE: PRT
<213> ORGANISM: Oryza sativa

<400> SEQUENCE: 29

Gly Glu Ile Glu Lys Met Ile Ile Pro Ser Leu Pro Glu Gly Pro Glu
1               5                   10                  15

Ser Ser Leu Ile Ser Thr Gly Phe Trp Glu Trp Lys Pro Lys Leu Ser
            20                  25                  30

Val Tyr Tyr Glu Lys Ser Gly Ile Asp Asn Ser Lys Ala Pro Ser Val
        35                  40                  45

Leu Phe Leu Pro Gly Phe Gly Val Gly Thr Phe His Phe Glu Lys Gln
    50                  55                  60

Leu Lys Asp Leu Gly Arg Asp Tyr Lys Val Trp Thr Met Asp Phe Leu
65                  70                  75                  80

Gly Gln Gly Met Ser Leu Pro Cys Glu Asp Pro Ala Pro Lys Ser Thr
                85                  90                  95

Ser Gly Glu Leu Asp Glu Asp Thr Tyr Trp Gly Phe Gly Gln Glu Leu
            100                 105                 110

Gln Pro Trp Ala Glu Glu Leu Val Tyr Ser Ile Asp Leu Trp Arg Asp
        115                 120                 125

Gln Val Gln
    130

<210> SEQ ID NO 30
<211> LENGTH: 131
<212> TYPE: PRT
<213> ORGANISM: Oryza sativa

<400> SEQUENCE: 30

Gly Glu Ile Glu Lys Met Ile Ile Pro Ser Leu Pro Glu Gly Pro Glu
1               5                   10                  15

Ser Ser Leu Ile Ser Thr Gly Phe Trp Glu Trp Lys Pro Lys Leu Ser
            20                  25                  30

Val Tyr Tyr Glu Lys Ser Gly Ile Asp Asn Ser Lys Ala Pro Ser Val
        35                  40                  45

Leu Phe Leu Pro Gly Phe Gly Val Gly Thr Phe His Phe Glu Lys Gln
    50                  55                  60

Leu Lys Asp Leu Gly Arg Asp Tyr Lys Val Trp Thr Met Asp Phe Leu
65                  70                  75                  80

Gly Gln Gly Met Ser Leu Pro Cys Glu Asp Pro Ala Pro Lys Ser Thr
                85                  90                  95

Ser Gly Glu Leu Asp Glu Asp Thr Tyr Trp Gly Phe Gly Gln Glu Leu
            100                 105                 110

Gln Pro Trp Ala Glu Glu Leu Val Tyr Ser Ile Asp Leu Trp Arg Asp
        115                 120                 125

Gln Val Gln
    130

<210> SEQ ID NO 31
<211> LENGTH: 131
<212> TYPE: PRT
<213> ORGANISM: Oryza sativa

<400> SEQUENCE: 31
```

```
Gly Glu Ile Glu Lys Met Ile Ile Pro Ser Leu Pro Glu Gly Pro Glu
1               5                   10                  15

Ser Ser Leu Ile Ser Thr Gly Phe Trp Glu Trp Lys Pro Lys Leu Ser
            20                  25                  30

Val Tyr Tyr Glu Lys Ser Gly Ile Asp Asn Ser Lys Ala Pro Ser Val
            35                  40                  45

Leu Phe Leu Pro Gly Phe Gly Val Gly Thr Phe His Phe Glu Lys Gln
50                  55                  60

Leu Lys Asp Leu Gly Arg Asp Tyr Lys Val Trp Thr Met Asp Phe Leu
65                  70                  75                  80

Gly Gln Gly Met Ser Leu Pro Cys Glu Asp Pro Ala Pro Lys Ser Thr
                85                  90                  95

Ser Gly Glu Leu Asp Glu Asp Thr Tyr Trp Gly Phe Gly Gln Glu Leu
                100                 105                 110

Gln Pro Trp Ala Glu Glu Leu Val Tyr Ser Ile Asp Leu Trp Arg Asp
                115                 120                 125

Gln Val Gln
        130

<210> SEQ ID NO 32
<211> LENGTH: 128
<212> TYPE: PRT
<213> ORGANISM: Zea mays

<400> SEQUENCE: 32

Gly Glu Ala Glu Arg Val Met Ile Gln Gly Leu Pro Glu Gly Pro Asp
1               5                   10                  15

Ser Ser Pro Ile Ser Thr Gly Phe Trp Glu Trp Lys Pro Lys Leu Thr
            20                  25                  30

Val His Tyr Glu Arg Ser Gly Met Lys Asn Ser Lys Ala Pro Ala Val
            35                  40                  45

Leu Phe Leu Pro Gly Phe Gly Val Gly Thr Phe His Phe Glu Lys Gln
50                  55                  60

Leu Arg Asp Leu Gly Arg Asp His Arg Val Trp Thr Met Asp Phe Leu
65                  70                  75                  80

Gly Gln Gly Met Ser Leu Pro Gly Glu Asp Pro Ala Pro Ser Ser Ile
                85                  90                  95

Ala Ser Glu Asp Ala Phe Trp Gly Phe Gly Gln Asp Ser Gln Pro Trp
                100                 105                 110

Ala Glu Glu Leu Val Tyr Ser Val Asp Leu Trp Gln Asn Gln Val Gln
                115                 120                 125

<210> SEQ ID NO 33
<211> LENGTH: 138
<212> TYPE: PRT
<213> ORGANISM: Nicotiana tabacum

<400> SEQUENCE: 33

Lys Ser Val Pro Lys Val Ile Val Pro Ser Leu Pro Asp Glu Thr Lys
1               5                   10                  15

Ala Asp Ser Val Ala Val Val Asp Ser Cys Leu Trp Glu Trp Lys Pro
            20                  25                  30

Lys Leu Lys Val His Tyr Glu Lys Ser Gly Cys Gln Asn Val Asn Ser
            35                  40                  45

Ala Pro Ile Leu Phe Leu Pro Gly Phe Gly Val Gly Ser Phe His Tyr
50                  55                  60
```

```
Glu Lys Gln Leu Lys Asp Leu Gly Cys Asp His Arg Ile Trp Ala Leu
 65                  70                  75                  80

Asp Phe Leu Gly Gln Gly Lys Ser Leu Pro Cys Glu Asp Pro Thr Leu
                 85                  90                  95

Gln Ser Lys Arg Leu Asp Glu Ser Glu Arg Asp Gly Asn Asn Ala Val
            100                 105                 110

Trp Gly Phe Gly Asp Glu Ala Glu Pro Trp Ala Lys Glu Leu Val Tyr
        115                 120                 125

Ser Val Asp Leu Trp Arg Asp Gln Val Arg
    130                 135

<210> SEQ ID NO 34
<211> LENGTH: 136
<212> TYPE: PRT
<213> ORGANISM: Vitis vinifera

<400> SEQUENCE: 34

Asp Leu Ile Thr Gln Ile Leu Ile Pro Gly Leu Pro Asp Ser Asn
 1               5                  10                  15

Asp Asp Ser Gly Ala Gln Ile Ser Ser Cys Phe Trp Glu Trp Lys Pro
                 20                  25                  30

Lys Leu Thr Val His Tyr Glu Lys Ser Gly Cys Glu Asn Val Asn Ser
             35                  40                  45

Pro Pro Val Leu Phe Leu Pro Gly Phe Val Gly Ser Phe His Tyr
 50                  55                  60

Glu Lys Gln Leu Lys Asp Leu Gly Arg Asp Phe Arg Val Trp Ala Val
 65                  70                  75                  80

Asp Phe Leu Gly Gln Gly Met Ser Leu Pro Phe Glu Asp Pro Ala Pro
                 85                  90                  95

Gln Ser Lys Lys Glu Leu Asp Ser Glu Arg Asn Asp Phe Ser Trp Gly
            100                 105                 110

Phe Gly Asp Glu Thr Glu Pro Trp Ala Asn Glu Leu Val Tyr Ser Ile
        115                 120                 125

Asp Leu Trp Gln Asp Gln Val Arg
    130                 135

<210> SEQ ID NO 35
<211> LENGTH: 136
<212> TYPE: PRT
<213> ORGANISM: Populus trichocarpa

<400> SEQUENCE: 35

Glu Ser Pro Thr Lys Val Leu Ile Pro Gly Leu Pro Asp Glu Ser Asn
 1               5                  10                  15

Gly Glu Tyr Ser Ala Pro Val Ser Ser Cys Phe Trp Lys Trp Lys Pro
                 20                  25                  30

Lys Leu Asn Val His Tyr Glu Lys Ala Gly Cys Glu Asn Val Asn Ser
             35                  40                  45

Pro Pro Val Leu Phe Leu Pro Gly Phe Gly Val Ser Phe His Tyr
 50                  55                  60

Glu Lys Gln Leu Lys Asp Leu Gly Arg Asp Tyr Arg Val Trp Ala Ile
 65                  70                  75                  80

Asp Phe Leu Gly Gln Gly Met Ser Leu Pro Val Glu Asn Pro Thr Leu
                 85                  90                  95

Phe Ser Lys Asp Gly Ala Ser Glu Gly Lys Asp Ser Ile Trp Gly
            100                 105                 110
```

```
Phe Gly Asp Glu Ile Glu Pro Trp Ala Asn Asp Leu Val Phe Ser Met
            115                 120                 125

Asp Leu Trp Gln Asp Gln Val His
    130                 135

<210> SEQ ID NO 36
<211> LENGTH: 136
<212> TYPE: PRT
<213> ORGANISM: Ricinus communis

<400> SEQUENCE: 36

Glu Ser Thr Pro Glu Ile Leu Ile Pro Gly Leu Pro Asn Glu Ser Ser
1               5                   10                  15

Gly Glu Cys Gly Ala Pro Ile Asn Ser Cys Phe Trp Glu Trp Lys Pro
            20                  25                  30

Lys Leu Tyr Val His Tyr Glu Lys Ala Gly Cys Glu Asn Val Lys Ser
        35                  40                  45

Pro Pro Val Leu Phe Leu Pro Gly Phe Gly Val Gly Ser Phe His Phe
    50                  55                  60

Glu Asn Gln Leu Lys Asp Leu Gly Arg Asp Tyr Arg Val Trp Ala Ile
65                  70                  75                  80

Asp Phe Leu Gly Gln Gly Met Ser Leu Pro Val Glu Asn Pro Thr Leu
                85                  90                  95

Gln Leu Arg Glu Gly Asp Ile Leu Glu Gly Lys Asn Ser Phe Trp Gly
            100                 105                 110

Phe Gly Asp Glu Thr Glu Pro Trp Ala Asn Glu Leu Val Tyr Ser Met
            115                 120                 125

Asp Leu Trp Arg Asp Gln Val Arg
    130                 135

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      Consensus sequence

<400> SEQUENCE: 37

Lys Val Ile Ile Pro Gly Leu Pro Asp Glu Ser
1               5                   10

<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: Synthetic
      Consensus sequence

<400> SEQUENCE: 38

Phe Trp Glu Trp Lys Pro Lys Leu Ser Val His Tyr Glu Lys Ser Gly
1               5                   10                  15

<210> SEQ ID NO 39
<211> LENGTH: 48
<212> TYPE: PRT
<213> ORGANISM: Artificial Sequence
<220> FEATURE:
<223> OTHER INFORMATION: Description of Artificial Sequence: Synthetic
      Consensus sequence

<400> SEQUENCE: 39
```

```
Cys Asp Asn Val Lys Ala Pro Ala Val Leu Phe Leu Pro Gly Phe Gly
1               5                   10                  15

Val Gly Ser Phe His Phe Glu Lys Gln Leu Lys Asp Leu Gly Arg Asp
            20                  25                  30

Tyr Arg Val Trp Ala Ile Asp Phe Leu Gly Gln Gly Met Ser Leu Pro
        35                  40                  45

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      Consensus sequence

<400> SEQUENCE: 40

Glu Asp Pro Ala Pro
1               5

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      Consensus sequence

<400> SEQUENCE: 41

Asp Glu Asp Thr Phe Trp Gly Phe Gly Asp Glu
1               5                   10

<210> SEQ ID NO 42
<211> LENGTH: 19
<212> TYPE: PRT
<213> ORGANISM: Artificial Sequence
<220> FEATURE:
<223> OTHER INFORMATION: Description of Artificial Sequence: Synthetic
      Consensus sequence

<400> SEQUENCE: 42

Glu Pro Trp Ala Glu Glu Leu Val Tyr Ser Ile Asp Leu Trp Arg Asp
1               5                   10                  15

Gln Val Gln

<210> SEQ ID NO 43
<211> LENGTH: 28
<212> TYPE: PRT
<213> ORGANISM: Artificial Sequence
<220> FEATURE:
<223> OTHER INFORMATION: Description of Artificial Sequence: Synthetic
      Consensus sequence

<400> SEQUENCE: 43

Phe Ile Glu Glu Val Ile Gly Glu Pro Val Tyr Ile Val Gly Asn Ser
1               5                   10                  15

Leu Gly Gly Phe Val Ala Leu Tyr Phe Ala Ala Ser
            20                  25

<210> SEQ ID NO 44
<211> LENGTH: 49
<212> TYPE: PRT
<213> ORGANISM: Artificial Sequence
<220> FEATURE:
<223> OTHER INFORMATION: Description of Artificial Sequence: Synthetic
      Consensus sequence
```

<400> SEQUENCE: 44

Pro His Leu Val Lys Gly Val Thr Leu Leu Asn Ala Thr Pro Phe Trp
1               5                   10                  15

Gly Phe Leu Pro Asn Pro Ala Arg Ser Pro Arg Leu Ser Lys Ile Phe
            20                  25                  30

Pro Trp Ala Gly Thr Phe Pro Leu Pro Ser Phe Val Arg Lys Leu Thr
            35                  40                  45

Glu

<210> SEQ ID NO 45
<211> LENGTH: 59
<212> TYPE: PRT
<213> ORGANISM: Artificial Sequence
<220> FEATURE:
<223> OTHER INFORMATION: Description of Artificial Sequence: Synthetic
      Consensus sequence

<400> SEQUENCE: 45

Val Trp Gln Lys Ile Ser Asp Pro Arg Ser Ile Ala Glu Ile Leu Lys
1               5                   10                  15

Gln Val Tyr Ala Asp His Ser Thr Asn Val Asp Lys Val Phe Ser Arg
            20                  25                  30

Ile Ile Glu Ile Thr Gln His Pro Ala Ala Ala Ala Ser Phe Ala Ser
            35                  40                  45

Ile Met Phe Ala Pro Lys Gly Gln Leu Ser Phe
        50                  55

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Synthetic
      Consensus sequence

<400> SEQUENCE: 46

Ala Leu Ser Arg Cys Gln
1               5

<210> SEQ ID NO 47
<211> LENGTH: 62
<212> TYPE: PRT
<213> ORGANISM: Artificial Sequence
<220> FEATURE:
<223> OTHER INFORMATION: Description of Artificial Sequence: Synthetic
      Consensus sequence

<400> SEQUENCE: 47

Ile Pro Ile Cys Leu Met Tyr Gly Arg Glu Asp Pro Trp Val Arg Pro
1               5                   10                  15

Ile Trp Gly Leu Lys Val Lys Gln Gln Val Pro Glu Ala Pro Tyr Tyr
            20                  25                  30

Glu Ile Ser Pro Ala Gly His Cys Pro His Asp Glu Val Pro Glu Val
        35                  40                  45

Val Asn Tyr Leu Leu Arg Gly Trp Ile Lys Asn Leu Glu Ser
        50                  55                  60

<210> SEQ ID NO 48
<211> LENGTH: 6
<212> TYPE: PRT
<213> ORGANISM: Artificial Sequence

```
<220> FEATURE:
<223> OTHER INFORMATION: Description of Artificial Sequence: Synthetic
      Consensus sequence

<400> SEQUENCE: 48

Gly Ser Val Ala Leu Pro
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      Consensus sequence

<400> SEQUENCE: 49

Arg Glu Leu Glu Phe Val Arg
1               5

<210> SEQ ID NO 50
<211> LENGTH: 6
<212> TYPE: PRT
<213> ORGANISM: Artificial Sequence
<220> FEATURE:
<223> OTHER INFORMATION: Description of Artificial Sequence: Synthetic
      Consensus sequence

<400> SEQUENCE: 50

Gly Ser Lys Lys Ser Val
1               5

<210> SEQ ID NO 51
<211> LENGTH: 4
<212> TYPE: PRT
<213> ORGANISM: Artificial Sequence
<220> FEATURE:
<223> OTHER INFORMATION: Description of Artificial Sequence: Synthetic
      Consensus sequence

<400> SEQUENCE: 51

Tyr Gly Ser Lys
1

<210> SEQ ID NO 52
<211> LENGTH: 113
<212> TYPE: PRT
<213> ORGANISM: Physcomitrella patens
<220> FEATURE:
<223> OTHER INFORMATION: subsp. patens

<400> SEQUENCE: 52

Ile Ala Ser His Ile Trp Glu Trp Arg His Arg Trp Asn Ile His Tyr
1               5                   10                  15

Glu Cys Ala Gly Thr Ser Leu Asn Thr Asn Ala Pro Ala Met Leu Leu
            20                  25                  30

Leu Pro Gly Phe Gly Val Gly Ser Phe His Tyr His Gln Gln Leu Arg
        35                  40                  45

Asp Leu Gly Gln Glu Tyr Arg Val Trp Ala Ile Asp Phe Leu Gly Gln
    50                  55                  60

Gly Lys Ser Trp Pro Ser His Asp Pro Ala Pro Glu Glu Ala Glu Glu
65                  70                  75                  80

Val Val Glu Glu Ile Arg His Trp Ser Leu Gly Lys Asn Pro Glu Pro
                85                  90                  95
```

Trp Ala Glu Gly Leu Val Tyr Ser Val Asp Thr Trp Arg Asp Gln Val
              100                 105                 110

His

<210> SEQ ID NO 53
<211> LENGTH: 139
<212> TYPE: PRT
<213> ORGANISM: Arabidopsis thaliana

<400> SEQUENCE: 53

Phe Val Glu Glu Val Ile Gly Glu Pro Val Tyr Ile Ala Gly Asn Ser
1               5                   10                  15

Leu Gly Gly Tyr Val Ala Leu Tyr Phe Ala Ala Thr His Pro His Leu
                20                  25                  30

Val Lys Gly Val Thr Leu Leu Asn Ala Thr Pro Phe Trp Gly Phe Phe
            35                  40                  45

Pro Asn Pro Val Arg Ser Pro Lys Leu Ala Arg Leu Phe Pro Trp Pro
        50                  55                  60

Gly Ala Phe Pro Leu Pro Glu Arg Val Lys Lys Ile Thr Glu Leu Val
65                  70                  75                  80

Trp Gln Lys Ile Ser Asp Pro Glu Ser Ile Ala Glu Ile Leu Lys Gln
                85                  90                  95

Val Tyr Thr Asp His Ser Ile Asn Val Asp Lys Val Phe Ser Arg Ile
            100                 105                 110

Val Glu Val Thr Gln His Pro Ala Ala Ala Ser Phe Ala Ser Ile
        115                 120                 125

Met Leu Ala Pro Gly Gly Glu Leu Ser Phe Ser
    130                 135

<210> SEQ ID NO 54
<211> LENGTH: 139
<212> TYPE: PRT
<213> ORGANISM: Oryza sativa

<400> SEQUENCE: 54

Phe Ile Glu Glu Val Ile Gly Glu Pro Val Tyr Ile Val Gly Asn Ser
1               5                   10                  15

Leu Gly Gly Phe Val Ser Leu Tyr Leu Ala Ala Ser Cys Pro His Leu
                20                  25                  30

Val Lys Gly Val Thr Leu Leu Asn Ala Thr Pro Phe Trp Gly Phe Leu
            35                  40                  45

Pro Asn Pro Ala Thr Ser Pro Arg Leu Ser Lys Ile Phe Pro Trp Ala
        50                  55                  60

Gly Thr Phe Pro Leu Pro Ser Phe Val Arg Lys Leu Thr Glu Thr Val
65                  70                  75                  80

Trp Gln Lys Ile Ser Asp Pro Arg Ser Ile Gln Gly Ile Leu Lys Gln
                85                  90                  95

Val Tyr Ala Asp His Ser Thr Asn Val Asp Met Val Phe Ser Arg Ile
            100                 105                 110

Ile Glu Thr Thr Gln His Pro Ala Ala Ala Ser Phe Ala Ser Ile
        115                 120                 125

Met Cys Ala Pro Lys Gly Gln Ile Ser Phe Glu
    130                 135

<210> SEQ ID NO 55
<211> LENGTH: 139
<212> TYPE: PRT

<213> ORGANISM: Oryza sativa

<400> SEQUENCE: 55

Phe Ile Glu Glu Val Ile Gly Glu Pro Val Tyr Ile Val Gly Asn Ser
1               5                   10                  15

Leu Gly Gly Phe Val Ser Leu Tyr Leu Ala Ala Ser Cys Pro His Leu
            20                  25                  30

Val Lys Gly Val Thr Leu Leu Asn Ala Thr Pro Phe Trp Gly Phe Leu
        35                  40                  45

Pro Asn Pro Ala Thr Ser Pro Arg Leu Ser Lys Ile Phe Pro Trp Ala
50                  55                  60

Gly Thr Phe Pro Leu Pro Ser Phe Val Arg Lys Leu Thr Glu Thr Val
65                  70                  75                  80

Trp Gln Lys Ile Ser Asp Pro Arg Ser Ile Gln Gly Ile Leu Lys Gln
                85                  90                  95

Val Tyr Ala Asp His Ser Thr Asn Val Asp Met Val Phe Ser Arg Ile
            100                 105                 110

Ile Glu Thr Thr Gln His Pro Ala Ala Ala Ser Phe Ala Ser Ile
        115                 120                 125

Met Cys Ala Pro Lys Gly Gln Ile Ser Phe Glu
    130                 135

<210> SEQ ID NO 56
<211> LENGTH: 139
<212> TYPE: PRT
<213> ORGANISM: Oryza sativa

<400> SEQUENCE: 56

Phe Ile Glu Glu Val Ile Gly Glu Pro Val Tyr Ile Val Gly Asn Ser
1               5                   10                  15

Leu Gly Gly Phe Val Ser Leu Tyr Leu Ala Ala Ser Cys Pro His Leu
            20                  25                  30

Val Lys Gly Val Thr Leu Leu Asn Ala Thr Pro Phe Trp Gly Phe Leu
        35                  40                  45

Pro Asn Pro Ala Thr Ser Pro Arg Leu Ser Lys Ile Phe Pro Trp Ala
50                  55                  60

Gly Thr Phe Pro Leu Pro Ser Phe Val Arg Lys Leu Thr Glu Thr Val
65                  70                  75                  80

Trp Gln Lys Ile Ser Asp Pro Arg Ser Ile Gln Gly Ile Leu Lys Gln
                85                  90                  95

Val Tyr Ala Asp His Ser Thr Asn Val Asp Met Val Phe Ser Arg Ile
            100                 105                 110

Ile Glu Thr Thr Gln His Pro Ala Ala Ala Ser Phe Ala Ser Ile
        115                 120                 125

Met Cys Ala Pro Lys Gly Gln Ile Ser Phe Glu
    130                 135

<210> SEQ ID NO 57
<211> LENGTH: 139
<212> TYPE: PRT
<213> ORGANISM: Zea mays

<400> SEQUENCE: 57

Phe Ile Glu Glu Val Ile Arg Glu Pro Val Tyr Ile Val Gly Asn Ser
1               5                   10                  15

Leu Gly Gly Phe Val Ala Leu Tyr Phe Ala Ala Ser Ser Pro His Leu
            20                  25                  30

```
Val Lys Gly Val Thr Leu Leu Asn Ala Thr Pro Phe Trp Gly Phe Phe
             35                  40                  45

Pro Asn Pro Ala Thr Ser Pro Arg Leu Ser Lys Ile Phe Pro Trp Ala
         50                  55                  60

Gly Thr Phe Pro Leu Pro Ser Phe Val Arg Lys Ile Thr Glu Ala Val
 65                  70                  75                  80

Trp Gln Lys Ile Ser Asp Pro Lys Ser Ile Gln Asp Ile Leu Lys Gln
                 85                  90                  95

Val Tyr Ala Asp His Ser Thr Asn Val Asp Lys Val Phe Ser Arg Ile
                100                 105                 110

Val Glu Ile Thr Gln His Pro Ala Ala Ala Ser Phe Ala Ser Ile
            115                 120                 125

Met Phe Ala Pro Arg Gly Gln Ile Ser Phe Gln
        130                 135
```

<210> SEQ ID NO 58
<211> LENGTH: 139
<212> TYPE: PRT
<213> ORGANISM: Physcomitrella patens
<220> FEATURE:
<223> OTHER INFORMATION: subsp. patens

<400> SEQUENCE: 58

```
Phe Ile Glu Lys Val Ile Gly Gly Pro Val Tyr Ile Val Gly Asn Ser
 1               5                  10                  15

Leu Gly Gly Tyr Val Gly Ser Tyr Phe Ala Ala Thr Asn Pro Glu Leu
             20                  25                  30

Val Lys Gly Val Thr Leu Leu Asn Ala Thr Pro Phe Trp Ala Phe Thr
             35                  40                  45

Pro Asn Ser Arg Arg Tyr Pro Leu Leu Ser Lys Leu Thr Pro Trp Gly
         50                  55                  60

Gly Leu Leu Pro Val Pro Ile Phe Ala Lys Ala Ile Arg Phe Trp
 65                  70                  75                  80

Trp Asp Leu Leu Arg Asn Pro Ser Thr Ile Arg Asn Met Leu Gly Ala
                 85                  90                  95

Val Tyr Ala Asn Arg Ser Ala Ile Asn Lys Lys Leu Ile Thr Gln Ile
                100                 105                 110

Ile Glu Ala Thr Asp His Pro Ala Ala Phe Ala Ala Phe Ala Ser Ile
            115                 120                 125

Val Phe Ala Pro Arg Ala His Thr Asp Phe Gly
        130                 135
```

<210> SEQ ID NO 59
<211> LENGTH: 139
<212> TYPE: PRT
<213> ORGANISM: Nicotiana tabacum

<400> SEQUENCE: 59

```
Phe Ile Glu Glu Val Ile Lys Glu Pro Val Tyr Ile Val Gly Asn Ser
 1               5                  10                  15

Leu Gly Gly Tyr Val Ala Leu Tyr Leu Ala Ala Tyr Tyr Pro Gln Leu
             20                  25                  30

Val Lys Gly Val Thr Leu Leu Asn Ala Thr Pro Phe Trp Gly Phe Leu
             35                  40                  45

Pro Asn Pro Val Arg Ser Pro Arg Leu Ser Arg Leu Phe Pro Trp Ala
         50                  55                  60
```

Gly Thr Phe Pro Leu Pro Asp Thr Ile Arg Lys Leu Thr Glu Leu Val
65                  70                  75                  80

Trp Gln Lys Ile Ser Ala Pro Glu Ser Ile Ala Glu Val Leu Lys Gln
                85                  90                  95

Val Tyr Ala Asp His Thr Thr Lys Val Asp Lys Val Phe Ser Ser Ile
            100                 105                 110

Leu Glu Val Thr Glu His Pro Ala Ala Ala Ser Leu Ala Ser Ile
        115                 120                 125

Leu Phe Ala Pro Arg Gly Gln Leu Ser Phe Lys
    130                 135

<210> SEQ ID NO 60
<211> LENGTH: 139
<212> TYPE: PRT
<213> ORGANISM: Vitis vinifera

<400> SEQUENCE: 60

Phe Ile Glu Gln Val Ile Gly Glu Pro Val Tyr Ile Val Gly Asn Ser
1               5                   10                  15

Leu Gly Gly Phe Val Ala Leu Tyr Phe Ala Ala Cys Asn Pro Gln Leu
            20                  25                  30

Val Lys Gly Val Thr Leu Leu Asn Ala Thr Pro Phe Trp Gly Phe Leu
        35                  40                  45

Pro Asn Pro Ser Arg Ser Pro Ser Leu Ala Arg Ile Phe Pro Trp Ala
    50                  55                  60

Gly Thr Phe Pro Leu Pro Ala Phe Val Arg Lys Leu Thr Glu Phe Val
65                  70                  75                  80

Trp Gln Lys Ile Ser Asp Pro Arg Ser Ile Gly Val Leu Lys Gln
                85                  90                  95

Val Tyr Ala Asp His Ser Thr Lys Val Asp Lys Val Phe Ser Arg Ile
            100                 105                 110

Leu Glu Thr Thr Gln His Pro Ala Ala Ala Ser Phe Ala Ser Ile
        115                 120                 125

Met Phe Ala Pro Gln Gly Gln Leu Ser Phe Ser
    130                 135

<210> SEQ ID NO 61
<211> LENGTH: 139
<212> TYPE: PRT
<213> ORGANISM: Populus trichocarpa

<400> SEQUENCE: 61

Phe Ile Glu Glu Val Ile Gly Glu Pro Val Tyr Ile Val Gly Asn Ser
1               5                   10                  15

Leu Gly Gly Phe Val Ala Leu Tyr Phe Ala Ala Arg Tyr Pro His Leu
            20                  25                  30

Val Lys Gly Val Thr Leu Leu Asn Ala Thr Pro Phe Trp Gly Phe Leu
        35                  40                  45

Pro Asn Pro Ile Arg Ser Pro Arg Leu Ala Arg Ile Phe Pro Trp Ser
    50                  55                  60

Gly Thr Phe Pro Leu Pro Ala Asn Val Arg Lys Leu Ile Ala Phe Phe
65                  70                  75                  80

Trp Gln Lys Ile Ser Asp Pro Lys Ser Ile Ala Glu Ile Leu Lys Gln
                85                  90                  95

Val Tyr Thr Asp His Ser Thr Asn Ile Asp Lys Val Phe Ser Arg Ile
            100                 105                 110

```
Leu Glu Ile Thr Gln His Pro Ala Ala Ala Ser Phe Ala Ser Ile
    115                 120                 125

Met Phe Ala Pro Gln Gly Gln Leu Ser Phe Arg
    130                 135

<210> SEQ ID NO 62
<211> LENGTH: 139
<212> TYPE: PRT
<213> ORGANISM: Ricinus communis

<400> SEQUENCE: 62

Phe Ile Glu Glu Val Ile Gly Glu Pro Val Tyr Val Gly Asn Ser
1               5                   10                  15

Leu Gly Gly Phe Val Ala Ile Tyr Phe Ala Ala Ser Asn Pro Gln Leu
            20                  25                  30

Val Lys Gly Val Thr Leu Leu Asn Ala Thr Pro Phe Trp Gly Phe Leu
        35                  40                  45

Pro Asn Pro Ile Arg Ser Pro Arg Leu Ala Arg Ile Ile Pro Trp Ser
    50                  55                  60

Gly Thr Phe Pro Leu Pro Ala Ser Val Arg Lys Leu Thr Glu Phe Phe
65                  70                  75                  80

Trp Gln Lys Ile Ser Asp Pro Lys Ser Ile Ala Gln Val Leu Lys Gln
                85                  90                  95

Val Tyr Ala Asp His Ser Thr Asn Val Asp Gln Val Phe Ser Arg Ile
            100                 105                 110

Leu Lys Ile Thr Gln His Pro Ala Ala Ala Ser Phe Ala Ser Ile
        115                 120                 125

Met Phe Ala Pro Gln Gly Gln Leu Ser Phe Arg
    130                 135

<210> SEQ ID NO 63
<211> LENGTH: 139
<212> TYPE: PRT
<213> ORGANISM: Arabidopsis thaliana

<400> SEQUENCE: 63

Ala Leu Ser Arg Cys Lys Glu Asn Asn Val Gln Ile Cys Leu Met Tyr
1               5                   10                  15

Gly Arg Glu Asp Pro Trp Val Arg Pro Leu Trp Gly Lys Lys Ile Lys
            20                  25                  30

Lys Glu Ile Pro Asn Ala Pro Tyr Tyr Glu Ile Ser Pro Ala Gly His
        35                  40                  45

Cys Pro His Asp Glu Val Pro Glu Val Val Asn Tyr Leu Met Arg Gly
    50                  55                  60

Trp Ile Lys His Leu Glu Ser Gly Gly Phe Glu Ala Leu Pro Leu Leu
65                  70                  75                  80

Glu Asp Thr Glu Glu Asp Trp Glu Glu Ser Arg Ile Gly Arg Glu Ile
                85                  90                  95

Glu Phe Pro Arg Asp Gly Trp Lys Lys Ala Val Asn Leu Trp Leu Tyr
            100                 105                 110

Gly Ser Asn Tyr Thr Tyr Trp Arg Gly Val Arg Glu Ser Phe Arg Ser
        115                 120                 125

Ser Phe Ile Arg Val Phe Gly Gly Lys Ser Ala
    130                 135

<210> SEQ ID NO 64
<211> LENGTH: 133
```

```
<212> TYPE: PRT
<213> ORGANISM: Oryza sativa

<400> SEQUENCE: 64

Ala Leu Ser Arg Cys Gln Arg Gln Gly Ile Pro Ile Ser Leu Met Tyr
1               5                   10                  15

Gly Arg Glu Asp Pro Trp Val Arg Pro Ile Trp Gly Ile Lys Val Lys
            20                  25                  30

Gln Gln Val Pro Glu Ser Pro Tyr Tyr Glu Ile Ser Pro Ala Gly His
        35                  40                  45

Cys Pro His Asp Glu Val Pro Glu Val Ile Asn Tyr Leu Leu Arg Gly
    50                  55                  60

Trp Leu Lys Asn Val Glu Ser Glu Gly Ser Val Gly Val Pro Phe Leu
65                  70                  75                  80

Glu Glu Pro Ser Tyr Ala Glu Asn Gly Val Ser Arg Glu Leu Glu Phe
                85                  90                  95

Val Arg Gly Gly Ser Lys Lys Ser Val His Val Arg Leu Phe Gly Ser
            100                 105                 110

Lys Ile Ser Leu Trp Ser Gln Leu Arg Ser Leu Leu Lys Ser Asn Thr
        115                 120                 125

Arg Val Ile Ser Arg
    130

<210> SEQ ID NO 65
<211> LENGTH: 133
<212> TYPE: PRT
<213> ORGANISM: Oryza sativa

<400> SEQUENCE: 65

Ala Leu Ser Arg Cys Gln Arg Gln Gly Ile Pro Ile Ser Leu Met Tyr
1               5                   10                  15

Gly Arg Glu Asp Pro Trp Val Arg Pro Ile Trp Gly Ile Lys Val Lys
            20                  25                  30

Gln Gln Val Pro Glu Ser Pro Tyr Tyr Glu Ile Ser Pro Ala Gly His
        35                  40                  45

Cys Pro His Asp Glu Val Pro Glu Val Ile Asn Tyr Leu Leu Arg Gly
    50                  55                  60

Trp Leu Lys Asn Val Glu Ser Glu Gly Ser Val Ala Val Pro Phe Leu
65                  70                  75                  80

Glu Glu Pro Ser Tyr Ala Glu Asn Gly Val Ser Arg Glu Leu Glu Phe
                85                  90                  95

Val Arg Gly Gly Ser Lys Lys Ser Val His Val Arg Leu Phe Gly Ser
            100                 105                 110

Lys Ile Ser Leu Trp Ser Gln Leu Arg Ser Leu Leu Lys Ser Asn Thr
        115                 120                 125

Trp Val Ile Ser Arg
    130

<210> SEQ ID NO 66
<211> LENGTH: 73
<212> TYPE: PRT
<213> ORGANISM: Oryza sativa

<400> SEQUENCE: 66

Ala Leu Ser Arg Cys Gln Arg Gln Gly Ile Pro Ile Ser Leu Met Tyr
1               5                   10                  15

Gly Arg Glu Asp Pro Trp Val Arg Pro Ile Trp Gly Ile Lys Val Lys
```

```
            20                  25                  30
Gln Gln Val Pro Glu Ser Pro Tyr Tyr Glu Ile Ser Pro Ala Gly His
        35                  40                  45

Cys Pro His Asp Glu Val Pro Glu Val Pro Gly Lys Ser Leu Ala Trp
    50                  55                  60

Trp Ile Thr Gly Arg Leu Gln Ala Ser
65                  70

<210> SEQ ID NO 67
<211> LENGTH: 136
<212> TYPE: PRT
<213> ORGANISM: Zea mays

<400> SEQUENCE: 67

Ala Ile Ser Arg Cys Gln Asp Gln Gly Ile Pro Ile Ser Leu Met Tyr
1               5                   10                  15

Gly Arg Glu Asp Pro Trp Ile Arg Pro Ile Trp Gly Leu Lys Val Lys
            20                  25                  30

Gln Gln Val Pro Glu Ala Pro Tyr Tyr Glu Ile Ser Pro Ala Gly His
        35                  40                  45

Cys Pro His Asp Glu Val Pro Glu Val Ile Asn Tyr Leu Leu Arg Gly
    50                  55                  60

Trp Leu Lys Asn Leu Glu Ser Glu Gly Ser Val Asp Leu Pro Phe Leu
65                  70                  75                  80

Glu Glu Arg Ser Tyr Ala Glu Arg Gly Val Ser Arg Glu Leu Glu Phe
                85                  90                  95

Val Arg Glu Gly Ser Arg Lys Ser Val Ser Val Arg Leu Tyr Gly Thr
            100                 105                 110

Lys Ile Ser Leu Trp Ser Gln Leu Ser Ser Phe Leu Asn Thr Arg Val
        115                 120                 125

Pro Lys Ser Arg Ile Val Leu Arg
    130                 135

<210> SEQ ID NO 68
<211> LENGTH: 83
<212> TYPE: PRT
<213> ORGANISM: Physcomitrella patens
<220> FEATURE:
<223> OTHER INFORMATION: subsp. patens

<400> SEQUENCE: 68

Asn Leu Ile Ser Leu Lys Glu Arg Arg Met Pro Met Cys Met Ile Tyr
1               5                   10                  15

Gly Lys Glu Asp Pro Trp Val Val Pro Phe Trp Gly Gln Arg Ala Lys
            20                  25                  30

Gln Arg Asn Pro Asp Ala Ile Tyr Tyr Glu Leu Ser Pro Ala Gly His
        35                  40                  45

Cys Pro His His Glu Ala Pro Glu Val Leu Phe Pro Ala Gln Ile Val
    50                  55                  60

Leu Leu Ala Cys Met Val Gln Asn Ile Ile Gly Lys Ala Arg Pro Leu
65                  70                  75                  80

Phe Lys Gly

<210> SEQ ID NO 69
<211> LENGTH: 135
<212> TYPE: PRT
<213> ORGANISM: Nicotiana tabacum
```

-continued

<400> SEQUENCE: 69

Ala Leu Thr Gly Cys Arg Met Asn Asn Val Pro Val Cys Leu Met Tyr
1               5                   10                  15

Gly Lys Glu Asp Pro Trp Val Met Pro Phe Trp Ala Leu Gln Val Lys
            20                  25                  30

Arg Gln Leu Pro Glu Ala Pro Tyr Tyr Gln Ile Ser Pro Ala Gly His
        35                  40                  45

Cys Pro His Asp Glu Val Pro Glu Ile Val Asn Phe Leu Leu Arg Gly
    50                  55                  60

Trp Ile Lys Asn Ile Glu Ser His Ser Ser Val Ala Leu Pro Leu Leu
65                  70                  75                  80

Asp Ser Pro Glu Ser Ile Glu Tyr Asp Ile Val Arg Asp Leu Glu Phe
                85                  90                  95

Val Arg Gln Gly Met Lys Lys Ser Val Arg Val Gln Phe Tyr Gly Ser
            100                 105                 110

Met Thr Ser Gln Trp Glu Lys Leu Gly Met Phe Leu Lys Ser Arg Phe
        115                 120                 125

Gln Tyr Gly Val Tyr Ser Pro
130                 135

<210> SEQ ID NO 70
<211> LENGTH: 136
<212> TYPE: PRT
<213> ORGANISM: Vitis vinifera

<400> SEQUENCE: 70

Ala Leu Ser Arg Cys Gln Met Ser Asn Val Pro Ile Cys Leu Met Tyr
1               5                   10                  15

Gly Lys Glu Asp Pro Trp Val Arg Pro Val Trp Gly Leu Gln Val Lys
            20                  25                  30

Arg Gln Leu Leu Glu Ala Pro Tyr Tyr Glu Ile Ser Pro Ala Gly His
        35                  40                  45

Cys Pro His Asp Glu Val Pro Glu Val Val Asn Tyr Leu Leu Arg Gly
    50                  55                  60

Trp Ile Gly Asn Leu Glu Ser Lys Gly Ser Val Thr Leu Pro Leu Leu
65                  70                  75                  80

Asp Asp Pro Glu Asn Ile Gln Tyr Gly Thr Thr Lys Asp Leu Glu Phe
                85                  90                  95

Val Arg Glu Gly Ser Lys Lys Ser Val Arg Val His Phe Tyr Gly Ser
            100                 105                 110

Arg Phe Ser Leu Trp Asn Arg Ile Arg Ser Tyr Val Lys Ser Arg Phe
        115                 120                 125

Glu Ala Leu Glu Ile Asn Ser Arg
130                 135

<210> SEQ ID NO 71
<211> LENGTH: 137
<212> TYPE: PRT
<213> ORGANISM: Populus trichocarpa

<400> SEQUENCE: 71

Thr Leu Ala Arg Cys Lys Met Ser Asp Thr Pro Ile Cys Leu Val Tyr
1               5                   10                  15

Gly Lys Glu Asp Pro Trp Val Lys Pro Val Trp Gly Leu Gln Val Lys
            20                  25                  30

Gln Gln Val Pro Glu Ala Pro Tyr Tyr Glu Ile Ser Pro Ala Gly His

```
            35                  40                  45
Cys Pro His Asp Glu Val Pro Glu Ala Val Asn Tyr Leu Leu Arg Gly
     50                  55                  60
Trp Ile Lys Asn Leu Glu Ser His Gly Ser Val Ala Leu Pro Leu His
 65                  70                  75                  80
Glu Asp Ala Glu Val Glu Asn Ser Phe Ala Met Asp Leu Glu Phe
                 85                  90                  95
Val Arg Glu Gly Ser Arg Lys Ser Val Ile Val Arg Phe Phe Gly Ser
                100                 105                 110
Arg Phe Ser Ile Trp Asn Ser Phe Ser Tyr Ile Lys Ser Gln Phe
                115                 120                 125
Lys Glu Thr Thr Ser Arg Ile Leu Thr
                130                 135

<210> SEQ ID NO 72
<211> LENGTH: 75
<212> TYPE: PRT
<213> ORGANISM: Ricinus communis

<400> SEQUENCE: 72

Cys Leu Met Arg Cys Lys Met Asn Asn Leu Pro Ile Cys Leu Leu Tyr
  1               5                  10                  15
Gly Arg Glu Asp Pro Trp Val Lys Pro Ile Trp Gly Leu Gln Val Lys
                 20                  25                  30
Arg Gln Val Pro Glu Ala Ser Tyr Tyr Glu Ile Ser Pro Ala Gly His
                 35                  40                  45
Cys Pro His Asp Glu Val Pro Glu Val Cys Ser Leu Ser Leu Phe Leu
     50                  55                  60
Val Gly Ile Pro Leu Leu Phe Leu Val Ile Leu
 65                  70                  75

<210> SEQ ID NO 73
<211> LENGTH: 414
<212> TYPE: PRT
<213> ORGANISM: Arabidopsis thaliana

<400> SEQUENCE: 73

Glu Ser Thr Ser Lys Val Leu Ile Pro Gly Leu Pro Asp Glu Ser Asn
  1               5                  10                  15
Gly Glu Ile Ala Ala Arg Ile Ser His Ser His Cys Glu Trp Lys Pro
                 20                  25                  30
Lys Leu Arg Val His Tyr Glu Lys Ala Gly Cys Asp Asn Leu Asp Ala
                 35                  40                  45
Pro Ala Val Leu Phe Leu Pro Gly Phe Gly Val Gly Ser Phe His Tyr
     50                  55                  60
Glu Lys Gln Leu Thr Asp Leu Gly Arg Asp Tyr Arg Val Trp Ala Ile
 65                  70                  75                  80
Asp Phe Leu Gly Gln Gly Leu Ser Leu Pro Thr Glu Pro Thr Thr
                 85                  90                  95
Met Thr Glu Glu Thr Ser Ser Glu Asp Lys Glu Pro Phe Trp Gly
                100                 105                 110
Phe Gly Asp Lys Thr Glu Pro Trp Ala Asp Gln Leu Val Phe Ser Leu
                115                 120                 125
Asp Leu Trp Arg Asp Gln Val Gln Phe Val Glu Glu Val Ile Gly Glu
                130                 135                 140
Pro Val Tyr Ile Ala Gly Asn Ser Leu Gly Gly Tyr Val Ala Leu Tyr
```

```
                145                 150                 155                 160
            Phe Ala Ala Thr His Pro His Leu Val Lys Gly Val Thr Leu Leu Asn
                            165                 170                 175
            Ala Thr Pro Phe Trp Gly Phe Phe Pro Asn Pro Val Arg Ser Pro Lys
                            180                 185                 190
            Leu Ala Arg Leu Phe Pro Trp Pro Gly Ala Phe Pro Leu Pro Glu Arg
                            195                 200                 205
            Val Lys Lys Ile Thr Glu Leu Val Trp Gln Lys Ile Ser Asp Pro Glu
                210                 215                 220
            Ser Ile Ala Glu Ile Leu Lys Gln Val Tyr Thr Asp His Ser Ile Asn
            225                 230                 235                 240
            Val Asp Lys Val Phe Ser Arg Ile Val Glu Val Thr Gln His Pro Ala
                            245                 250                 255
            Ala Ala Ala Ser Phe Ala Ser Ile Met Leu Ala Pro Gly Gly Glu Leu
                            260                 265                 270
            Ser Phe Ser Ala Leu Ser Arg Cys Lys Glu Asn Asn Val Gln Ile Cys
                            275                 280                 285
            Leu Met Tyr Gly Arg Glu Asp Pro Trp Val Arg Pro Leu Trp Gly Lys
                290                 295                 300
            Lys Ile Lys Lys Glu Ile Pro Asn Ala Pro Tyr Tyr Glu Ile Ser Pro
            305                 310                 315                 320
            Ala Gly His Cys Pro His Asp Glu Val Pro Glu Val Val Asn Tyr Leu
                            325                 330                 335
            Met Arg Gly Trp Ile Lys His Leu Glu Ser Gly Gly Phe Glu Ala Leu
                            340                 345                 350
            Pro Leu Leu Glu Asp Thr Glu Glu Asp Trp Glu Glu Ser Arg Ile Gly
                            355                 360                 365
            Arg Glu Ile Glu Phe Pro Arg Asp Gly Trp Lys Lys Ala Val Asn Leu
                            370                 375                 380
            Trp Leu Tyr Gly Ser Asn Tyr Thr Tyr Trp Arg Gly Val Arg Glu Ser
            385                 390                 395                 400
            Phe Arg Ser Ser Phe Ile Arg Val Phe Gly Gly Lys Ser Ala
                            405                 410

<210> SEQ ID NO 74
<211> LENGTH: 403
<212> TYPE: PRT
<213> ORGANISM: Oryza sativa

<400> SEQUENCE: 74

Gly Glu Ile Glu Lys Met Ile Ile Pro Ser Leu Pro Glu Gly Pro Glu
1               5                   10                  15
Ser Ser Leu Ile Ser Thr Gly Phe Trp Glu Trp Lys Pro Lys Leu Ser
                20                  25                  30
Val Tyr Tyr Glu Lys Ser Gly Ile Asp Asn Ser Lys Ala Pro Ser Val
                35                  40                  45
Leu Phe Leu Pro Gly Phe Gly Val Gly Thr Phe His Phe Glu Lys Gln
            50                  55                  60
Leu Lys Asp Leu Gly Arg Asp Tyr Lys Val Trp Thr Met Asp Phe Leu
65                  70                  75                  80
Gly Gln Gly Met Ser Leu Pro Cys Glu Asp Pro Ala Pro Lys Ser Thr
                85                  90                  95
Ser Gly Glu Leu Asp Glu Asp Thr Tyr Trp Gly Phe Gln Glu Leu
                100                 105                 110
```

```
Gln Pro Trp Ala Glu Glu Leu Val Tyr Ser Ile Asp Leu Trp Arg Asp
            115                 120                 125

Gln Val Gln Phe Ile Glu Glu Val Ile Gly Glu Pro Val Tyr Ile Val
            130                 135                 140

Gly Asn Ser Leu Gly Gly Phe Val Ser Leu Tyr Leu Ala Ala Ser Cys
145                 150                 155                 160

Pro His Leu Val Lys Gly Val Thr Leu Leu Asn Ala Thr Pro Phe Trp
                165                 170                 175

Gly Phe Leu Pro Asn Pro Ala Thr Ser Pro Arg Leu Ser Lys Ile Phe
            180                 185                 190

Pro Trp Ala Gly Thr Phe Pro Leu Pro Ser Phe Val Arg Lys Leu Thr
            195                 200                 205

Glu Thr Val Trp Gln Lys Ile Ser Asp Pro Arg Ser Ile Gln Gly Ile
            210                 215                 220

Leu Lys Gln Val Tyr Ala Asp His Ser Thr Asn Val Asp Met Val Phe
225                 230                 235                 240

Ser Arg Ile Ile Glu Thr Thr Gln His Pro Ala Ala Ala Ser Phe
                245                 250                 255

Ala Ser Ile Met Cys Ala Pro Lys Gly Gln Ile Ser Phe Glu Ala Leu
            260                 265                 270

Ser Arg Cys Gln Arg Gln Gly Ile Pro Ile Ser Leu Met Tyr Gly Arg
            275                 280                 285

Glu Asp Pro Trp Val Arg Pro Ile Trp Gly Ile Lys Val Lys Gln Gln
            290                 295                 300

Val Pro Glu Ser Pro Tyr Tyr Glu Ile Ser Pro Ala Gly His Cys Pro
305                 310                 315                 320

His Asp Glu Val Pro Glu Val Ile Asn Tyr Leu Leu Arg Gly Trp Leu
                325                 330                 335

Lys Asn Val Glu Ser Glu Gly Ser Val Gly Val Pro Phe Leu Glu Glu
            340                 345                 350

Pro Ser Tyr Ala Glu Asn Gly Val Ser Arg Glu Leu Glu Phe Val Arg
            355                 360                 365

Gly Gly Ser Lys Lys Ser Val His Val Arg Leu Phe Gly Ser Lys Ile
            370                 375                 380

Ser Leu Trp Ser Gln Leu Arg Ser Leu Leu Lys Ser Asn Thr Arg Val
385                 390                 395                 400

Ile Ser Arg

<210> SEQ ID NO 75
<211> LENGTH: 402
<212> TYPE: PRT
<213> ORGANISM: Oryza sativa

<400> SEQUENCE: 75

Gly Glu Ile Glu Lys Met Ile Ile Pro Ser Leu Pro Glu Gly Pro Glu
1               5                   10                  15

Ser Ser Leu Ile Ser Thr Gly Phe Trp Glu Trp Pro Lys Leu Ser Val
            20                  25                  30

Tyr Tyr Glu Lys Ser Gly Ile Asp Asn Ser Lys Ala Pro Ser Val Leu
            35                  40                  45

Phe Leu Pro Gly Phe Gly Val Gly Thr Phe His Phe Glu Lys Gln Leu
    50                  55                  60

Lys Asp Leu Gly Arg Asp Tyr Lys Val Trp Thr Met Asp Phe Leu Gly
65                  70                  75                  80
```

```
Gln Gly Met Ser Leu Pro Cys Glu Asp Pro Ala Pro Lys Ser Thr Ser
                85                  90                  95

Gly Glu Leu Asp Glu Asp Thr Tyr Trp Gly Phe Gly Gln Glu Leu Gln
            100                 105                 110

Pro Trp Ala Glu Glu Leu Val Tyr Ser Ile Asp Leu Trp Arg Asp Gln
        115                 120                 125

Val Gln Phe Ile Glu Glu Val Ile Gly Glu Pro Val Tyr Ile Val Gly
    130                 135                 140

Asn Ser Leu Gly Gly Phe Val Ser Leu Tyr Leu Ala Ala Ser Cys Pro
145                 150                 155                 160

His Leu Val Lys Gly Val Thr Leu Leu Asn Ala Thr Pro Phe Trp Gly
                165                 170                 175

Phe Leu Pro Asn Pro Ala Thr Ser Pro Arg Leu Ser Lys Ile Phe Pro
            180                 185                 190

Trp Ala Gly Thr Phe Pro Leu Pro Ser Phe Val Arg Lys Leu Thr Glu
        195                 200                 205

Thr Val Trp Gln Lys Ile Ser Asp Pro Arg Ser Ile Gln Gly Ile Leu
    210                 215                 220

Lys Gln Val Tyr Ala Asp His Ser Thr Asn Val Asp Met Val Phe Ser
225                 230                 235                 240

Arg Ile Ile Glu Thr Thr Gln His Pro Ala Ala Ala Ser Phe Ala
                245                 250                 255

Ser Ile Met Cys Ala Pro Lys Gly Gln Ile Ser Phe Glu Ala Leu Ser
            260                 265                 270

Arg Cys Gln Arg Gln Gly Ile Pro Ile Ser Leu Met Tyr Gly Arg Glu
        275                 280                 285

Asp Pro Trp Val Arg Pro Ile Trp Gly Ile Lys Val Lys Gln Gln Val
    290                 295                 300

Pro Glu Ser Pro Tyr Tyr Glu Ile Ser Pro Ala Gly His Cys Pro His
305                 310                 315                 320

Asp Glu Val Pro Glu Val Ile Asn Tyr Leu Leu Arg Gly Trp Leu Lys
                325                 330                 335

Asn Val Glu Ser Glu Gly Ser Val Ala Val Pro Phe Leu Glu Glu Pro
            340                 345                 350

Ser Tyr Ala Glu Asn Gly Val Ser Arg Glu Leu Glu Phe Val Arg Gly
        355                 360                 365

Gly Ser Lys Lys Ser Val His Val Arg Leu Phe Gly Ser Lys Ile Ser
    370                 375                 380

Leu Trp Ser Gln Leu Arg Ser Leu Leu Lys Ser Asn Thr Trp Val Ile
385                 390                 395                 400

Ser Arg

<210> SEQ ID NO 76
<211> LENGTH: 343
<212> TYPE: PRT
<213> ORGANISM: Oryza sativa

<400> SEQUENCE: 76

Gly Glu Ile Glu Lys Met Ile Ile Pro Ser Leu Pro Glu Gly Pro Glu
1               5                   10                  15

Ser Ser Leu Ile Ser Thr Gly Phe Trp Glu Trp Lys Pro Lys Leu Ser
            20                  25                  30

Val Tyr Tyr Glu Lys Ser Gly Ile Asp Asn Ser Lys Ala Pro Ser Val
        35                  40                  45
```

```
Leu Phe Leu Pro Gly Phe Gly Val Gly Thr Phe His Phe Glu Lys Gln
 50                  55                  60

Leu Lys Asp Leu Gly Arg Asp Tyr Lys Val Trp Thr Met Asp Phe Leu
 65                  70                  75                  80

Gly Gln Gly Met Ser Leu Pro Cys Glu Asp Pro Ala Pro Lys Ser Thr
                 85                  90                  95

Ser Gly Glu Leu Asp Glu Asp Thr Tyr Trp Gly Phe Gly Gln Glu Leu
            100                 105                 110

Gln Pro Trp Ala Glu Glu Leu Val Tyr Ser Ile Asp Leu Trp Arg Asp
            115                 120                 125

Gln Val Gln Phe Ile Glu Glu Val Ile Gly Pro Val Tyr Ile Val
130                 135                 140

Gly Asn Ser Leu Gly Gly Phe Val Ser Leu Tyr Leu Ala Ala Ser Cys
145                 150                 155                 160

Pro His Leu Val Lys Gly Val Thr Leu Leu Asn Ala Thr Pro Phe Trp
                165                 170                 175

Gly Phe Leu Pro Asn Pro Ala Thr Ser Pro Arg Leu Ser Lys Ile Phe
                180                 185                 190

Pro Trp Ala Gly Thr Phe Pro Leu Pro Ser Phe Val Arg Lys Leu Thr
            195                 200                 205

Glu Thr Val Trp Gln Lys Ile Ser Asp Pro Arg Ser Ile Gln Gly Ile
210                 215                 220

Leu Lys Gln Val Tyr Ala Asp His Ser Thr Asn Val Asp Met Val Phe
225                 230                 235                 240

Ser Arg Ile Ile Glu Thr Thr Gln His Pro Ala Ala Ala Ala Ser Phe
                245                 250                 255

Ala Ser Ile Met Cys Ala Pro Lys Gly Gln Ile Ser Phe Glu Ala Leu
            260                 265                 270

Ser Arg Cys Gln Arg Gln Gly Ile Pro Ile Ser Leu Met Tyr Gly Arg
            275                 280                 285

Glu Asp Pro Trp Val Arg Pro Ile Trp Gly Ile Lys Val Lys Gln Gln
290                 295                 300

Val Pro Glu Ser Pro Tyr Tyr Glu Ile Ser Pro Ala Gly His Cys Pro
305                 310                 315                 320

His Asp Glu Val Pro Glu Val Pro Gly Lys Ser Leu Ala Trp Trp Ile
                325                 330                 335

Thr Gly Arg Leu Gln Ala Ser
            340

<210> SEQ ID NO 77
<211> LENGTH: 403
<212> TYPE: PRT
<213> ORGANISM: Zea mays

<400> SEQUENCE: 77

Gly Glu Ala Glu Arg Val Met Ile Gln Gly Leu Pro Glu Gly Pro Asp
1               5                  10                  15

Ser Ser Pro Ile Ser Thr Gly Phe Trp Glu Trp Lys Pro Lys Leu Thr
                20                  25                  30

Val His Tyr Glu Arg Ser Gly Met Lys Asn Ser Lys Ala Pro Ala Val
            35                  40                  45

Leu Phe Leu Pro Gly Phe Gly Val Gly Thr Phe His Phe Glu Lys Gln
 50                  55                  60

Leu Arg Asp Leu Gly Arg Asp His Arg Val Trp Thr Met Asp Phe Leu
 65                  70                  75                  80
```

Gly Gln Gly Met Ser Leu Pro Gly Glu Asp Pro Ala Pro Ser Ser Ile
                85                  90                  95

Ala Ser Glu Asp Ala Phe Trp Gly Phe Gly Gln Asp Ser Gln Pro Trp
            100                 105                 110

Ala Glu Glu Leu Val Tyr Ser Val Asp Leu Trp Gln Asn Gln Val Gln
        115                 120                 125

Phe Ile Glu Glu Val Ile Arg Glu Pro Val Tyr Ile Val Gly Asn Ser
    130                 135                 140

Leu Gly Gly Phe Val Ala Leu Tyr Phe Ala Ala Ser Ser Pro His Leu
145                 150                 155                 160

Val Lys Gly Val Thr Leu Leu Asn Ala Thr Pro Phe Trp Gly Phe Phe
                165                 170                 175

Pro Asn Pro Ala Thr Ser Pro Arg Leu Ser Lys Ile Phe Pro Trp Ala
            180                 185                 190

Gly Thr Phe Pro Leu Pro Ser Phe Val Arg Lys Ile Thr Glu Ala Val
        195                 200                 205

Trp Gln Lys Ile Ser Asp Pro Lys Ser Ile Gln Asp Ile Leu Lys Gln
    210                 215                 220

Val Tyr Ala Asp His Ser Thr Asn Val Asp Lys Val Phe Ser Arg Ile
225                 230                 235                 240

Val Glu Ile Thr Gln His Pro Ala Ala Ala Ser Phe Ala Ser Ile
                245                 250                 255

Met Phe Ala Pro Arg Gly Gln Ile Ser Phe Gln Ala Ile Ser Arg Cys
            260                 265                 270

Gln Asp Gln Gly Ile Pro Ile Ser Leu Met Tyr Gly Arg Glu Asp Pro
        275                 280                 285

Trp Ile Arg Pro Ile Trp Gly Leu Lys Val Lys Gln Gln Val Pro Glu
    290                 295                 300

Ala Pro Tyr Tyr Glu Ile Ser Pro Ala Gly His Cys Pro His Asp Glu
305                 310                 315                 320

Val Pro Glu Val Ile Asn Tyr Leu Leu Arg Gly Trp Leu Lys Asn Leu
                325                 330                 335

Glu Ser Glu Gly Ser Val Asp Leu Pro Phe Leu Glu Gly Arg Ser Tyr
            340                 345                 350

Ala Glu Arg Gly Val Ser Arg Glu Leu Glu Phe Val Arg Glu Gly Ser
        355                 360                 365

Arg Lys Ser Val Ser Val Arg Leu Tyr Gly Thr Lys Ile Ser Leu Trp
    370                 375                 380

Ser Gln Leu Ser Ser Phe Leu Asn Thr Arg Val Pro Lys Ser Arg Ile
385                 390                 395                 400

Val Leu Arg

<210> SEQ ID NO 78
<211> LENGTH: 335
<212> TYPE: PRT
<213> ORGANISM: Physcomitrella patens
<220> FEATURE:
<223> OTHER INFORMATION: subsp. patens

<400> SEQUENCE: 78

Ile Ala Ser His Ile Trp Glu Trp Arg His Arg Trp Asn Ile His Tyr
1               5                   10                  15

Glu Cys Ala Gly Thr Ser Leu Asn Thr Asn Ala Pro Ala Met Leu Leu
            20                  25                  30

Leu Pro Gly Phe Gly Val Gly Ser Phe His Tyr His Gln Gln Leu Arg
            35                  40                  45

Asp Leu Gly Gln Glu Tyr Arg Val Trp Ala Ile Asp Phe Leu Gly Gln
 50                  55                  60

Gly Lys Ser Trp Pro Ser His Asp Pro Ala Pro Glu Glu Ala Glu Glu
 65                  70                  75                  80

Val Val Glu Glu Ile Arg His Trp Ser Leu Gly Lys Asn Pro Glu Pro
                 85                  90                  95

Trp Ala Glu Gly Leu Val Tyr Ser Val Asp Thr Trp Arg Asp Gln Val
            100                 105                 110

His Phe Ile Glu Lys Val Ile Gly Gly Pro Val Tyr Ile Val Gly Asn
        115                 120                 125

Ser Leu Gly Gly Tyr Val Gly Ser Tyr Phe Ala Ala Thr Asn Pro Glu
130                 135                 140

Leu Val Lys Gly Val Thr Leu Leu Asn Ala Thr Pro Phe Trp Ala Phe
145                 150                 155                 160

Thr Pro Asn Ser Arg Arg Tyr Pro Leu Leu Ser Lys Leu Thr Pro Trp
                165                 170                 175

Gly Gly Leu Leu Pro Val Pro Ile Phe Ala Lys Ala Ile Ile Arg Phe
            180                 185                 190

Trp Trp Asp Leu Leu Arg Asn Pro Ser Thr Ile Arg Asn Met Leu Gly
        195                 200                 205

Ala Val Tyr Ala Asn Arg Ser Ala Ile Asn Lys Lys Leu Ile Thr Gln
    210                 215                 220

Ile Ile Glu Ala Thr Asp His Pro Ala Ala Phe Ala Ala Phe Ala Ser
225                 230                 235                 240

Ile Val Phe Ala Pro Arg Ala His Thr Asp Phe Gly Asn Leu Ile Ser
                245                 250                 255

Leu Lys Glu Arg Arg Met Pro Met Cys Met Ile Tyr Gly Lys Glu Asp
            260                 265                 270

Pro Trp Val Val Pro Phe Trp Gly Gln Arg Ala Lys Gln Arg Asn Pro
        275                 280                 285

Asp Ala Ile Tyr Tyr Glu Leu Ser Pro Ala Gly His Cys Pro His His
    290                 295                 300

Glu Ala Pro Glu Val Leu Phe Pro Ala Gln Ile Val Leu Leu Ala Cys
305                 310                 315                 320

Met Val Gln Asn Ile Ile Gly Lys Ala Arg Pro Leu Phe Lys Gly
                325                 330                 335

<210> SEQ ID NO 79
<211> LENGTH: 412
<212> TYPE: PRT
<213> ORGANISM: Nicotiana tabacum

<400> SEQUENCE: 79

Lys Ser Val Pro Lys Val Ile Val Pro Ser Leu Pro Asp Glu Thr Lys
 1               5                  10                  15

Ala Asp Ser Val Ala Val Asp Ser Cys Leu Trp Glu Trp Lys Pro
             20                  25                  30

Lys Leu Lys Val His Tyr Glu Lys Ser Gly Cys Gln Asn Val Asn Ser
         35                  40                  45

Ala Pro Ile Leu Phe Leu Pro Gly Phe Gly Val Gly Ser Phe His Tyr
     50                  55                  60

Glu Lys Gln Leu Lys Asp Leu Gly Cys Asp His Arg Ile Trp Ala Leu
 65                  70                  75                  80

```
Asp Phe Leu Gly Gln Gly Lys Ser Leu Pro Cys Glu Pro Thr Leu
                85                  90                  95

Gln Ser Lys Arg Leu Asp Glu Ser Glu Arg Asp Gly Asn Asn Ala Val
            100                 105                 110

Trp Gly Phe Gly Asp Glu Ala Glu Pro Trp Ala Lys Glu Leu Val Tyr
        115                 120                 125

Ser Val Asp Leu Trp Arg Asp Gln Val Arg Phe Ile Glu Glu Val Ile
    130                 135                 140

Lys Glu Pro Val Tyr Ile Val Gly Asn Ser Leu Gly Gly Tyr Val Ala
145                 150                 155                 160

Leu Tyr Leu Ala Ala Tyr Tyr Pro Gln Leu Val Lys Gly Val Thr Leu
                165                 170                 175

Leu Asn Ala Thr Pro Phe Trp Gly Phe Leu Pro Asn Pro Val Arg Ser
                180                 185                 190

Pro Arg Leu Ser Arg Leu Phe Pro Trp Ala Gly Thr Phe Pro Leu Pro
            195                 200                 205

Asp Thr Ile Arg Lys Leu Thr Glu Leu Val Trp Gln Lys Ile Ser Ala
        210                 215                 220

Pro Glu Ser Ile Ala Glu Val Leu Lys Gln Val Tyr Ala Asp His Thr
225                 230                 235                 240

Thr Lys Val Asp Lys Val Phe Ser Ser Ile Leu Glu Val Thr Glu His
                245                 250                 255

Pro Ala Ala Ala Ser Leu Ala Ser Ile Leu Phe Ala Pro Arg Gly
                260                 265                 270

Gln Leu Ser Phe Lys Ala Leu Thr Gly Cys Arg Met Asn Asn Val Pro
            275                 280                 285

Val Cys Leu Met Tyr Gly Lys Glu Asp Pro Trp Val Met Pro Phe Trp
        290                 295                 300

Ala Leu Gln Val Lys Arg Gln Leu Pro Glu Ala Pro Tyr Tyr Gln Ile
305                 310                 315                 320

Ser Pro Ala Gly His Cys Pro His Asp Glu Val Pro Glu Ile Val Asn
                325                 330                 335

Phe Leu Leu Arg Gly Trp Ile Lys Asn Ile Glu Ser His Ser Ser Val
                340                 345                 350

Ala Leu Pro Leu Leu Asp Ser Pro Glu Ser Ile Glu Tyr Asp Ile Val
            355                 360                 365

Arg Asp Leu Glu Phe Val Arg Gln Gly Met Lys Lys Ser Val Arg Val
        370                 375                 380

Gln Phe Tyr Gly Ser Met Thr Ser Gln Trp Glu Lys Leu Gly Met Phe
385                 390                 395                 400

Leu Lys Ser Arg Phe Gln Tyr Gly Val Tyr Ser Pro
                405                 410

<210> SEQ ID NO 80
<211> LENGTH: 412
<212> TYPE: PRT
<213> ORGANISM: Vitis vinifera

<400> SEQUENCE: 80

Asp Leu Ile Thr Gln Ile Leu Ile Pro Pro Gly Leu Pro Asp Asp Ser
1               5                   10                  15

Asn Asp Asp Ser Gly Ala Gln Ile Ser Ser Cys Phe Trp Glu Trp Lys
                20                  25                  30

Pro Lys Leu Thr Val His Tyr Glu Lys Ser Gly Cys Glu Asn Val Asn
```

35                  40                  45
Ser Pro Pro Val Leu Phe Leu Pro Gly Phe Gly Val Gly Ser Phe His
 50                  55                  60

Tyr Glu Lys Gln Leu Lys Asp Leu Gly Arg Asp Phe Arg Val Trp Ala
 65                  70                  75                  80

Val Asp Phe Leu Gly Gln Gly Met Ser Leu Pro Phe Glu Asp Pro Ala
                 85                  90                  95

Pro Gln Ser Lys Lys Glu Leu Asp Ser Glu Arg Asn Asp Phe Ser Trp
                100                 105                 110

Gly Phe Gly Asp Glu Thr Glu Pro Trp Ala Asn Glu Leu Val Tyr Ser
                115                 120                 125

Ile Asp Leu Trp Gln Asp Gln Val Arg Phe Ile Glu Gln Val Ile Gly
                130                 135                 140

Glu Pro Val Tyr Ile Val Gly Asn Ser Leu Gly Gly Phe Val Ala Leu
145                 150                 155                 160

Tyr Phe Ala Ala Cys Asn Pro Gln Leu Val Lys Gly Val Thr Leu Leu
                165                 170                 175

Asn Ala Thr Pro Phe Trp Gly Phe Leu Pro Asn Pro Ser Arg Ser Pro
                180                 185                 190

Ser Leu Ala Arg Ile Phe Pro Trp Ala Gly Thr Phe Pro Leu Pro Ala
                195                 200                 205

Phe Val Arg Lys Leu Thr Glu Phe Val Trp Gln Lys Ile Ser Asp Pro
210                 215                 220

Arg Ser Ile Gly Glu Val Leu Lys Gln Val Tyr Ala Asp His Ser Thr
225                 230                 235                 240

Lys Val Asp Lys Val Phe Ser Arg Ile Leu Glu Thr Thr Gln His Pro
                245                 250                 255

Ala Ala Ala Ala Ser Phe Ala Ser Ile Met Phe Ala Pro Gln Gly Gln
                260                 265                 270

Leu Ser Phe Ser Ala Leu Ser Arg Cys Gln Met Ser Asn Val Pro Ile
                275                 280                 285

Cys Leu Met Tyr Gly Lys Glu Asp Pro Trp Val Arg Pro Val Trp Gly
                290                 295                 300

Leu Gln Val Lys Arg Gln Leu Glu Ala Pro Tyr Tyr Glu Ile Ser
305                 310                 315                 320

Pro Ala Gly His Cys Pro His Asp Glu Val Pro Glu Val Val Asn Tyr
                325                 330                 335

Leu Leu Arg Gly Trp Ile Gly Asn Leu Glu Ser Lys Gly Ser Val Thr
                340                 345                 350

Leu Pro Leu Leu Asp Asp Pro Glu Asn Ile Gln Tyr Gly Thr Thr Lys
                355                 360                 365

Asp Leu Glu Phe Val Arg Gly Ser Lys Lys Ser Val Arg Val His
                370                 375                 380

Phe Tyr Gly Ser Arg Phe Ser Leu Trp Asn Arg Ile Arg Ser Tyr Val
385                 390                 395                 400

Lys Ser Arg Phe Glu Ala Leu Glu Ile Asn Ser Arg
                405                 410

<210> SEQ ID NO 81
<211> LENGTH: 412
<212> TYPE: PRT
<213> ORGANISM: Populus trichocarpa

<400> SEQUENCE: 81

```
Glu Ser Pro Thr Lys Val Leu Ile Pro Gly Leu Pro Asp Glu Ser Asn
1               5                   10                  15

Gly Glu Tyr Ser Ala Pro Val Ser Ser Cys Phe Trp Lys Trp Lys Pro
                20                  25                  30

Lys Leu Asn Val His Tyr Glu Lys Ala Gly Cys Glu Asn Val Asn Ser
                35                  40                  45

Pro Pro Val Leu Phe Leu Pro Gly Phe Gly Val Gly Ser Phe His Tyr
        50                  55                  60

Glu Lys Gln Leu Lys Asp Leu Gly Arg Asp Tyr Arg Val Trp Ala Ile
65                  70                  75                  80

Asp Phe Leu Gly Gln Gly Met Ser Leu Pro Val Glu Asn Pro Thr Leu
                85                  90                  95

Phe Ser Lys Asp Gly Ala Ala Ser Glu Gly Lys Asp Ser Ile Trp Gly
            100                 105                 110

Phe Gly Asp Glu Ile Glu Pro Trp Ala Asn Asp Leu Val Phe Ser Met
            115                 120                 125

Asp Leu Trp Gln Asp Gln Val His Phe Ile Glu Glu Val Ile Gly Glu
        130                 135                 140

Pro Val Tyr Ile Val Gly Asn Ser Leu Gly Gly Phe Val Ala Leu Tyr
145                 150                 155                 160

Phe Ala Ala Arg Tyr Pro His Leu Val Lys Gly Val Thr Leu Leu Asn
                165                 170                 175

Ala Thr Pro Phe Trp Gly Phe Leu Pro Asn Pro Ile Arg Ser Pro Arg
            180                 185                 190

Leu Ala Arg Ile Phe Pro Trp Ser Gly Thr Phe Pro Leu Pro Ala Asn
        195                 200                 205

Val Arg Lys Leu Ile Ala Phe Phe Trp Gln Lys Ile Ser Asp Pro Lys
210                 215                 220

Ser Ile Ala Glu Ile Leu Lys Gln Val Tyr Thr Asp His Ser Thr Asn
225                 230                 235                 240

Ile Asp Lys Val Phe Ser Arg Ile Leu Glu Ile Thr Gln His Pro Ala
            245                 250                 255

Ala Ala Ala Ser Phe Ala Ser Ile Met Phe Ala Pro Gln Gly Gln Leu
        260                 265                 270

Ser Phe Arg Thr Leu Ala Arg Cys Lys Met Ser Asp Thr Pro Ile Cys
    275                 280                 285

Leu Val Tyr Gly Lys Glu Asp Pro Trp Val Lys Pro Val Trp Gly Leu
        290                 295                 300

Gln Val Lys Gln Val Pro Glu Ala Pro Tyr Tyr Glu Ile Ser Pro
305                 310                 315                 320

Ala Gly His Cys Pro His Asp Glu Val Pro Glu Ala Val Asn Tyr Leu
                325                 330                 335

Leu Arg Gly Trp Ile Lys Asn Leu Glu Ser His Gly Ser Val Ala Leu
            340                 345                 350

Pro Leu His Glu Asp Ala Glu Val Val Glu Asn Ser Phe Ala Met Asp
        355                 360                 365

Leu Glu Phe Val Arg Glu Gly Ser Arg Lys Ser Val Ile Val Arg Phe
370                 375                 380

Phe Gly Ser Arg Phe Ser Ile Trp Asn Ser Phe Ser Ser Tyr Ile Lys
385                 390                 395                 400

Ser Gln Phe Lys Glu Thr Thr Ser Arg Ile Leu Thr
            405                 410
```

<210> SEQ ID NO 82
<211> LENGTH: 350
<212> TYPE: PRT
<213> ORGANISM: Ricinus communis

<400> SEQUENCE: 82

|

```
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Glu, Gly, Lys, Asp or absent
<220> FEATURE:
<221> NAME/KEY: MOD_RES
<222> LOCATION: (2)..(2)
<223> OTHER INFORMATION: Ser, Glu, Leu or absent
<220> FEATURE:
<221> NAME/KEY: MOD_RES
<222> LOCATION: (4)..(4)
<223> OTHER INFORMATION: Ser, Glu, Pro, Thr or absent
<220> FEATURE:
<221> NAME/KEY: MOD_RES
<222> LOCATION: (16)..(16)
<223> OTHER INFORMATION: Asn, Lys, Ser or absent
<220> FEATURE:
<221> NAME/KEY: MOD_RES
<222> LOCATION: (19)..(19)
<223> OTHER INFORMATION: Ile, Glu, Asp, Ser, Tyr, Cys or absent
<220> FEATURE:
<221> NAME/KEY: MOD_RES
<222> LOCATION: (22)..(22)
<223> OTHER INFORMATION: Arg, Leu, Pro, Val, Gln or absent
<220> FEATURE:
<221> NAME/KEY: MOD_RES
<222> LOCATION: (26)..(26)
<223> OTHER INFORMATION: Ser, Gly, His or Cys
<220> FEATURE:
<221> NAME/KEY: MOD_RES
<222> LOCATION: (43)..(43)
<223> OTHER INFORMATION: May or may not be present
<220> FEATURE:
<221> NAME/KEY: MOD_RES
<222> LOCATION: (92)..(92)
<223> OTHER INFORMATION: Thr, Cys, Gly, Ser, Phe or Val
<220> FEATURE:
<221> NAME/KEY: MOD_RES
<222> LOCATION: (98)..(98)
<223> OTHER INFORMATION: Met, Lys, Ser, Glu, Gln or Phe
<220> FEATURE:
<221> NAME/KEY: MOD_RES
<222> LOCATION: (100)..(100)
<223> OTHER INFORMATION: Glu, Thr, Ile, Ala, Lys or Arg
<220> FEATURE:
<221> NAME/KEY: MOD_RES
<222> LOCATION: (101)..(101)
<223> OTHER INFORMATION: Glu, Ser, Ala, Arg, Lys or Asp
<220> FEATURE:
<221> NAME/KEY: MOD_RES
<222> LOCATION: (105)..(105)
<223> OTHER INFORMATION: Ser, Leu or absent
<220> FEATURE:
<221> NAME/KEY: MOD_RES
<222> LOCATION: (107)..(107)
<223> OTHER INFORMATION: May or may not be present
<220> FEATURE:
<221> NAME/KEY: MOD_RES
<222> LOCATION: (108)..(108)
<223> OTHER INFORMATION: May or may not be present
<220> FEATURE:
<221> NAME/KEY: MOD_RES
<222> LOCATION: (120)..(120)
<223> OTHER INFORMATION: Thr, Leu, Ser, Pro, Ala or Ile
<220> FEATURE:
<221> NAME/KEY: MOD_RES
<222> LOCATION: (168)..(168)
<223> OTHER INFORMATION: His, Cys, Ser, Asn or Tyr
<220> FEATURE:
<221> NAME/KEY: MOD_RES
<222> LOCATION: (218)..(218)
<223> OTHER INFORMATION: Leu, Thr, Ala or Phe
<220> FEATURE:
<221> NAME/KEY: MOD_RES
<222> LOCATION: (278)..(278)
<223> OTHER INFORMATION: Ser, Glu, Gln, Gly, Lys or Arg
<220> FEATURE:
```

```
<221> NAME/KEY: MOD_RES
<222> LOCATION: (285)..(285)
<223> OTHER INFORMATION: Glu, Arg, Asp or Met
<220> FEATURE:
<221> NAME/KEY: MOD_RES
<222> LOCATION: (287)..(287)
<223> OTHER INFORMATION: Asn, Gly, Arg or Asp
<220> FEATURE:
<221> NAME/KEY: MOD_RES
<222> LOCATION: (350)..(350)
<223> OTHER INFORMATION: Gly, Glu, Ala, Asn, His, Lys or Leu
<220> FEATURE:
<221> NAME/KEY: MOD_RES
<222> LOCATION: (357)..(357)
<223> OTHER INFORMATION: Leu, Phe, Pro or absent
<220> FEATURE:
<221> NAME/KEY: MOD_RES
<222> LOCATION: (361)..(361)
<223> OTHER INFORMATION: Thr, Pro, Arg, Gly, Ala or absent
<220> FEATURE:
<221> NAME/KEY: MOD_RES
<222> LOCATION: (362)..(362)
<223> OTHER INFORMATION: Glu, Ser or absent
<220> FEATURE:
<221> NAME/KEY: MOD_RES
<222> LOCATION: (363)..(363)
<223> OTHER INFORMATION: Glu, Tyr, Ser, Asn, Val or absent
<220> FEATURE:
<221> NAME/KEY: MOD_RES
<222> LOCATION: (364)..(364)
<223> OTHER INFORMATION: Asp, Ala, Ile, Val or absent
<220> FEATURE:
<221> NAME/KEY: MOD_RES
<222> LOCATION: (366)..(366)
<223> OTHER INFORMATION: Glu, Asn, Arg, Tyr or absent
<220> FEATURE:
<221> NAME/KEY: MOD_RES
<222> LOCATION: (367)..(367)
<223> OTHER INFORMATION: Glu, Gly, Asp, Ser or absent
<220> FEATURE:
<221> NAME/KEY: MOD_RES
<222> LOCATION: (368)..(368)
<223> OTHER INFORMATION: May or may not be present
<220> FEATURE:
<221> NAME/KEY: MOD_RES
<222> LOCATION: (369)..(369)
<223> OTHER INFORMATION: May or may not be present
<220> FEATURE:
<221> NAME/KEY: MOD_RES
<222> LOCATION: (371)..(371)
<223> OTHER INFORMATION: Gly, Ser, Val, Thr, Ala or absent
<220> FEATURE:
<221> NAME/KEY: MOD_RES
<222> LOCATION: (379)..(379)
<223> OTHER INFORMATION: Asp, Gly, Glu, Gln or absent
<220> FEATURE:
<221> NAME/KEY: MOD_RES
<222> LOCATION: (386)..(386)
<223> OTHER INFORMATION: Asn, His, Ser, Arg, Ile or absent
<220> FEATURE:
<221> NAME/KEY: MOD_RES
<222> LOCATION: (388)..(388)
<223> OTHER INFORMATION: Trp, Arg, Gln, His or absent
<220> FEATURE:
<221> NAME/KEY: MOD_RES
<222> LOCATION: (389)..(389)
<223> OTHER INFORMATION: Leu, Phe or absent
<220> FEATURE:
<221> NAME/KEY: MOD_RES
<222> LOCATION: (394)..(394)
<223> OTHER INFORMATION: Tyr, Ile, Thr, Phe or absent
<220> FEATURE:
<221> NAME/KEY: MOD_RES
<222> LOCATION: (398)..(398)
<223> OTHER INFORMATION: Arg, Ser, Glu, Asn or absent
<220> FEATURE:
<221> NAME/KEY: MOD_RES
<222> LOCATION: (399)..(399)
<223> OTHER INFORMATION: Gly, Gln, Lys, Arg, Ser or absent
```

-continued

```
<220> FEATURE:
<221> NAME/KEY: MOD_RES
<222> LOCATION: (401)..(401)
<223> OTHER INFORMATION: Arg, Ser, Gly or absent
<220> FEATURE:
<221> NAME/KEY: MOD_RES
<222> LOCATION: (403)..(403)
<223> OTHER INFORMATION: Ser, Leu, Phe, Tyr or absent
<220> FEATURE:
<221> NAME/KEY: MOD_RES
<222> LOCATION: (407)..(407)
<223> OTHER INFORMATION: Ser, Asn, Arg, Gln or absent
<220> FEATURE:
<221> NAME/KEY: MOD_RES
<222> LOCATION: (408)..(408)
<223> OTHER INFORMATION: Phe, Thr, Val or absent
<220> FEATURE:
<221> NAME/KEY: MOD_RES
<222> LOCATION: (409)..(409)
<223> OTHER INFORMATION: Ile, Pro, Gln, Glu, Lys or absent
<220> FEATURE:
<221> NAME/KEY: MOD_RES
<222> LOCATION: (410)..(410)
<223> OTHER INFORMATION: Arg, Lys, Tyr, Ala, Glu or absent
<220> FEATURE:
<221> NAME/KEY: MOD_RES
<222> LOCATION: (411)..(411)
<223> OTHER INFORMATION: Val, Ser, Gly, Leu, Thr or absent
<220> FEATURE:
<221> NAME/KEY: MOD_RES
<222> LOCATION: (412)..(412)
<223> OTHER INFORMATION: Phe, Arg, Trp, Val, Glu, Thr or absent
<220> FEATURE:
<221> NAME/KEY: MOD_RES
<222> LOCATION: (413)..(413)
<223> OTHER INFORMATION: Gly, Val, Ile, Tyr, Ser or absent
<220> FEATURE:
<221> NAME/KEY: MOD_RES
<222> LOCATION: (414)..(414)
<223> OTHER INFORMATION: Gly, Ile, Val, Ser, Asn, Arg or absent
<220> FEATURE:
<221> NAME/KEY: MOD_RES
<222> LOCATION: (415)..(415)
<223> OTHER INFORMATION: Lys, Ser, Leu, Pro, Ile or absent
<220> FEATURE:
<221> NAME/KEY: MOD_RES
<222> LOCATION: (416)..(416)
<223> OTHER INFORMATION: Ser, Arg, Leu or absent
<220> FEATURE:
<221> NAME/KEY: MOD_RES
<222> LOCATION: (417)..(417)
<223> OTHER INFORMATION: Ala, Thr or absent

<400> SEQUENCE: 83

Xaa Xaa Ile Xaa Lys Val Ile Ile Pro Gly Leu Pro Asp Glu Ser Xaa
 1               5                  10                  15

Gly Glu Xaa Ser Ala Xaa Ile Ser Ser Xaa Phe Trp Glu Trp Lys Pro
             20                  25                  30

Lys Leu Ser Val His Tyr Glu Lys Ser Gly Thr Cys Asp Asn Val Lys
         35                  40                  45

Ala Pro Ala Val Leu Phe Leu Pro Gly Phe Gly Val Gly Ser Phe His
     50                  55                  60

Phe Glu Lys Gln Leu Lys Asp Leu Gly Arg Asp Tyr Arg Val Trp Ala
65                  70                  75                  80

Ile Asp Phe Leu Gly Gln Gly Met Ser Leu Pro Xaa Glu Asp Pro Ala
                 85                  90                  95

Pro Xaa Ser Xaa Xaa Gly Glu Leu Xaa Glu Arg Asp Asp Glu Asp Thr
            100                 105                 110

Phe Trp Gly Phe Gly Asp Glu Xaa Glu Pro Trp Ala Glu Glu Leu Val
        115                 120                 125
```

```
Tyr Ser Ile Asp Leu Trp Arg Asp Gln Val Gln Phe Ile Glu Glu Val
    130                 135                 140

Ile Gly Glu Pro Val Tyr Ile Val Gly Asn Ser Leu Gly Gly Phe Val
145                 150                 155                 160

Ala Leu Tyr Phe Ala Ala Ser Xaa Pro His Leu Val Lys Gly Val Thr
            165                 170                 175

Leu Leu Asn Ala Thr Pro Phe Trp Gly Phe Leu Pro Asn Pro Ala Arg
            180                 185                 190

Ser Pro Arg Leu Ser Lys Ile Phe Pro Trp Ala Gly Thr Phe Pro Leu
            195                 200                 205

Pro Ser Phe Val Arg Lys Leu Thr Glu Xaa Val Trp Gln Lys Ile Ser
    210                 215                 220

Asp Pro Arg Ser Ile Ala Glu Ile Leu Lys Gln Val Tyr Ala Asp His
225                 230                 235                 240

Ser Thr Asn Val Asp Lys Val Phe Ser Arg Ile Ile Glu Ile Thr Gln
                245                 250                 255

His Pro Ala Ala Ala Ser Phe Ala Ser Ile Met Phe Ala Pro Lys
            260                 265                 270

Gly Gln Leu Ser Phe Xaa Ala Leu Ser Arg Cys Gln Xaa Gln Xaa Ile
            275                 280                 285

Pro Ile Cys Leu Met Tyr Gly Arg Glu Asp Pro Trp Val Arg Pro Ile
    290                 295                 300

Trp Gly Leu Lys Val Lys Gln Gln Val Pro Glu Ala Pro Tyr Tyr Glu
305                 310                 315                 320

Ile Ser Pro Ala Gly His Cys Pro His Asp Glu Val Pro Glu Val Val
                325                 330                 335

Asn Tyr Leu Leu Arg Gly Trp Ile Lys Asn Leu Glu Ser Xaa Gly Ser
            340                 345                 350

Val Ala Leu Pro Xaa Leu Glu Asp Xaa Xaa Xaa Xaa Glu Xaa Xaa Ser
            355                 360                 365

Arg Val Xaa Arg Glu Leu Glu Phe Val Arg Xaa Gly Ser Lys Lys Ser
    370                 375                 380

Val Xaa Val Xaa Xaa Tyr Gly Ser Lys Xaa Ser Leu Trp Xaa Xaa Leu
385                 390                 395                 400

Xaa Ser Xaa Leu Lys Ser Xaa Xaa Xaa Xaa Xaa Xaa Xaa Xaa Xaa
            405                 410                 415

Xaa
```

US 9,493,748 B2

METHOD FOR TREATING PYROPHEOPHYTIN-CONTAINING COMPOSITIONS

CLAIM FOR PRIORITY

This application claims priority under 35 U.S.C. 371 to International Application No. PCT/IB2010/052581, filed on Jun. 10, 2010, which claims priority to U.S. Application No. 61/186,525, filed on Jun. 12, 2009, and U.S. Application No. 61/313,913, filed Mar. 12, 2010, each of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Jun. 25, 2015, is named 149230070_SL.txt and is 150,059 bytes in size.

The paper copy of the Sequence Listing submitted on Jul. 3, 2015 is hereby entered into the specification and is identical to the Sequence Listing submitted electronically on the same day.

FIELD

The present invention relates to a method, use, apparatus and related products for treating a composition comprising pyropheophytin. In one aspect, the invention is particularly applicable to the industrial processing of plant-derived food and feed products, such as vegetable oils. The invention may be employed to reduce or eliminate contamination by pyropheophytin in such products.

BACKGROUND

Chlorophyll is a green-coloured pigment widely found throughout the plant kingdom. Chlorophyll is essential for photosynthesis and is one of the most abundant organic metal compounds found on earth. Thus many products derived from plants, including foods and feeds, contain significant amounts of chlorophyll.

For example, vegetable oils derived from oilseeds such as soybean, palm or rape seed (canola), cotton seed and peanut oil typically contain some chlorophyll. However the presence of high levels of chlorophyll pigments in vegetable oils is generally undesirable. This is because chlorophyll imparts an undesirable green colour and can induce oxidation of oil during storage, leading to a deterioration of the oil.

Various methods have been employed in order to remove chlorophyll from vegetable oils. Chlorophyll may be removed during many stages of the oil production process, including the seed crushing, oil extraction, degumming, caustic treatment and bleaching steps. However the bleaching step is usually the most significant for reducing chlorophyll residues to an acceptable level. During bleaching the oil is heated and passed through an adsorbent to remove chlorophyll and other colour-bearing compounds that impact the appearance and/or stability of the finished oil. The adsorbent used in the bleaching step is typically clay.

In the edible oil processing industry, the use of such steps typically reduces chlorophyll levels in processed oil to between 0.02 to 0.05 ppm. However the bleaching step increases processing cost and reduces oil yield due to entrainment in the bleaching clay. Also the use of clay is expensive, this is particularly due to the treatment of the used clay (i.e. the waste) which can be difficult, dangerous and thus costly to handle. Thus attempts have been made to remove chlorophyll from oil by other means, for instance using the enzyme chlorophyllase.

In plants, chlorophyllase (chlase) is thought to be involved in chlorophyll degradation and catalyzes the hydrolysis of an ester bond in chlorophyll to yield chlorophyllide and phytol. WO 2006009676 describes an industrial process in which chlorophyll contamination can be reduced in a composition such as a plant oil by treatment with chlorophyllase. The water-soluble chlorophyllide which is produced in this process is also green in colour but can be removed by an aqueous extraction or silica treatment.

Chlorophyll is often partly degraded in the seeds used for oil production as well as during extraction of the oil from the seeds. One common modification is the loss of the magnesium ion from the porphyrin (chlorin) ring to form the derivative known as pheophytin (see FIG. 26). The loss of the highly polar magnesium ion from the porphyrin ring results in significantly different physico-chemical properties of pheophytin compared to chlorophyll. Typically pheophytin is more abundant in the oil during processing than chlorophyll. Pheophytin has a green colour and may be removed from the oil by an analogous process to that used for chlorophyll, for instance as described in WO 2006009676 by an esterase reaction catalyzed by an enzyme having a pheophytinase activity. Under certain conditions, some chlorophyllases are capable of hydrolyzing pheophytin as well as chlorophyll, and so are suitable for removing both of these contaminants. The products of pheophytin hydrolysis are the red/brown-colored pheophorbide and phytol. It is worth noting that pheophorbide can also be produced by the loss of a magnesium ion from chlorophyllide, i.e. following hydrolysis of chlorophyll (see FIG. 26). WO 2006009676 teaches removal of pheophorbide by an analogous method to chlorophyllide, e.g. by aqueous extraction or silica adsorption. Notably, however, pheophorbide is less water soluble than chlorophyllide and therefore cannot be as easily washed out with aqueous extraction (in particular with water).

Pheophytin may be further degraded to pyropheophytin, both by the activity of plant enzymes during harvest and storage of oil seeds or by processing conditions (e.g. heat) during oil refining (see "Behaviour of Chlorophyll Derivatives in Canola Oil Processing", JAOCS, Vol, no. 9 (September 1993) pages 837-841). One possible mechanism is the enzymatic hydrolysis of the methyl ester bond of the isocyclic ring of pheophytin followed by the non-enzymatic conversion of the unstable intermediate to pyropheophytin. A 28-29 kDa enzyme from *Chenopodium album* named pheophorbidase is reportedly capable of catalyzing an analogous reaction on pheophorbide, to produce the phytol-free derivative of pyropheophytin known as pyropheophorbide (see FIG. 26). Pyropheophorbide is less polar than pheophorbide resulting in the pyropheophorbide having a decreased water solubility and an increased oil solubility compared with pheophorbide.

Pyropheophytin is more abundant than both pheophytin and chlorophyll in vegetable oils during processing (see Table 9 in volume 2.2. of Bailey's Industrial Oil and Fat Products (2005), 6$^{th}$ edition, Ed. by Fereidoon Shahidi, John Wiley & Sons). This is partly because of the loss of magnesium from chlorophyll during harvest and storage of the plant material. Chlorophyll levels are also reduced by heating of oil seeds before pressing and extraction as well as the oil degumming and alkali treatment during the refining process. Thus chlorophyll is a relatively minor contaminant compared to pyropheophytin (and pheophytin) in many plant oils.

Pyropheophytin has a green colour and is a major undesirable contaminant in the oil, in view of its adverse effects on both colour and stability. Despite the attention directed to chlorophyll and (to a lesser extent) pheophytin removal, there is still a need for a suitable method to remove pyropheophytin and its derivatives (e.g. pyropheophorbide) from compositions such as vegetable oils. In particular, the chlorophyllases described in the prior art typically have little or no pyropheophytinase activity and are thus incapable of removing pyropheophytin contamination.

SUMMARY

In one aspect the present invention provides a method for treating a pyropheophytin-containing composition, comprising contacting the composition with an enzyme which is capable of hydrolysing pyropheophytin.

Preferably the composition is derived from a plant, algae or bacteria. In one embodiment, the composition comprises a plant-derived oil, e.g. a vegetable oil. Preferably the composition comprises an oil selected from rice bran, soy, canola (rape seed), palm, olive, cottonseed, corn, palm kernel, coconut, peanut, sesame or sunflower oil.

In one embodiment the enzyme comprises a pheophytinase or pheophytin pheophorbide hydrolase. The enzyme may be derived from, for example, a species selected from the following genera: *Arabidopsis, Populus, Vitis, Olyza, Zea, Nicotiana, Ostreocoecus, Ostreococcus, Physcomitrella, Phaeodactylum, Chlamydomonas,* or *Micromonas* or the enzyme may be derived from, for example, a species selected from *Arabidopsis thaliana, Populus trichocarpa, Vitis vinifera, Oryza sativa, Zea mays, Nicotiana tabacum, Ostreococcus lucimarinus, Ostreococcus taurii, Physcomitrella patens, Phaeodactylum tricornutum, Chlamydomonas reinhardtii,* or *Micromonas* sp RCC299

Preferably the enzyme comprises an amino acid sequence selected from: LPGFGVG (SEQ ID NO:13), DFLGQG (SEQ ID NO:14), GNSLGG (SEQ ID NO:15), LVKGVTLLNATPFW (SEQ ID NO:16), HPAA (SEQ ID NO:17), EDPW (SEQ ID NO:18), and SPAGHCPH (SEQ ID NO:19).

In one embodiment the enzyme comprises a polypeptide sequence as defined in SEQ ID NO:1 or any one of SEQ ID NO:s 4 to 12, or any one of SEQ ID NOs:21, 23 or 25, or a functional fragment or variant thereof, for example the enzyme comprises a polypeptide sequence having at least 50%, at least 75%, at least 85%, at least 90%, at least 95% or at least 99% sequence identity to SEQ ID NO:1 or any one of SEQ ID NO:s 4 to 12, or any one of SEQ ID NOs:21, 23 or 25, over at least 20, at least 50, at least 100 or at least 500 amino acid residues, or over the full length of the sequence.

In one embodiment, the enzyme has a pheophytinase to pyropheophytinase activity ratio of less than 80.

The enzyme may hydrolyze pyropheophytin in the composition to form pyropheophorbide. In some embodiments, the method further comprises a step of removing pyropheophorbide from the composition. Pyropheophorbide may be removed, for example, by a deodorization step or a silica treatment step, preferably by both a deodorization step and a silica treatment step.

Preferably the method comprises a two or more silica treatment steps. In one embodiment the silica treatment is performed at elevated temperature, e.g. at about 50 to 150° C., at 70 to 110° C. or about 90° C.

In one embodiment the enzyme which is capable of hydrolysing pyropheophytin is immobilized on a solid support. The method may further comprising contacting the composition with an enzyme having chlorophyllase activity, and the chlorophyllase may also optionally be immobilized on a solid support.

Preferably the method further comprises a step of contacting the composition with an acyltransferase.

Preferably the concentration of pyropheophytin in the composition is reduced by at least 10%, at least 50%, at least 75% or at least 90% compared to the concentration of pyropheophytin present in the composition before treatment.

In another aspect, the present invention provides a process for refining a plant (e.g. vegetable) oil, comprising treating a pyropheophytin-containing plant oil with a pyropheophytinase. Such a process may be performed on an industrial scale and may comprise various method steps as described above. The process may further comprise steps typically used in vegetable oil processing, such as a hexane extraction and/or a degumming step.

In a further aspect, the present invention provides use of a polypeptide having pyropheophytinase activity for removing pyropheophytin contamination from a composition. The use may be performed employing various method steps as discussed above.

In a further aspect, the present invention provides an apparatus for the enzymatic treatment of a pyropheophytin-containing composition, comprising (a) a plant oil refining apparatus; and (b) a polypeptide having pyropheophytinase activity operably integrated into the plant oil refining apparatus, such that the polypeptide is capable of hydrolyzing pyropheophytin in the composition during refining of the composition. The apparatus may comprise corresponding apparatus feature to perform a method or process as described above.

In a further aspect, the present invention provides a composition comprising a polypeptide having pyropheophytinase activity immobilized on silica. The polypeptide may be an enzyme as described in preferred embodiments of the method mentioned above.

In a further aspect, the present invention provides a polypeptide having an amino acid sequence as defined in SEQ ID NO:4, or encoded by a nucleic acid sequence as defined in SEQ ID NO:3, or a functional variant or fragment thereof having pyropheophytinase activity. For example, variants and/or fragments may show at least 90%, at least 95% or at least 99% sequence identity to SEQ ID NO:4 over at least 100, at least 200 or at least 300 amino acid residues or over the entire length of the sequence.

In a further aspect, the present invention provides a nucleic acid sequence as defined in SEQ ID NO:3, or a variant or fragment thereof encoding a functional pyropheophytinase. For example, variants and/or fragments may show at least 90%, at least 95% or at least 99% sequence identity to SEQ ID NO:3 over at least 300, at least 500 or at least 1000 nucleotide residues or over the entire length of the sequence. In further aspects the present invention provides an expression vector comprising a nucleic acid sequence as defined in SEQ ID NO:3 (e.g. an expression vector as shown in FIG. 13) and a transformed (host) cell comprising such an expression vector.

In a further aspect, the present invention provides a polypeptide having an amino acid sequence as defined in SEQ ID NO:25, or a functional variant or fragment thereof having pyropheophytinase activity. For example, variants and/or fragments may show at least 90%, at least 95% or at least 99% sequence identity to SEQ ID NO:25 over at least 100, at least 200 or at least 300 amino acid residues or over the entire length of the sequence.

In a further aspect, the present invention provides a composition obtainable by the process or method as defined above. For example, the composition may be a plant, algal or bacterial product, particularly a refined plant oil, e.g. a refined vegetable oil.

It has surprisingly been found that certain plant enzymes have pyropheophytinase activity, e.g. are capable of hydrolyzing an ester bond in pyropheophytin to form pyropheophorbide and phytol. Moreover, such pyropheophytinases are particularly useful for removing pyropheophytin contamination in plant-derived products such as vegetable oils.

BRIEF DESCRIPTION OF DRAWINGS

FIG. 1 shows an HPLC chromatogram using absorbance detection (430 nm) indicating numbered peaks associated with: 1=chlorophyllide b; 2=chlorophyllide a; 3=neoxanthin; 3'=neoxanthin isomer; 4=neochrome; 5=violaxanthin; 6=luteoxanthin; 7=auroxanthin; 8=anteraxanthin; 8'=anteraxanthin isomer; 9=mutatoxanthin; 10=lutein; 10'=lutein isomer; 10"=lutein isomer; 11=pheophorbide b; 12=pheophorbide a; 13=chlorophyll b; 13'=chlorophyll b'; 14=chlorophyll a; 14'=chlorophyll a'; 15=pheophytin b; 15'=pheophytin b'; 16=β-carotene; 17=pheophytin a; 17'=pheophytin a'; 18=pyropheophytin b; 19=pyropheophytin a.

FIG. 10 shows the amino acid sequence of a pheophytin pheophorbide hydrolase (PPH) from *Arabidopsis thaliana* (SEQ ID NO:1). A chloroplast transit peptide is shown in bold.

FIG. 11 shows the nucleotide sequence of a cDNA from *Arabidopsis thaliana* encoding pheophytin pheophorbide hydrolase (SEQ ID NO:2). The PPH of SEQ ID NO:1 is encoded by residues 173 to 1627 of SEQ ID NO:2.

FIG. 12 shows a synthetic gene encoding pheophytin pheophorbide hydrolase (pheophytinase) with codons designed for expression in the filamentous fungi *Trichoderma reesei* (nucleotide sequence SEQ ID NO:3, amino acid sequence SEQ ID NO:4).

FIG. 15 shows the polypeptide sequence of *Populus trichocarpa* PPH (SEQ ID NO:5).

FIG. 16 shows the polypeptide sequence of *Vitis vinifera* PPH (SEQ ID NO:6).

FIG. 17 shows the polypeptide sequence of *Ricinus communis* PPH (SEQ ID NO:7).

FIG. 18 shows the polypeptide sequence of *Oryza sativa* (japonica cultivar-group) PPH (SEQ ID NO:8).

FIG. 19 shows the polypeptide sequence of *Zea mays* PPH (SEQ ID NO:9).

FIG. 20 shows the polypeptide sequence of *Nicotiana tabacum* PPH (SEQ ID NO:10).

FIG. 21 shows the polypeptide sequence of *Oryza sativa* Japonica Group PPH (SEQ ID NO:11).

FIG. 22 shows (a) the polypeptide sequence of *Physcomitrella patens* subsp. *patens* PPH (SEQ ID NO:12) and (b) the polypeptide sequence of *Arabidopsis thaliana* chlorophyllase (SEQ ID NO:20).

FIG. 23 shows an amino acid sequence alignment of the *Arabidopsis thaliana* PPH protein with putative PPHs (SEQ ID NOs 73-83). Conserved blocks of the following amino acid sequences were found and are shown herein: LPGFGVG (SEQ ID NO:13), DFLGQG (SEQ ID NO:14), GNSLGG (SEQ ID NO:15), LVKGVTLLNATPFW (SEQ ID NO:16), HPAA (SEQ ID NO:17), EDPW (SEQ ID NO:18), and SPAGHCPH (SEQ ID NO:19).

FIG. 27 shows the amino acid sequence of *Triticum aestivum* chlorophyllase (SEQ ID NO:21).

FIG. 28 shows a nucleotide sequence encoding *Triticum aestivum* chlorophyllase (SEQ ID NO:22).

FIG. 29 shows the amino acid sequence of *Chlamydomonas reinhardtii* chlorophyllase (SEQ ID NO:23).

FIG. 30 shows a nucleotide sequence encoding *Chlamydomonas reinhardtii* chlorophyllase (SEQ ID NO:24).

FIG. 35 shows an amino acid sequence of a variant (Triticum Nd1-16) of *Triticum aestivum* chlorophyllase lacking the N-terminal 16 amino acids compared to the wild-type enzyme (SEQ ID NO:25).

FIG. 36 shows a nucleotide sequence encoding a variant (Triticum Nd1-16) of *Triticum aestivum* chlorophyllase lacking the N-terminal 16 amino acids compared to the wild-type enzyme (SEQ ID NO:26).

DETAILED DESCRIPTION

In one aspect the present invention relates to a method for treating a pyropheophytinase-containing composition. Typically the method is performed in order to remove pyropheophytin from the composition, or to reduce the level of pyropheophytin in the composition, for instance where the pyropheophytin is present as a contaminant.

Pyropheophytin has a green colour, which is derived from the porphyrin (chlorin) ring present in the molecule. Thus the presence of pyropheophytin in a composition, e.g. a vegetable oil, can give such a composition an undesirable green or greenish colour. In one embodiment, the present method may be performed in order to remove or reduce the green colouring present in a composition. Accordingly the present method may be referred to as a bleaching or de-colorizing process.

Figure 26:
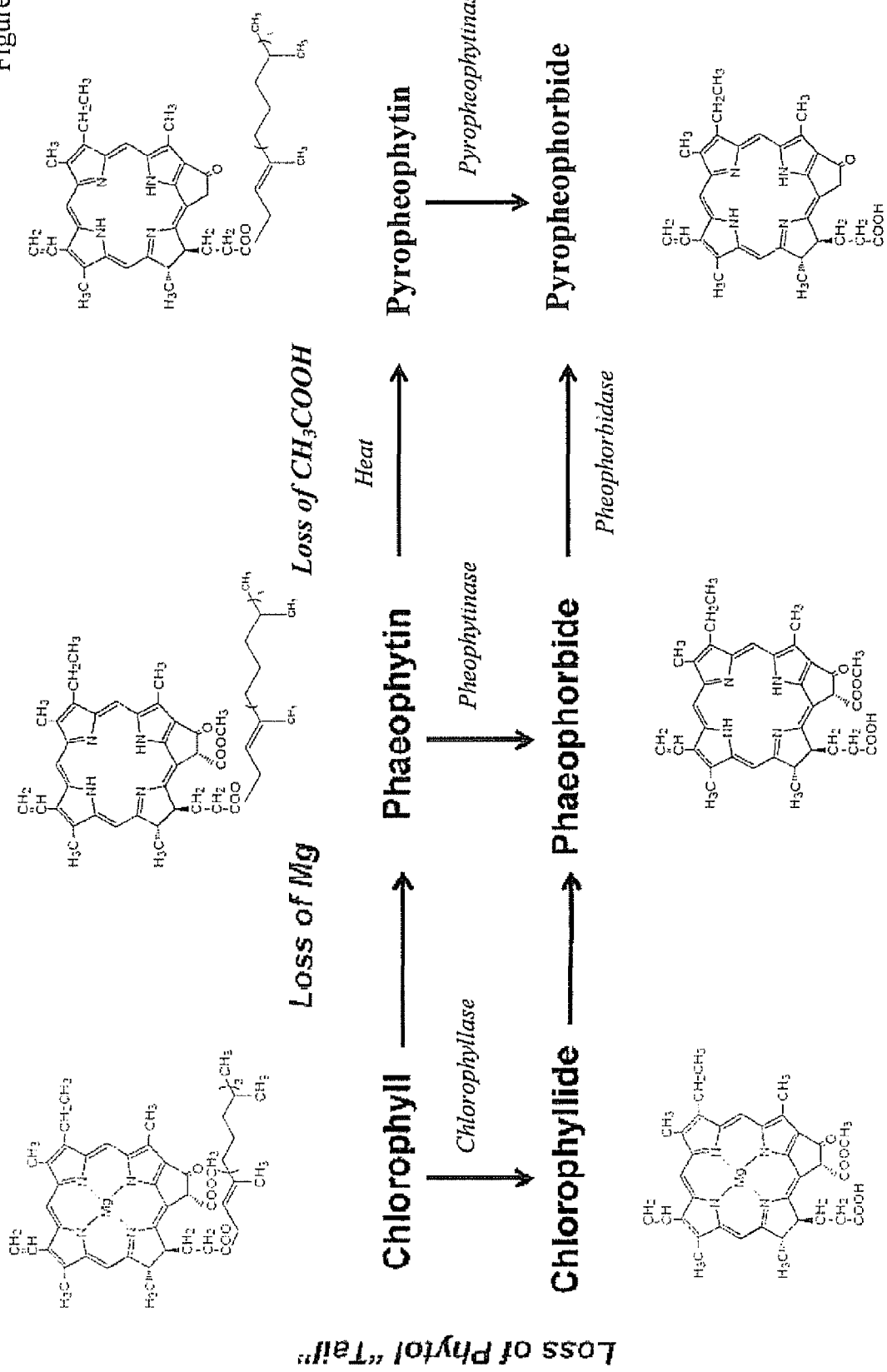
FIG. 26 shows the reactions involving chlorophyll and derivatives and enzymes used in the present invention.

Hydrolysis of pyropheophytin yields phytol and pyropheophorbide (see FIG. 26). Pyropheophorbide contains the colour-bearing porphyrin ring, although loss of the phytol chain means that pyropheophorbide has a reddish brown, rather than green, colour. In some embodiments, it may also be desirable to remove pyropheophorbide and to reduce the red/brown colouring in the composition. Thus in one embodiment of the invention, the method may further comprise a step of removing or reducing the level of pyropheophorbide in the composition. The present method may involve bleaching or de-colorizing to remove the green and/or red/brown colouring of the composition.

The present invention in one embodiment relates to the selection, expression and use of an enzyme with activity on magnesium free degradation products of chlorophyll (in particular at least pyropheophytin, such as pheophytin and pyropheophytin) and with low or no activity on chlorophyll. Preferable the enzyme of the invention has 80% more activity on magnesium free chlorophyll degradation products (preferably on pyropheophytin) than on chlorophyll, more preferable the enzyme of the invention has more than 90% more activity on magnesium free chlorophyll degradation products (preferably on pyropheophytin) than on chlorophyll. More preferable 95% more activity on magnesium free chlorophyll degradation products (preferably on pyropheophytin) than on chlorophyll.

Compositions

Any composition comprising pyropheophytin may be treated according to the present method, in order to remove undesirable pyropheophytin contamination. Preferably the composition is a plant-derived preparation, an algal preparation or a bacterial-derived preparation, e.g. the composition is a product derived from any type of plant, algae or bacteria (e.g. cyanobacteria). In one embodiment the composition comprises a plant material, plant oil or plant extract. The term "plant" includes whole plants, plant parts (e.g., leaves, stems, flowers, roots, etc.), plant protoplasts, seeds and plant cells and progeny of same. The class of plants from which products can be treated in the method of the invention includes higher plants, including angiosperms (monocotyledonous and dicotyledonous plants), as well as gymnosperms. It includes plants of a variety of ploidy levels, including polyploid, diploid, haploid and hemizygous states.

In preferred embodiments, the composition may comprise a plant oil such as a vegetable oil, including oils processed from oil seeds or oil fruits (e.g. seed oils such as canola (rapeseed) oil and fruit oils such as palm). Examples of suitable oils include rice bran, soy, canola (rape seed), palm, olive, cottonseed, corn, palm kernel, coconut, peanut, sesame or sunflower. The methods of the invention can be used in conjunction with methods for processing essential oils, e.g., those from fruit seed oils, e.g. grapeseed, apricot, borage, etc.

Alternatively, the composition may comprise an algal preparation; a textile, thread or fabric or a cloth; or a wood or paper product by-product, such as a wood pulp, a paper pulp, a Kraft pulp, or a non-wood paper product or by-product, such as a rice paper. In other aspects of the methods, the composition may comprise a pharmaceutical or cosmetic formulation (e.g. liposomes for pharmaceuticals and cosmetics), a biodiesel oil, a food, an edible oil, a feed, or a dietary supplement.

The methods of the invention can be used to treat crude or refined oils derived from plant (e.g. vegetable or algae) sources or alternatively from synthetic sources. The method of the invention can be used to treat crude or refined oils at higher oil concentrations, or, in one aspect, used to treat unrefined and non-diluted crude oils. The methods of the invention can be used in conjunction with methods for processing high phosphorus oils (e.g. a soy bean oil).

Pyropheophytin Removal

The pyropheophytin may be present in the composition (e.g. a preparation, feed, food or oil) naturally, as a contaminant, or as an undesired component in a processed product. The pyropheophytin may be present at any level in the composition. Typically pyropheophytin may be present as a natural contaminant in the composition (e.g. in a vegetable oil) at a concentration of 0.001 to 1000 mg/kg (0.001 to 1000 ppm, $10^{-7}$ to $10^{-1}$ wt %), based on the total weight of the composition (e.g. a vegetable oil). In further embodiments, the pyropheophytin may be present in the composition at a concentration of 0.1 to 100, 0.5 to 50, 1 to 50, 1 to 30 or 1 to 10 mg/kg, based on the total weight of the composition.

The method of the present invention typically reduces the level of pyropheophytin in the composition. For example, the method may reduce the concentration of pyropheophytin by at least 5%, at least 10%, at least 20%, at least 30%, at least 40%, at least 50%, at least 60%, at least 70%, at least 80%, at least 90%, at least 95% or at least 99%, compared to the concentration of pyropheophytin (by weight) present in the total composition before treatment. Thus in particular embodiments, the pyropheophytin concentration in the composition (e.g. in a vegetable oil) after treatment may be less than 100, less than 50, less than 30, less than 10, less than 5, less than 1, less than 0.5, less than 0.1 mg/kg or less than 0.02 mg/kg, based on the total weight of the composition (e.g. a vegetable oil).

Pyropheophorbide Removal

The method of the present invention may optionally involve a step of removing pyropheophorbide. Pyropheophorbide may be present in the composition due to the hydrolysis of pyropheophytin by the enzyme of the invention, or may be present naturally, as a contaminant, or as an undesired component in a processed product. Pyropheophorbide may also be present in the composition due to the breakdown of pheophorbide, which may itself be produced by the activity of an enzyme having pheophytinase activity on pheophytin, or pheophorbide may be formed from chlorophyllide following the action of chlorophyllase on chlorophyll (see FIG. 26). Various steps in the formation of pyropheophorbide may be favoured by the processing conditions used in oil refining, in particular heat, or by the use enzymes such as pheorphorbidase, chlorophyllase and/or pheophytinase in the process.

The pyropheophorbide may be present at any level in the composition. Typically pyropheophorbide may be present in the composition (erg, in a vegetable oil), either before or after treatment with a pyropheophytinase according to the method of the present invention, at a concentration of 0.001 to 1000 mg/kg (0.001 to 1000 ppm, $10^{-7}$ to $10^{-1}$ wt %), based on the total weight of the composition (e.g. a vegetable oil). In further embodiments, the pyropheophorbide may be present in the composition at a concentration of 0.1 to 100, 0.5 to 50, 1 to 50, 1 to 30 or 1 to 10 mg/kg, based on the total weight of the composition.

In one embodiment the method of the present invention reduces the level of pyropheophorbide in the composition, compared to either or both of the levels before and after pyropheophytinase treatment. Thus in some embodiments the pyropheophorbide concentration may increase after pyropheophytinase treatment. Typically the method involves a step of removing pyropheophorbide such that the pyropheophorbide concentration is lower than after pyropheophytinase treatment. Preferably the pyropheophorbide produced by this enzymatic step is removed from the composition, such that the final level of pyropheophorbide in the composition is lower than before pyropheophytinase treatment.

For example, the method may reduce the concentration of pyropheophorbide by at least 5%, at least 10%, at least 20%, at least 30%, at least 40%, at least 50%, at least 60%, at least 70%, at least 80%, at least 90%, at least 95% or at least 99%, compared to the concentration of pyropheophorbide (by weight) present in the total composition before the pyropheophorbide removal step, e.g. before or after pyropheophytinase treatment. Thus in particular embodiments, the pyropheophorbide concentration in the composition (e.g. in a vegetable oil) after the pyropheophorbide removal step may be less than 100, less than 50, less than 30, less than 10, less than 5, less than 1, less than 0.5, less than 0.1 mg/kg, or less than 0.02 mg/kg, based on the total weight of the composition (e.g a vegetable oil).

Pyropheophytinase

The method of the present invention comprises a step of contacting a pyropheophytin-containing composition with an enzyme having pyropheophytinase activity. Any polypeptide having an activity that can modify pyropheophytin can be used as the enzyme in the method of the invention. By "pyropheophytinase activity" it is preferably meant that the enzyme can hydrolyse an ester bond in pyropheophytin to produce phytol and pyropheophorbide. Thus the enzyme typically has an esterase or hydrolase activity. Preferably the enzyme is capable of pyropheophytinase activity in an oil phase, and optionally also in an aqueous phase.

Pyropheophytinase activity may be detected using any suitable assay technique, for example based on the enzyme activity (pheophytinase and phyropheophytinase activity) assay described in the examples below using pyropheophytin as substrate. For example, pyropheophytinase activity may be detected using fluorescence-based techniques, e.g. by monitoring pyropheophorbide as described in Example 5 below. In one suitable assay, a polypeptide to be tested for pyropheophytinase activity is incubated in the presence of pyropheophytin, and pyropheophytin, pyropheophorbide and/or phytol levels are monitored by fluorescence measurement. Alternatively, a pyropheophytinase assay may be based on HPLC detection and quantitation of pyropheophytin, pyropheophorbide and/or phytol levels following addition of a putative enzyme, e.g. based on the techniques described in the examples with particular reference to Example 5 below.

Pyropheophytinase activity may be determined using methods based on those disclosed in, for example, Ali Khamessan et al. (1994), Journal of Chemical Technology & Biotechnology, 60(1), pages 73-81; Klein and Vishniac (1961), J. Biol. Chem. 236: 2544-2547; and Kiani et al. (2006), Analytical Biochemistry 353: 93-98. Pyropheophytin may be used in place of chlorophyll as substrate where appropriate.

Alternatively, a suitable assay may be based on HPLC detection and quantitation of pyropheophytin or pyropheophorbide levels following addition of a putative enzyme, e.g. based on the techniques described below. In one embodiment, the assay may be based on a method as described in Hornero-Mendez et al. (2005), Food Research International 38(8-9): 1067-1072. In another embodiment, the following assay may be used:

170 µl mM HEPES, pH 7.0 is added 20 µl 0.3 mM pyropheophytin dissolved in acetone. The enzyme is dissolved in 50 mM HEPES, pH 7.0. 10 µl enzyme solution is added to 190 µl substrate solution to initiate the reaction and incubated at 40° C. for various time periods. The reaction was stopped by addition of 350 µl acetone. Following centrifugation (2 min at 18,000 g) the supernatant was analyzed by HPLC, and the amounts of pyropheophytin and pyropheophorbide determined.

One unit of pyropheophytinase activity is defined as the amount of enzyme which hydrolyzes one micromole of pyropheophytin per minute at 40° C., e.g. in an assay method as described herein.

In preferred embodiments, the enzyme used in the present method has pyropheophytinase activity of at least 100 U/g, at least 250 U/g or at least 500 U/g, based on the units of activity per gram of the purified enzyme, e.g. as determined by an assay method described herein.

In some embodiments, the enzyme may have further activities in addition to the pyropheophytinase activity, e.g. a pheophytinase activity and/or a chlorophyllase activity. Thus the enzyme need not be selective for pyropheophytin, and may be capable of utilizing pheophytin and/or chlorophyll as substrates in addition to pyropheophytin, provided that the enzyme shows significant activity towards pyropheophytin. By "enzyme" it is intended to encompass any polypeptide having pyropheophytinase activity, including e.g. catalytic antibodies, enzyme fragments, etc. Any isolated, recombinant or synthetic or chimeric (or a combination of synthetic and recombinant) polypeptide (e.g. enzyme or catalytic antibody) can be used. Thus as used herein, the term "pyropheophytinase" encompasses any polypeptide capable of hydrolyzing pyropheophytin. Pheophytinase and chlorophyllase activity may be determined by analogous methods to those described above for pyropheophytinase, replacing pyropheophytin as substrate with pheophytin or chlorophyll where appropriate.

In one embodiment, the enzyme is capable of hydrolyzing pheophytin and pyropheophytin More preferably, the enzyme is capable of hydrolyzing pheophytin and pyropheophytin but is incapable of hydrolyzing chlorophyll. For example, the enzyme may be pheophytinase or pheophytin pheophorbide hydrolase (PPH), e.g. an enzyme as described in Schelbert et al., The Plant Cell 21:767-785 (2009).

In another embodiment, the enzyme preferably has a pheophytinase to pyropheophytinase activity ratio of less than 80, less than 70, less than 60, less than 50, less than 40 or less than 30. For example, the enzyme may have a pheophytinase to pyropheophytinase activity ratio of 0.1 to 70, 1 to 50 or 10 to 30. The pheophytinase to pyropheophytinase activity ratio may be calculated by determining pheophytinase activity and pyropheophytinase activity using methods described above, and dividing the pheophytinase activity by the pyropheophytinase activity. Particularly preferred enzymes having a low ratio of pheophytinase to pyropheophytinase activity are derived from *Triticum* sp. or *Chlamydomonas* sp. as described below.

In one embodiment, the enzyme is derived from wheat, e.g. from *Triticum* sp, especially from *Triticum aestivum*. For example, the enzyme may be a polypeptide comprising the sequence of SEQ ID NO:21 (see FIG. 27), or may be encoded by the nucleotide sequence of SEQ ID NO:22 (see FIG. 28).

In another embodiment, the enzyme is derived from *Chlamydomonas* sp, especially from *Chlamydomonas reinhardtii*. For example, the enzyme may be a polypeptide comprising the sequence of SEQ ID NO:23 (see FIG. 29), or may be encoded by the nucleotide sequence of SEQ ID NO:24 (see FIG. 30).

In one embodiment, the enzyme is an N-terminally truncated variant of a chlorophyllase and/or pyropheophytinase, e.g. an N-terminally truncated variant of SEQ ID NO:1, any one of SEQ ID NO:s 4 to 12, or SEQ ID NOs:21 or 23. In particular embodiments, such N-terminally truncated variants may lack at least 1, 2, 5, 10 or 15 amino acids (e.g. 1 to 30 or 5 to 20 amino acids) at the N-terminal compared to the parent sequence. In one embodiment, the enzyme comprises the sequence of SEQ ID NO:25 (see FIG. 35), i.e. an N-terminally truncated variant of SEQ ID NO:21.

It has surprisingly been found that chlorophyllases from *Triticum* and *Chlamydomonas* have pyropheophytinase activity, and a relatively low ratio of pheophytinase to pyropheophytinase activity. Moreover, an N-terminally truncated variant of *Triticum* chlorophyllase has a reduced ratio of pheophytinase to pyropheophytinase activity compared to the wild-type enzyme.

Pheophytin Pheophorbide Hydrolase

It has surprisingly been found that PPH and related enzymes are capable of hydrolyzing pyropheophytin in addition to pheophytin. However PPH is inactive on chlorophyll. As described in Schelbert et al., PPH orthologs are commonly present in eukaryotic photosynthesizing organisms. PPHs represent a defined sub-group of α/β hydrolases which are phylogenetically distinct from chlorophyllases, the two groups being distinguished in terms of sequence homology and substrates.

In specific embodiments of the invention, the enzyme may be any known PPH derived from any species or a functional variant or fragment thereof or may be derived from any known PPH enzyme. For example, in one embodiment, the enzyme is a PPH from *Arabidopsis thaliana*, e.g. a polypeptide comprising the amino acid sequence of SEQ ID NO:1, or a polypeptide encoded by the nucleotide sequence of SEQ ID NO:2 (NCBI accession no. NP_196884, GenBank ID No. 15240707), or a functional variant or fragment thereof. In another embodiment, the enzyme comprises the amino acid sequence of SEQ ID NO:4, or a polypeptide encoded by the nucleotide sequence of SEQ ID NO:3, or a functional variant or fragment thereof.

In further embodiments, the enzyme may be a PPH derived from any one of the following species: *Arabidopsis thaliana, Populus trichocarpa, Vitis vinifera, Oryza sativa, Zea mays, Nicotiana tabacum, Ostreococcus lucimarinus, Ostreococcus taurii, Physcomitrella patens, Phaeodactylum tricornutum, Chlamydomonas reinhardtii*, or *Micromonas* sp. RCC299. For example, the enzyme may be a polypeptide comprising an amino acid sequence, or encoded by a nucleotide sequence, defined in one of the following database entries shown in Table 1, or a functional fragment or variant thereof:

TABLE 1

| Organism | Accession | Genbank ID |
| --- | --- | --- |
| Arabidopsis thaliana | NP_196884 | 15240707 |
| Populus trichocarpa | XP_002314066 | 224106163 |
| Vitis vinifera | CAO40741 | 157350650 |
| Oryza sativa (japonica) | NP_001057593 | 115467988 |
| Zea mays | ACF87407 | 194706646 |
| Nicotiana tabacum | CAO99125 | 156763846 |
| Ostreococcus lucimarinus | XP_001415589 | 145340970 |
| Ostreococcus tauri | CAL50341 | 116000661 |
| Physcomitrella patens | XP_001761725 | 168018382 |
| Phaeodactylum tricornutum | XP_002181821 | 219122997 |
| Chlamydomonas reinhardtii | XP_001702982 | 159490010 |
| Micromonas sp. RCC299 | ACO62405 | 226516410 |

For example, the enzyme may be a polypeptide as defined in any of SEQ ID NO:s 5 to 12, or a functional fragment or variant thereof.

Variants and Fragments

Functional variants and fragments of known pyropheophytinase (e.g. PPH) sequences may also be employed in the present invention. By "functional" it is meant that the fragment or variant retains a detectable pyropheophytinase activity. Typically such variants and fragments show homology to a known pyropheophytinase (e.g. PPH) sequence, e.g. at least about 50%, 60%, 70%, 75%, 80%, 85%, 90%, 95%, 96%, 97%, 98%, 99%, or more sequence identity to a known pyropheophytinase (e.g. PPH) amino acid sequence, e.g. to SEQ ID NO:1 or any one of SEQ ID NOs: 4 to 12 or a sequence defined in Table 1, or to SEQ ID NO:21, 23 or 25, over a region of at least about 10, 20, 30, 50, 100, 200, 300, 500, or 1000 or more residues, or over the entire length of the sequence.

The percentage of sequence identity may be determined by analysis with a sequence comparison algorithm or by a visual inspection. In one aspect, the sequence comparison algorithm is a BLAST algorithm, e.g., a BLAST version 2.2.2 algorithm.

Other enzymes having pyropheophytinase activity suitable for use in the methods of the invention may be identified by determining the presence of conserved sequence motifs present e.g. in known PPH sequences. Conserved sequence motifs include the following: LPGFGVG (SEQ ID NO:13), DFLGQG (SEQ ID NO:14), GNSLGG (SEQ ID NO:15), LVKGVTLLNATPFW (SEQ ID NO:16), HPAA (SEQ ID NO:17), EDPW (SEQ ID NO:18), and SPAGHCPH (SEQ ID NO:19). Thus preferred pyropheophytinases for use in the present invention comprise one or more of these sequences. The GNSLGG (SEQ ID NO:15) motif contains the active site serine residue. It is particularly preferred that the enzyme used in the method of the invention comprises a GNSLGG sequence (SEQ ID NO: 15). Polypeptide sequences having suitable pyropheophytinase activity may be identified by searching genome databases, e.g. the microbiome metagenome database (JGI-DOE, USA), for the presence of these motifs.

Isolation and Production of Pyropheophytinases

Enzymes for use in the present invention may be isolated from their natural sources or may be, for example, produced using recombinant DNA techniques. Nucleotide sequences encoding polypeptides having pyropheophytinase activity may be isolated or constructed and used to produce the corresponding polypeptides.

For example, a genomic DNA and/or cDNA library may be constructed using chromosomal DNA or messenger RNA from the organism producing the polypeptide. If the amino acid sequence of the polypeptide is known, labeled oligonucleotide probes may be synthesised and used to identify polypeptide-encoding clones from the genomic library prepared from the organism. Alternatively, a labelled oligonucleotide probe containing sequences homologous to another known polypeptide gene could be used to identify polypeptide-encoding clones. In the latter case, hybridisation and washing conditions of lower stringency are used.

Alternatively, polypeptide-encoding clones could be identified by inserting fragments of genomic DNA into an expression vector, such as a plasmid, transforming enzyme-negative bacteria with the resulting genomic DNA library, and then plating the transformed bacteria onto agar containing an enzyme inhibited by the polypeptide, thereby allowing clones expressing the polypeptide to be identified.

In a yet further alternative, the nucleotide sequence encoding the polypeptide may be prepared synthetically by established standard methods, e.g. the phosphoroamidite method described by Beucage S. L. et al (1981) Tetrahedron Letters 22, p 1859-1869, or the method described by Matthes et al (1984) EMBO J. 3, p 801-805. In the phosphoroamidite method, oligonucleotides are synthesised, e.g. in an automatic DNA synthesiser, purified, annealed, ligated and cloned in appropriate vectors.

The nucleotide sequence may be of mixed genomic and synthetic origin, mixed synthetic and cDNA origin, or mixed genomic and cDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al (Science (1988) 239, pp 487-491).

The term "nucleotide sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or antisense strand.

Typically, the nucleotide sequence encoding a polypeptide having pyropheophytinase activity is prepared using recombinant DNA techniques. However, in an alternative embodiment of the invention, the nucleotide sequence could be synthesised, in whole or in part, using chemical methods well known in the art (see Caruthers M H et al (1980) Nuc Acids Res Symp Ser 215-23 and Horn T et al (1980) Nuc Acids Res Symp Ser 225-232).

Modification of Enzyme Sequences

Once an enzyme-encoding nucleotide sequence has been isolated, or a putative enzyme-encoding nucleotide sequence has been identified, it may be desirable to modify the selected nucleotide sequence, for example it may be desirable to mutate the sequence in order to prepare an enzyme in accordance with the present invention.

Mutations may be introduced using synthetic oligonucleotides. These oligonucleotides contain nucleotide sequences flanking the desired mutation sites. A suitable method is disclosed in Morinaga et al (Biotechnology (1984) 2, p646-649). Another method of introducing mutations into enzyme-encoding nucleotide sequences is described in Nelson and Long (Analytical Biochemistry (1989), 180, p 147-151).

Instead of site directed mutagenesis, such as described above, one can introduce mutations randomly for instance using a commercial kit such as the GeneMorph PCR mutagenesis kit from Stratagene, or the Diversify PCR random mutagenesis kit from Clontech. EP 0 583 265 refers to methods of optimising PCR based mutagenesis, which can also be combined with the use of mutagenic DNA analogues such as those described in EP 0 866 796. Error prone PCR technologies are suitable for the production of variants of pyropheophytinases with preferred characteristics, WO0206457 refers to molecular evolution of lipases.

A third method to obtain novel sequences is to fragment non-identical nucleotide sequences, either by using any number of restriction enzymes or an enzyme such as Dnase I, and reassembling full nucleotide sequences coding for functional proteins. Alternatively one can use one or multiple non-identical nucleotide sequences and introduce mutations during the reassembly of the full nucleotide sequence. DNA shuffling and family shuffling technologies are suitable for the production of variants of pyropheophytinases with preferred characteristics. Suitable methods for performing 'shuffling' can be found in EP0752008, EP1138763, EP1103606. Shuffling can also be combined with other forms of DNA mutagenesis as described in U.S. Pat. No. 6,180,406 and WO 01/34835.

Thus, it is possible to produce numerous site directed or random mutations into a nucleotide sequence, either in vivo or in vitro, and to subsequently screen for improved functionality of the encoded polypeptide by various means. Using in silico and exo mediated recombination methods (see WO 00/58517, U.S. Pat. Nos. 6,344,328, 6,361,974), for example, molecular evolution can be performed where the variant produced retains very low homology to known enzymes or proteins. Such variants thereby obtained may have significant structural analogy to known pheophytinase or pyropheophytinase enzymes, but have very low amino acid sequence homology.

As a non-limiting example, in addition, mutations or natural variants of a polynucleotide sequence can be recombined with either the wild type or other mutations or natural variants to produce new variants. Such new variants can also be screened for improved functionality of the encoded polypeptide.

The application of the above-mentioned and similar molecular evolution methods allows the identification and selection of variants of the enzymes of the present invention which have preferred characteristics without any prior knowledge of protein structure or function, and allows the production of non-predictable but beneficial mutations or variants. There are numerous examples of the application of molecular evolution in the art for the optimisation or alteration of enzyme activity, such examples include, but are not limited to one or more of the following: optimised expression and/or activity in a host cell or in vitro, increased enzymatic activity, altered substrate and/or product specificity, increased or decreased enzymatic or structural stability, altered enzymatic activity/specificity in preferred environmental conditions, e.g. temperature, pH, substrate.

As will be apparent to a person skilled in the art, using molecular evolution tools an enzyme may be altered to improve the functionality of the enzyme. Suitably, a nucleotide sequence encoding a pyropheophytinase (e.g. a PPH) used in the invention may encode a variant pyropheophytinase (e.g. a variant PPH), i.e. the pyropheophytinase (e.g. PPH) may contain at least one amino acid substitution, deletion or addition, when compared to a parental enzyme. Variant enzymes retain at least 1%, 2%, 3%, 5%, 10%, 15%, 20%, 30%, 40%, 50%, 60%, 70%, 80%, 90%, 95%, 97%, or 99% identity with the parent enzyme, Suitable parent enzymes may include any enzyme with pyropheophytinase activity.

Pyropheophytinase Polypeptide Sequences

The present invention also encompasses the use of amino acid sequences encoded by a nucleotide sequence which encodes a pyropheophytinase for use in any one of the methods and/or uses of the present invention.

As used herein, the term "amino acid sequence" is synonymous with the term "polypeptide" and/or the term "protein". In some instances, the term "amino acid sequence" is synonymous with the term "peptide". The amino acid sequence may be prepared/isolated from a suitable source, or it may be made synthetically or it may be prepared by use of recombinant DNA techniques. Suitably, the amino acid sequences may be obtained from the isolated polypeptides taught herein by standard techniques.

One suitable method for determining amino acid sequences from isolated polypeptides is as follows. Purified polypeptide may be freeze-dried and 100 μg of the freeze-dried material may be dissolved in 50 μl of a mixture of 8 M urea and 0.4 M ammonium hydrogen carbonate, pH 8.4. The dissolved protein may be denatured and reduced for 15 minutes at 50° C. following overlay with nitrogen and addition of 5 μl of 45 mM dithiothreitol. After cooling to room temperature, 5 μl of 100 mM iodoacetamide may be added for the cysteine residues to be derivatized for 15 minutes at room temperature in the dark under nitrogen.

135 μl of water and 5 μg of endoproteinase Lys-C in 5 μl of water may be added to the above reaction mixture and the digestion may be carried out at 37° C. under nitrogen for 24 hours. The resulting peptides may be separated by reverse phase HPLC on a VYDAC C18 column (0.46×15 cm; 10 μm; The Separation Group, California, USA) using solvent A: 0.1% TFA in water and solvent B: 0.1% TFA in acetonitrile. Selected peptides may be re-chromatographed on a Develosil C18 column using the same solvent system, prior to N-terminal sequencing. Sequencing may be done using an Applied Biosystems 476A sequencer using pulsed liquid fast cycles according to the manufacturer's instructions (Applied Biosystems, California, USA).

Sequence Comparison

Here, the term "homologue" means an entity having a certain homology with the subject amino acid sequences and the subject nucleotide sequences. Here, the term "homology" can be equated with "identity". The homologous amino acid sequence and/or nucleotide sequence should provide and/or encode a polypeptide which retains the functional activity and/or enhances the activity of the enzyme.

In the present context, a homologous sequence is taken to include an amino acid sequence which may be at least 75, 85 or 90% identical, preferably at least 95 or 98% identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

In the present context, a homologous sequence is taken to include a nucleotide sequence which may be at least 75, 85 or 90% identical, preferably at least 95 or 98% identical to a nucleotide sequence encoding a polypeptide of the present invention (the subject sequence). Typically, the homologues will comprise the same sequences that code for the active sites etc, as the subject sequence. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences, % homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps, "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons.

Calculation of maximum % homology therefore firstly requires the production of an optimal alignment, taking into consideration gap penalties. A suitable computer program for carrying out such an alignment is the Vector NTI Advance™ 11 (Invitrogen Corp). Examples of other software that can perform sequence comparisons include, but are not limited to, the BLAST package (see Ausubel et al 1999 Short Protocols in Molecular Biology, 4th Ed—Chapter 18), and FASTA (Altschul et al 1990 J. Mol. Biol. 403-410). Both BLAST and FASTA are available for offline and online searching (see Ausubel et al 1999, pages 7-58 to 7-60). However, for some applications, it is preferred to use the Vector NTI Advance™ 11 program, A new tool, called BLAST 2 Sequences is also available for comparing protein and nucleotide sequence (see FEMS Microbial Lett 1999 174(2): 247-50; and FEMS Microbial Lett 1999 177(1): 187-8.).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs, Vector NTI programs generally use either the public default values or a custom symbol comparison table if supplied (see user manual for further details). For some applications, it is preferred to use the default values for the Vector NTI Advance™ 11 package.

Alternatively, percentage homologies may be calculated using the multiple alignment feature in Vector NTI Advance™ 11 (Invitrogen Corp.), based on an algorithm, analogous to CLUSTAL (Higgins D G & Sharp P M (1988), Gene 73(1), 237-244). Once the software has produced an optimal alignment, it is possible to calculate % homology, preferably % sequence identity. The software typically does this as part of the sequence comparison and generates a numerical result.

Should Gap Penalties be used when determining sequence identity, then preferably the default parameters for the programme are used for pairwise alignment. For example, the following parameters are the current default parameters for pairwise alignment for BLAST 2:

| FOR BLAST2 | DNA | PROTEIN |
|---|---|---|
| EXPECT THRESHOLD | 10 | 10 |
| WORD SIZE | 11 | 3 |
| SCORING PARAMETERS | | |
| Match/Mismatch Scores | 2, −3 | n/a |
| Matrix | n/a | BLOSUM62 |
| Gap Costs | Existence: 5 | Existence: 11 |
| | Extension: 2 | Extension: 1 |

In one embodiment, preferably the sequence identity for the nucleotide sequences and/or amino acid sequences may be determined using BLAST2 (blastn) with the scoring parameters set as defined above.

For the purposes of the present invention, the degree of identity is based on the number of sequence elements which are the same. The degree of identity in accordance with the present invention for amino acid sequences may be suitably determined by means of computer programs known in the art such as Vector NTI Advance™ 11 (Invitrogen Corp.). For pairwise alignment the scoring parameters used are preferably BLOSUM62 with Gap existence penalty of 11 and Gap extension penalty of 1.

Suitably, the degree of identity with regard to a nucleotide sequence is determined over at least 20 contiguous nucleotides, preferably over at least 30 contiguous nucleotides, preferably over at least 40 contiguous nucleotides, preferably over at least 50 contiguous nucleotides, preferably over at least 60 contiguous nucleotides, preferably over at least 100 contiguous nucleotides. Suitably, the degree of identity with regard to a nucleotide sequence may be determined over the whole sequence.

Amino Acid Mutations

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar—uncharged | C S T M |
| | | N Q |
| | Polar—charged | D E |
| | | K R |
| AROMATIC | | H F W Y |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine. Replacements may also be made by unnatural amino acids.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134.

Nucleotide Sequences

Nucleotide sequences for use in the present invention or encoding a polypeptide having the specific properties defined herein may include within them synthetic or modified nucleotides, A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences.

The present invention also encompasses the use of nucleotide sequences that are complementary to the sequences discussed herein, or any derivative, fragment or derivative thereof. If the sequence is complementary to a fragment thereof then that sequence can be used as a probe to identify similar coding sequences in other organisms etc.

Polynucleotides which are not 100% homologous to the sequences of the present invention but fall within the scope of the invention can be obtained in a number of ways. Other variants of the sequences described herein may be obtained for example by probing DNA libraries made from a range of individuals, for example individuals from different populations. In addition, other viral/bacterial, or cellular homologues particularly cellular homologues found in plant cells, may be obtained and such homologues and fragments thereof in general will be capable of selectively hybridising to the sequences shown in the sequence listing herein, Such sequences may be obtained by probing cDNA libraries made from or genomic DNA libraries from other plant species, and probing such libraries with probes comprising all or part of any one of the sequences in the attached sequence listings under conditions of medium to high stringency. Similar considerations apply to obtaining species homologues and allelic variants of the polypeptide or nucleotide sequences of the invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences. This may be useful where for example silent codon sequence changes are required to optimise codon preferences for a particular host cell in which the polynucleotide sequences are being expressed. Other sequence changes may be desired in order to introduce restriction polypeptide recognition sites, or to alter the property or function of the polypeptides encoded by the polynucleotides.

Polynucleotides (nucleotide sequences) of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as DNA polynucleotides and probes according to the invention may be produced recombinantly, synthetically, or by any means available to those of skill in the art. They may also be cloned by standard techniques.

In general, primers will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. This will involve making a pair of primers (e.g. of about 15 to 30 nucleotides) flanking a region of the pyropheophytinase sequence which it is desired to clone, bringing the primers into contact with mRNA or cDNA obtained from a plant cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Pyropheophytinase Formulation and Dosage

Enzymes used in the methods of the invention, e.g. a pyropheophytinase, can be formulated or modified, e.g., chemically modified, to enhance oil solubility, stability, activity or for immobilization. For example, enzymes used in the methods of the invention can be formulated to be amphipathic or more lipophilic. For example, enzymes used in the methods of the invention can be encapsulated, e.g., in liposomes or gels, e.g., alginate hydrogels or alginate beads or equivalents. Enzymes used in the methods of the invention can be formulated in micellar systems, e.g., a ternary micellar (TMS) or reverse micellar system (RMS) medium. Enzymes used in the methods of the invention can be formulated as described in Yi (2002) J. of Molecular Catalysis B: Enzymatic, Vol. 19, pgs 319-325.

The enzymatic reactions of the methods of the invention, e.g. the step of contacting the composition with a pyropheophytinase, can be done in one reaction vessel or multiple vessels. In one aspect, the enzymatic reactions of the methods of the invention are done in a vegetable oil refining unit or plant. In one embodiment, an enzyme having pyropheophytinase activity is added to the composition, e.g. a vegetable oil.

The pyropheophytinase may be dosed into the composition, e.g. a vegetable oil, in any suitable amount. For example, the enzyme may be dosed in a range of about 0.0001 to 1 U/g of the composition, preferably 0001 to 0.1 U/g, e.g. 0.005 to 0.01 U/g of the composition (e.g. vegetable oil). Notably one unit is defined in accordance with the "enzyme activity (pheophytinase and phyropheophytinase activity) assay" taught in the Examples below.

The method of the invention can be practiced with immobilized enzymes, e.g. an immobilized pyropheophytinase. The enzyme can be immobilized on any organic or inorganic support. Exemplary inorganic supports include alumina, celite, Dowex-1-chloride, glass beads and silica gel. Exemplary organic supports include DEAE-cellulose, alginate hydrogels or alginate beads or equivalents. In various aspects of the invention, immobilization of the pheophytinase can be optimized by physical adsorption on to the inorganic support. Enzymes used to practice the invention can be immobilized in different media, including water, Tris-HCl buffer solution and a ternary micellar system containing Tris-HCl buffer solution, hexane and surfactant. The enzyme can be immobilized to any type of substrate, e.g. filters, fibers, columns, beads, colloids, gels, hydrogels, meshes and the like.

Enzyme Reaction Conditions

Suitably the composition (e.g. vegetable oil) may be incubated (or admixed) with the pyropheophytinase between about 5° C. to and about 100° C., more preferably between 10° C. to about 90° C., more preferably between about 15° C. to about 80° C., more preferably between about 20° C. to about 75° C., more preferably at about 30 to about 60° C., preferably at about 45 to about 55° C. In another embodiment, suitably the method and/or use according to the present invention may be carried out at below about 60° C., preferably below about 50° C., preferably below about 40° C. Preferably the temperature of the composition (e.g. vegetable oil) may be at the desired reaction temperature when the enzyme is admixed therewith.

The composition (e.g. vegetable oil) may be heated and/or cooled to the desired temperature before and/or during enzyme addition. Therefore in one embodiment it is envisaged that a further step of the process according to the present invention may be the cooling and/or heating of the composition (e.g. vegetable oil).

Suitably the reaction time (i.e. the time period in which the admixture is held), preferably with agitation, is for a sufficient period of time to allow hydrolysis of pyropheophytin to form pyropheophorbide and phytol. For example, the reaction time may be at least about 1 minute, more preferable at least about 5 minutes, more preferably at least about 10 minutes. In some embodiments the reaction time may be between about 15 minutes to about 6 hours, preferably between about 15 minutes to about 60 minutes, preferably about 30 to about 120 minutes. In some embodiments, the reaction time may up to 6 hours.

Preferably the process is carried out between about pH 4.0 and about pH 10.0, more preferably between about pH 5.0 and about pH 10.0, more preferably between about pH 6.0 and about pH 10.0, more preferably between about pH 5.0 and about pH 7.0, more preferably between about pH 5.0 and about pH6.5, more preferably between about pH 6.5 and about pH 7.5, e.g. at about pH 7.0 (i.e. neutral pH). In one embodiment preferably the process is carried out between about pH 5.5 and pH 6.0.

Suitably the water content of the composition (e.g. vegetable oil) when incubated (or admixed) with the pyropheophytinase is between about 0.5 to about 5% water, more preferably between about 1 to about 3% and more preferably between about 1.5 and about 2%.

When an immobilised enzyme is used, suitably the water activity of the immobilised enzyme may be in the range of about 0.2 to about 0.98, preferably between about 0.4 to about 0.9, more preferably between about 0.6 to about 0.8.

Processing and Refining of Plant (Vegetable) Oils

In one embodiment, the method of the present invention may be used in the enzymatic processing of plant-derived oils. In a typical vegetable oil processing method, oil is extracted in hexane, the crude vegetable oil is degummed, (optionally, caustic neutralized), bleached using, e.g. clay adsorption with subsequent clay disposal, and deodorized to produce refined, bleached and deodorized or RBD oil. The need for the degumming step depends on phosphorus content and other factors (all known in the art).

In embodiments of the present invention, an enzymatic reaction involving application of the pyropheophytinase may be performed at various stages of this method. For example, the pyropheophytinase may be contacted with the crude oil, during a degumming step, or in a bleaching step (e.g. in place of clay bleaching) following degumming.

Silica Treatment

Thus in one embodiment of the invention, the process comprises degumming a crude vegetable oil, bleaching using an enzyme having pyropheophytinase activity, followed by deodorization. Preferably the method comprises a step of silica treatment, especially subsequent to the pyropheophytinase treatment. For example, the method may comprise use of an adsorbent-free or reduced adsorbent silica refining devices and processes, which are known in the art, e.g., using TriSyl Silica Refining Processes (Grace Davison, Columbia, Md.), or, SORBSIL R™ silicas (INEOS Silicas, Joliet, Ill.).

Unlike chlorophyllide, pyropheophorbide (and pheophorbide) are less water soluble and are not particularly suited to removal by an aqueous extraction step. The silica treatment step is particularly suitable for removing pyropheophorbide (and also pheophorbide) produced by the action of the pyropheophytinase. Pyropheophorbide (and pheophorbide) may also be removed by the deodorization step. Preferably the process comprises both a deodorization step and a silica treatment step.

More preferably the process comprises a two-stage silica treatment, e.g. comprising two silica treatment steps separated by a separation step in which the silica is removed, e.g. a filtration step. The silica treatment is preferably performed at elevated temperature, e.g. at above about 30° C., more preferably about 50 to 150° C., about 70 to 110° C., about 80 to 100° C. or about 85 to 95° C., most preferably about 90° C., Degumming and Oil Refining The methods can be used in conjunction with processes based on extraction with hexane and/or with subsequent refining of the crude extracts to edible oils. For instance the methods of the present invention can be used in conjunction with enzyme assisted oil extraction (see Journal of Americal Oil Chemists' Society (2006), 83 (11), 973-979). The first step in the refining sequence is the so-called "degumming" process, which serves to separate phosphatides by the addition of water. The material precipitated by degumming is separated and further processed to mixtures of lecithins. The commercial lecithins, such as soybean lecithin and sunflower lecithin, are semi-solid or very viscous materials. They consist of a mixture of polar lipids, mainly phospholipids, and oil, mainly triglycerides. The methods of the invention can be used before or after any step in this process, or before or after any combination of steps, or before or after all of the steps, in a process, e.g., prior to, during or following mechanical and/or chemical extraction, degumming and/or bleaching and the like.

The methods of the invention can be used in any degumming procedure, including water degumming, ALCON oil degumming (e.g., for soybeans), safinco degumming, "super degumming," UF degumming, TOP degumming, uni-degumming, dry degumming and ENZYMAX™ degumming. See e.g. U.S. Pat. Nos. 6,355,693; 6,162,623; 6,103,505; 6,001,640; 5,558,781; 5,264,367.

The methods of the invention can be used in any oil processing method, e.g., degumming or equivalent processes. For example, methods of the invention can be used in processes as described in U.S. Pat. Nos. 5,558,781; 5,288,619; 5,264,367; 6,001,640; 6,376,689; WO 0229022; WO 2006009676; oil degumming as described, e.g., in WO 98118912; and the like. Various degumming procedures incorporated by the methods of the invention are described in Bockisch, M. (1998), Fats and Oils Handbook, The extraction of Vegetable Oils (Chapter 5), 345-445, AOCS Press, Champaign, Ill.

Further Oil Processing Steps

Following an enzymatic treatment step using a pyropheophytinase according to the present invention, in one embodiment the treated liquid (e.g. oil) is separated with an appropriate means such as a centrifugal separator and the processed oil is obtained. Upon completion of the enzyme treatment, if necessary, the processed oil can be additionally washed with water or organic or inorganic acid such as, e.g., acetic acid, phosphoric acid, succinic acid, and the like, or with salt solutions.

Methods of the invention also can be practiced using processes as described in U.S. Pat. No. 5,315,021. For example, in one aspect, the methods of the invention can be practiced with processes for removing color impurities other than pyropheophtyinase from vegetable oils, for instance for removing chlorophyll, pheophytin and derivatives thereof. For instance in one embodiment, the processes can comprise dispersing a source of phosphoric acid in vegetable oil to form a mixture having a moisture content of less than 0.1% by weight which mixture is maintained at a temperature in the range of 70° C. to 160° C. until a precipitate containing chlorophyll color impurities is formed. This can be followed by separating the precipitated material from the oil to remove the chlorophyll color impurities with the precipitated material, e.g. during conventional oil processing up to and including the removal of bleaching clay from the oil.

Chlorophyllase Treatment

In one embodiment, the method (e.g. a vegetable oil processing method) may further comprise a step of contacting the composition with a chlorophyllase, for example using a method as described in WO 2006009676. For example, in one aspect, the method may comprise a step of enzymatically treating chlorophyll-containing or chlorophyll-contaminated compositions by hydrolyzing chlorophyll to phytol and chlorophyllide. Any chlorophyllase, chlase or chlorophyll chlorophyllido-hydrolyase or polypeptide having a similar activity (e.g., chlorophyll-chlorophyllido hydrolase 1 or chlase 1, or, chlorophyll-chlorophyllido hydrolase 2 or chlase 2, see, e.g. NCBI P59677-1 and P59678, respectively) can be used in this step of the method of the invention.

Any polypeptide that catalyses the hydrolysis of a chlorophyll ester bond to yield chlorophyllide and phytol can be used in this step of the method of the invention. In one embodiment the enzyme is a chlorophyllase classified under the Enzyme Nomenclature classification (E.C. 3.1.1.14). Any isolated, recombinant or synthetic or chimeric (a combination of synthetic and recombinant) polypeptide (e.g., enzyme or catalytic antibody) can be used, see e.g. Marchler-Bauer (2003) Nucleic Acids Res, 31: 383-387. In one aspect, the chlorophyllase may be an enzyme as described in WO 0229022 or WO 2006009676. For example, the *Arabidopsis thaliana* chlorophyllase can be used as described, e.g. in NCBI entry NM_123753. Thus the chlorophyllase may be a polypeptide comprising the sequence of SEQ ID NO:20 shown in FIG. 22b. In another embodiment, the chlorophyllase is derived from algae, e.g. from *Phaeodactylum tricornutum*.

As described in WO 2006009676, chlorophyllide may be removed by an aqueous separation step and/or silica treatment. The method can further comprise modifying pH (e.g. increasing pH) to promote aqueous separation of chlorophyllide. Thus, the methods of the invention can also comprise a caustic neutralization processes, e.g., with caustic-neutralized pH conditions. In one aspect, the compositions and methods of the invention comprise a neutralization step.

Further Enzyme Treatments

In further aspects, the processes of the invention further comprise use of lipid acyltransferases, phospholipases, proteases, phosphatases, phytases, xylanases, amylases (e.g. α-amylases), glucanases, polygalacturonases, galactolipases, cellulases, hemicellulases, pectinases and other plant cell wall degrading enzymes, as well as mixed enzyme preparations and cell lysates. In alternative aspects, the processes of the invention can be practiced in conjunction with other processes, e.g., enzymatic treatments, e.g., with carbohydrases, including cellulase, hemicellulase and other side degrading activities, or, chemical processes, e.g., hexane extraction of soybean oil. In one embodiment the method of the present invention can be practiced in combination with a method as defined in WO 2006031699.

In one aspect, the methods of the invention can be practiced with methods as described in U.S. Pat. No. 6,376,689. For example, in one aspect, the compositions and methods of the invention can comprise a single-step acid degumming/decolorizing process that removes pyropheophytin, and optionally pyropheophytin derivatives, pheophytin, chlorophyll and related compounds, from vegetable oils from seeds, especially frost damaged seeds which have large amounts of chlorophyll-type compounds. In one aspect, the methods of the invention further comprise a mixture of aqueous sulfuric and phosphoric acids that is blended with the oil to remove chlorophyll-type compounds from the oil.

Plant Oil Processing Apparatus and Methods

In a further aspect, the present invention provides an apparatus for the enzymatic treatment of pyropheophytin-containing compositions comprising (a) a plant (e.g. vegetable) oil refining apparatus; and (b) a polypeptide having a pyropheophytinase activity operably integrated into the plant (e.g. vegetable) oil refining apparatus. Typically the polypeptide having pyropheophytinase activity is integrated into the apparatus such that it is capable of hydrolyzing pyropheophytin during processing of the pyropheophytin-containing composition (e.g. a vegetable oil).

The apparatus may comprise any suitable vegetable oil refining apparatus or combination thereof, e.g. an oil leaving expellor (e.g. from Pennwalt Corp.), or a gravitational gum separation device. The apparatus may comprise immobilized enzymes, e.g., an immobilized pyropheophytinase and optionally an immobilized chlorophyllase. For example the apparatus may comprise a silica-immobilized pyropheophytinase. In one embodiment the silica comprises a silica gel or equivalent, e.g. a TriSyl Silica or a SORBSIL R™ silica. The apparatus may further comprise means for adjusting pH, e.g. increasing pH (caustic treatment), and then, alternatively, neutralizing pH.

Figure 24:
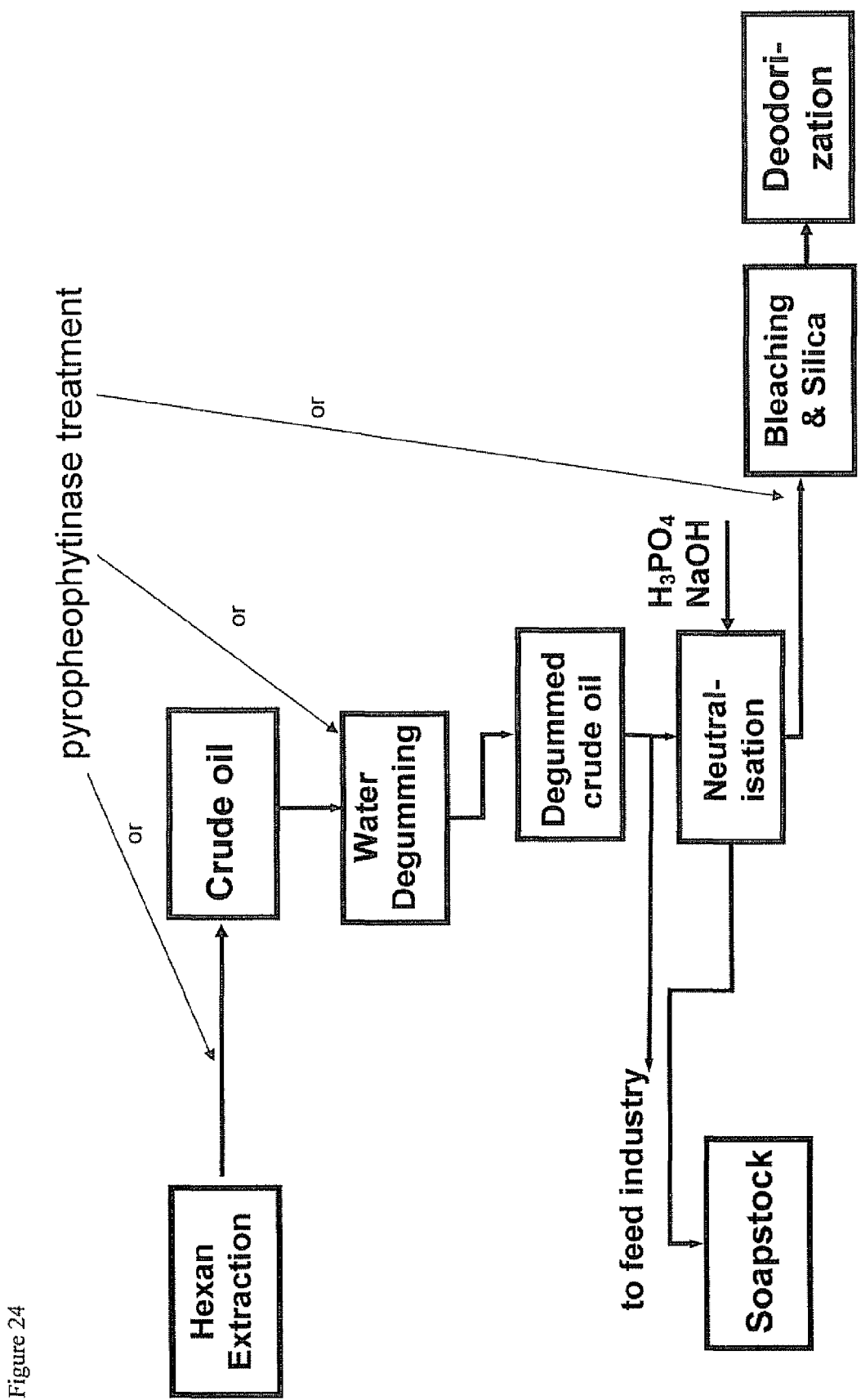
FIG. 24 is a diagrammatic representation of an oil refining process according to the present invention.

In one embodiment, the method of the present invention may be performed in an oil refining process exemplified by FIG. 24. The first stage of this process comprises hexane extraction to form crude oil, followed by water degumming, caustic neutralization, bleaching, silica treatment and deodorization. As shown in FIG. 24, pyropheophytinase treatment may be applied at various stages of this process, including to the crude oil, during water degumming, or before silica treatment. The degumming can be a "traditional" or an enzymatic degumming, e.g. involving phospholipid hydration and/or hydrolysis.

In the method as exemplified by FIG. 24, a chlorophyllase may also be used, and the chlorophyllase treatment may take place at the same stage as pyropheophytinase treatment or at a different stage. The pyropheophytinase (and optional chlorophyllase) treatment may be considered to be an enzymatic bleaching step, and may replace a traditional clay adsorption bleaching step. In one aspect, the exemplary process of the invention comprises a subsequent aqueous separation step to remove the reaction products of chlorophyllase treatment, gum and/or soap.

In an alternative embodiment, the pyropheophytinase treatment may be applied to an oilseed preparation before performing the processing steps shown in FIG. 24, i.e. before hexane extraction.

Figure 25:
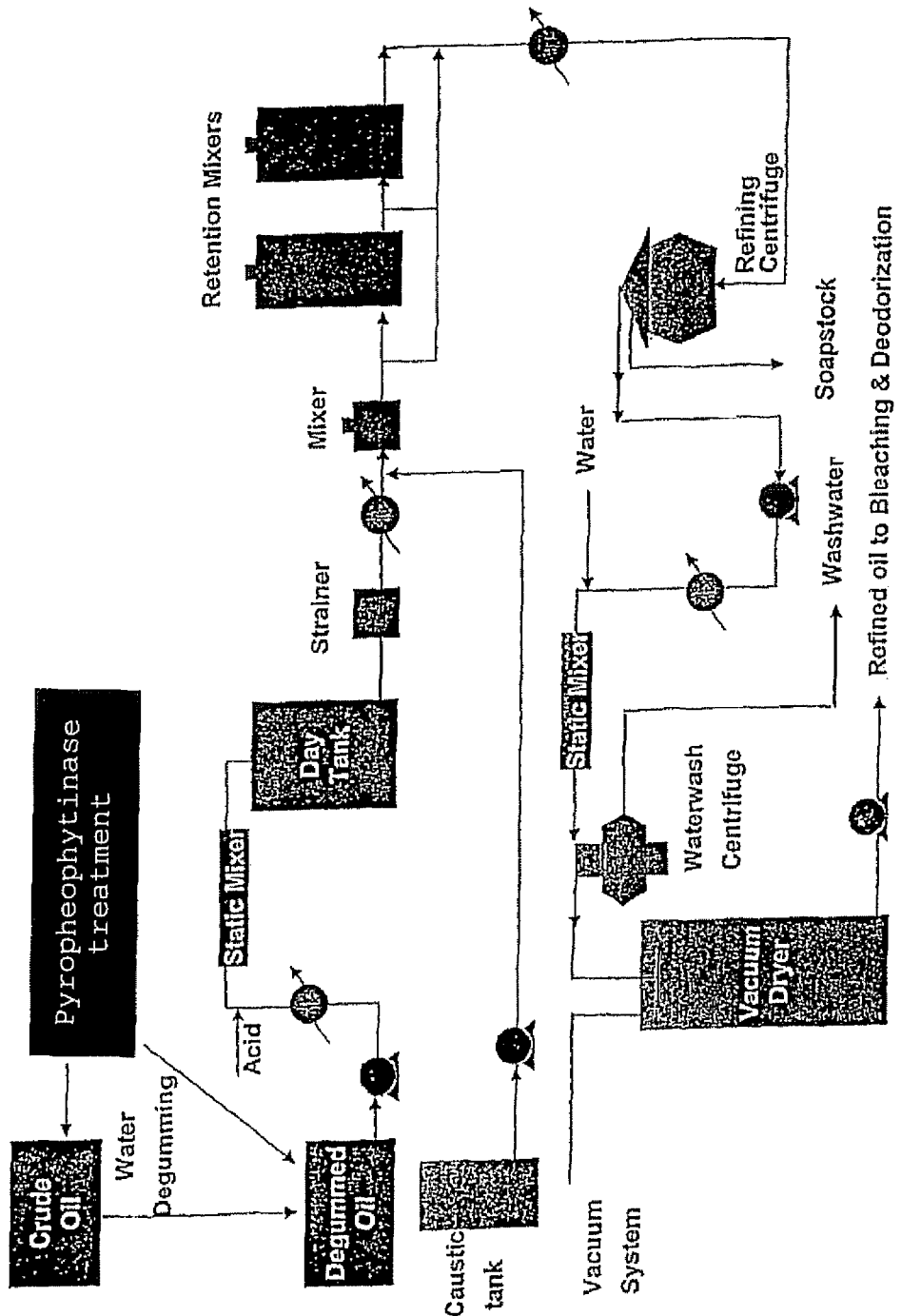
FIG. 25 is a diagrammatic representation of a vegetable oil refining process and apparatus according to the present invention.

FIG. 25 illustrates another embodiment of a method and apparatus according to the present invention. FIG. 25 illustrates various aspects of a vegetable oil refining apparatus, including components such as a degumming tank, static mixer, day tank, caustic tank, strainer, retention mixers, refining centrifuge, water wash centrifuge and vacuum dryer. The enzyme of the present invention having pyropheophytinase activity can be used in one or several or all of the following steps: added to the crude oil, in the degumming process or in the degummed oil, added to a storage or holding tank, a caustic tank, and/or a retention mixer. For example, in particular embodiments pyropheophytinase immobilized on silica may be added to the day tank or retention mixers.

The invention will be further described with reference to the following examples; however, it is to be understood that the invention is not limited to such examples.

EXAMPLES

In the following examples, a pheophytinase from *Arabidopsis thaliana* is expressed by recombinant DNA methods and a pheophytinase enzyme is isolated which has activity on both pheophytin and pyropheophytin in vegetable oils. Pheophorbide and pyropheophorbide produced in the oil by pheophytinase/pyropheophytinase activity can then be removed by steps such as adsorption to silica and/or by deodorization. Silica is very efficient in removing the polar degradation products pheophorbide and pyropheophorbide.

Materials

The enzyme used is pheophytinase from *Arabidopsis thaliana*, (At PPH), GenBank ID 15240707, in an aqueous solution containing 5 Units/ml pheophytinase.

Pheophytinase is immobilized on silica according to the following procedure. 3.0 g silica, (Sigma S5505 or Trisyl 300 from Grace Davison) is added to 6 ml of the obtained pheophytinase (cell extract) and stirred for 2 hours at room temperature. The silica is recovered by 10 minutes centrifugation at 3000 g. The pelleted silica is washed twice with demineralized water.

Crude rape seed oil from Scanola DK, containing 7 ppm pheophytin and 5 ppm pyropheophytin is used as the oil.

Pheophytin is produced from spinach chlorophyll by acid treatment according to "Extraction, Purification, and Characterization of Chlorophylls from Spinach Leaves," Journal of Agricultural and Food Chemistry 40.2 (1992): 215-220. Pheophytin (0.98 mg/ml) is dissolved in acetone.

Pyropheophytin (0.5 mg/ml) is produced from pheophytin dissolved in pyridine by heat treatment at 100° C. according to "Determination of chlorophylls and their derivatives in Gynostemma pentaphyllum Makino by liquid chromatography-mass spectrometry.", Journal of Pharmaceutical and Biomedical Analysis 48.1 (2008): 105-12. Pheophorbide and pyropheophorbide are obtained from Frontier Scientific.

Analytical Methods

HPLC analysis is performed according to the following conditions, and generally as described in "Determination of chlorophylls and carotenoids by high-performance liquid chromatography during olive lactic fermentation", Journal of Chromatography, 585, 1991, 259-266.

Stock solutions of chlorophylls A and B are prepared as follows. 5 mg Chlorophyll A, from *Anacystis nidulans* algae, is dissolved in 5 ml acetone, 5 mg Chlorophyll B, from spinach (Sigma Life Science 25740) is dissolved in 5 ml acetone. Each chlorophyll solution is transferred to a 5 ml volumetric flask, distributed to 10 vials with 500 μl in each, and stored frozen. 200 μl of each stock solution of chlorophylls A and B is added to 20 ml acetone, and 1 μl of the resultant solution added to 10 ml acetone to provide a control solution for HPLC.

Pheophytin in the oil samples was concentrated according to a solid-phase extraction procedure performed generally as described in "Routine and sensitive SPE-HPLC method for quantitative determination of pheophytin a and pyropheophytin a in olive oils", Food Research International, 38, 2005, 1067-1072, using Sep-Pak®*Plus tC18 Environmental Cartridges (WAT036800), 900 mg, 17% Carbon Load.

Two tC18 cartridges are fitted in tandem (2×900 mg, hold-up volumes ~3 ml). The tC18 cartridges are conditioned with 5 ml petroleum ether (40-60° C. quality), without allowing the column to dry. A 1 ml oil sample is drawn into a 2 ml disposable syringe and pressed sample through the tC18 cartridges. The cartridges are washed with 12 ml petroleum ether (using a 10 ml disposable syringe).

The chlorophyll derivatives are eluted with 6 ml acetone (using a 5 ml disposable syringe). The acetone solution is evaporated to dryness under nitrogen. The temp is kept at 50-60° C. The extracted sample is reconstituted in 0.5 ml acetone and centrifuged at 4500 rpm/3260 rcf for 5 minutes. The sample is transferred to a vial with insert and analysed.

Pheophorbide and pyropheophorbide in the oil samples were concentrated according to a solid-phase extraction procedure performed using IST Isolute™ SPE Columns, (460-0050-B), Silica, 500 mg. The method is performed essentially as for tC18 cartridges except that cyclohexane is used in place of petroleum ether.

Figure 1:
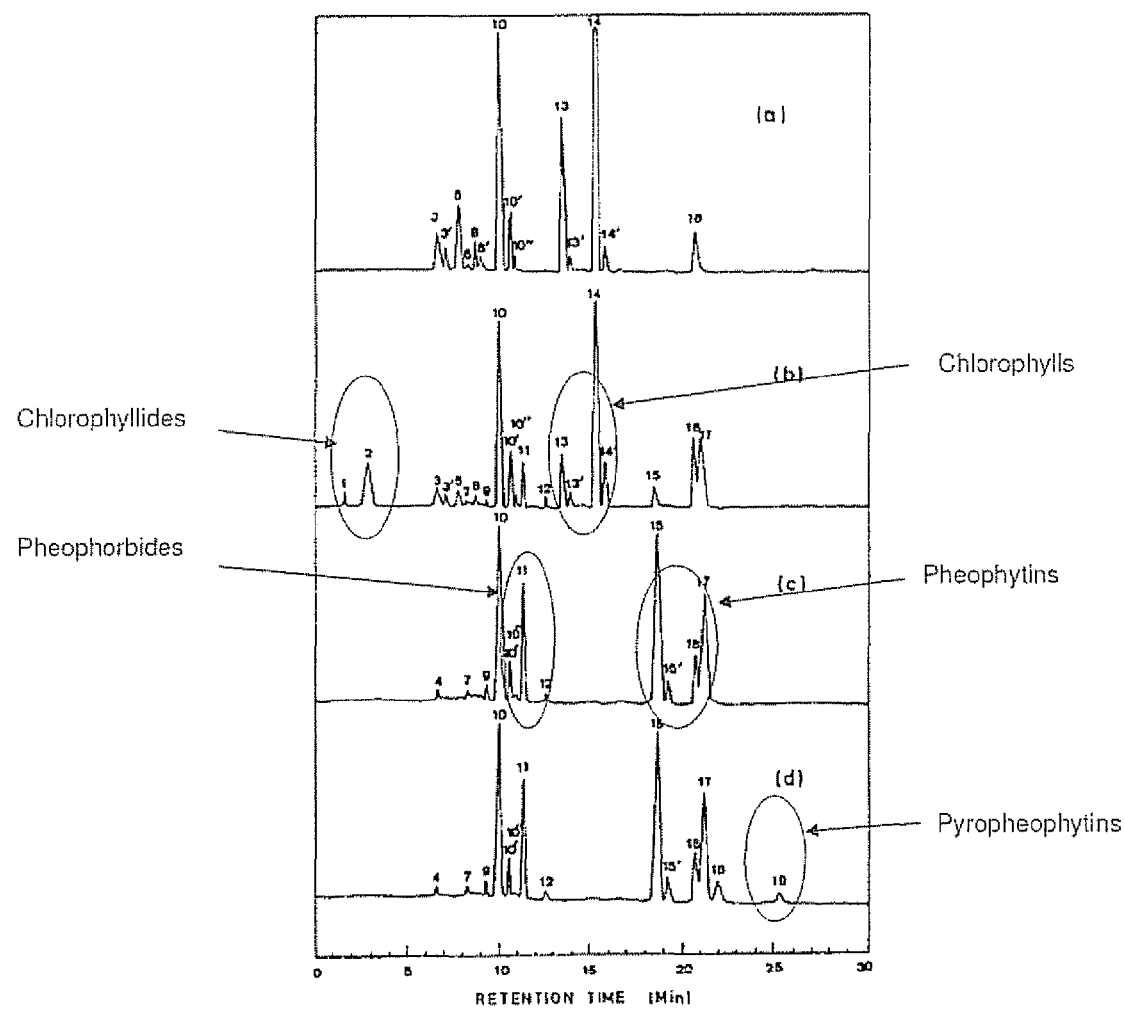
Figure 2:
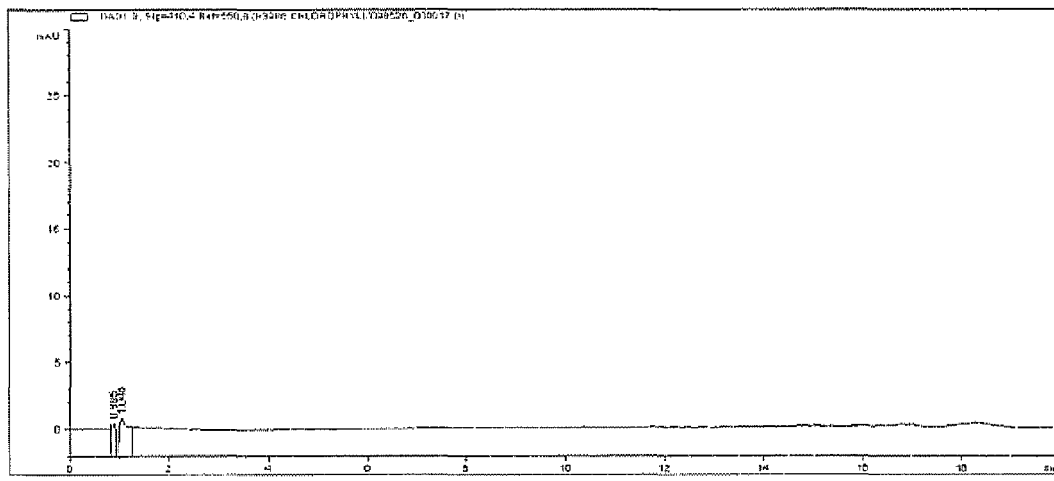
FIG. 2 shows the results of HPLC analysis of sample 1 as defined in Table 5 (Control) before deodorization.
Figure 3:
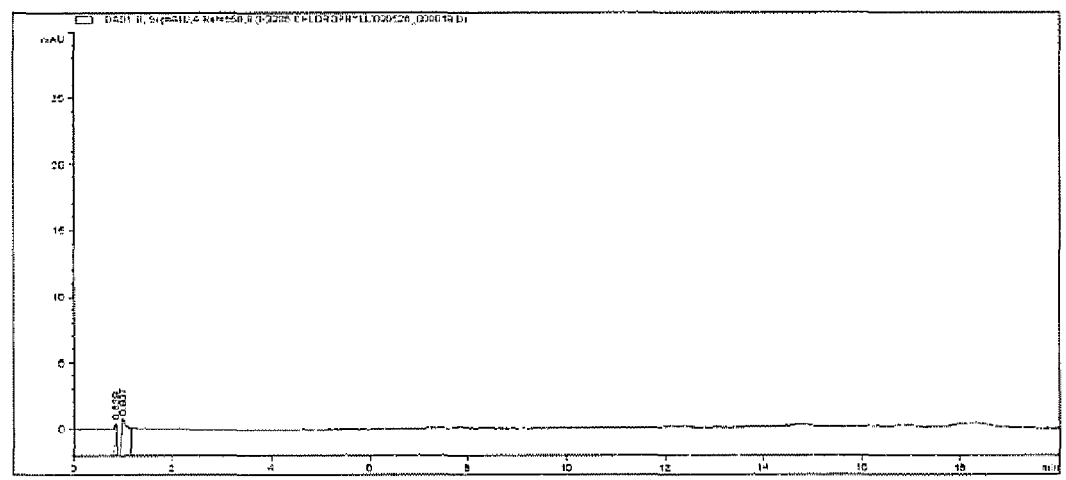
FIG. 3 shows the results of HPLC analysis of sample 1 as defined in Table 5 (Control) after deodorization.
Figure 4:
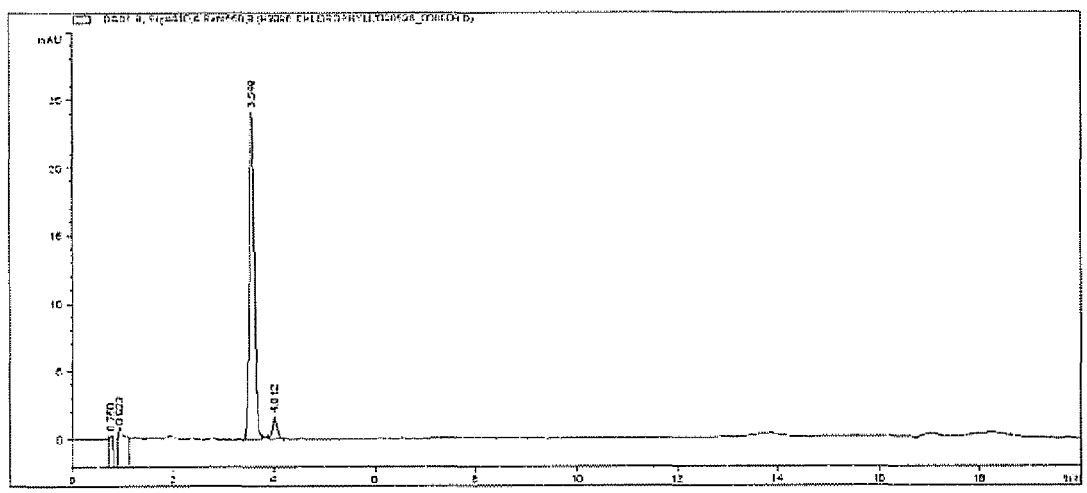
FIG. 4 shows the results of HPLC analysis of sample 2 as defined in Table 5 (comprising pheophorbide) before deodorization.
Figure 5:
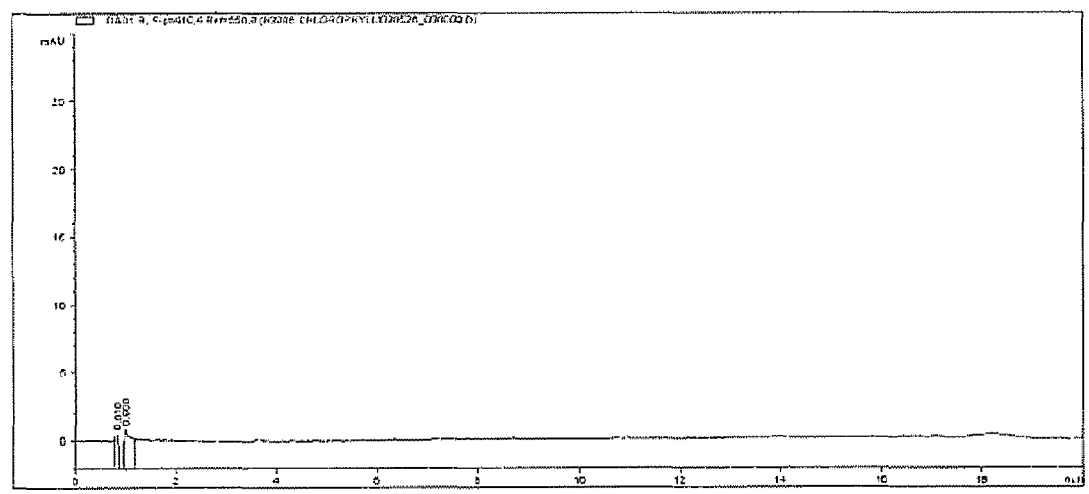
FIG. 5 shows the results of HPLC analysis of sample 2 as defined in Table 5 (comprising pheophorbide) after deodorization.
Figure 6:
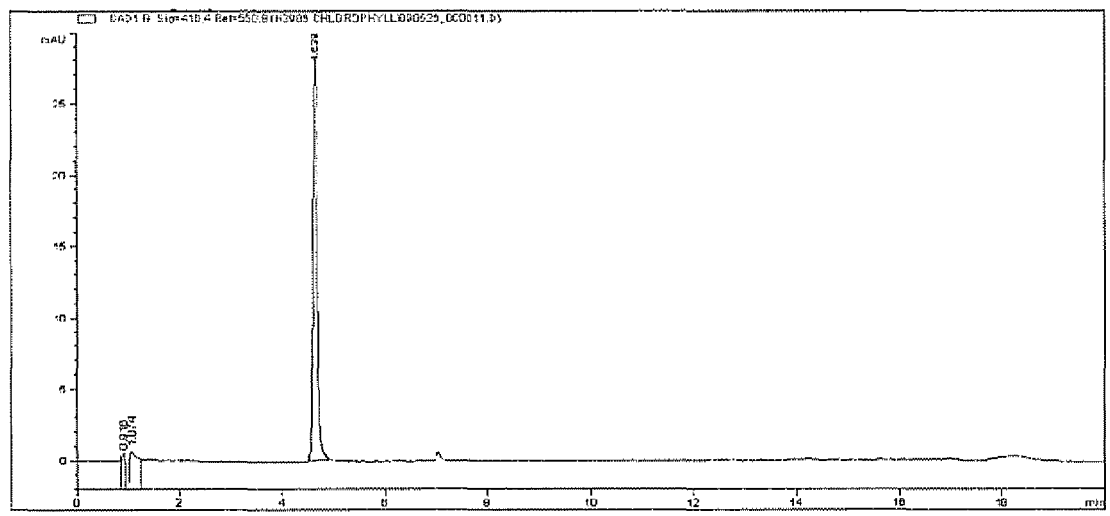
FIG. 6 shows the results of HPLC analysis of sample 3 as defined in Table 5 (comprising pyropheophorbide) before deodorization.
Figure 7:
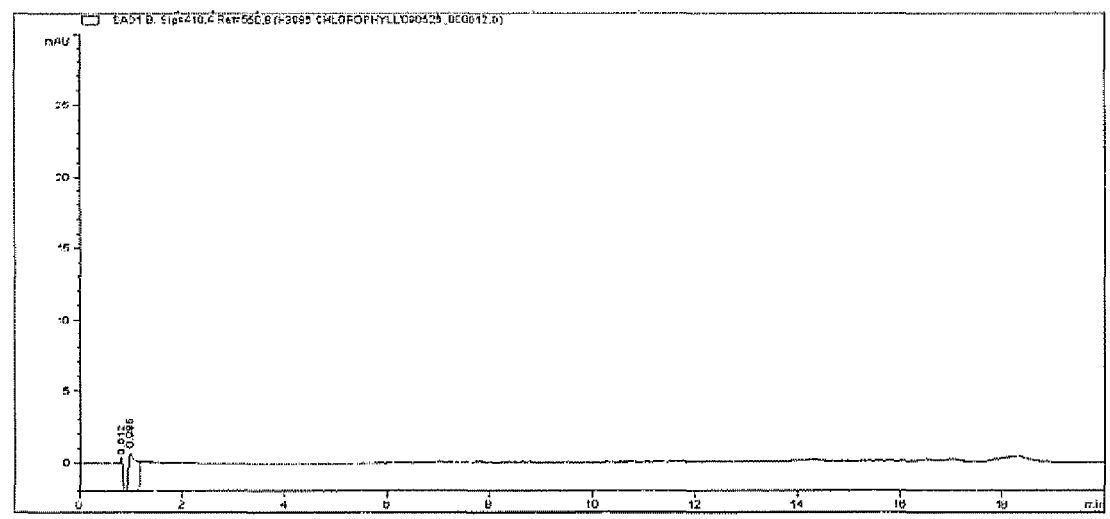
FIG. 7 shows the results of HPLC analysis of sample 3 as defined in Table 5 (comprising pyropheophorbide) after deodorization.
Figure 8:
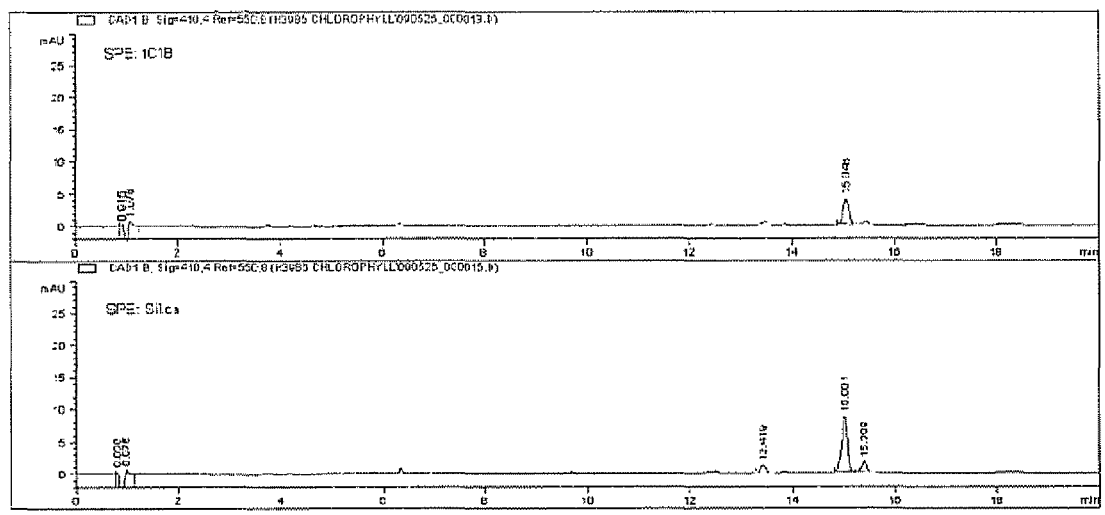
FIG. 8 shows the results of HPLC analysis of sample 4 as defined in Table 5 (comprising pheophytin) before deodorization.
Figure 9:
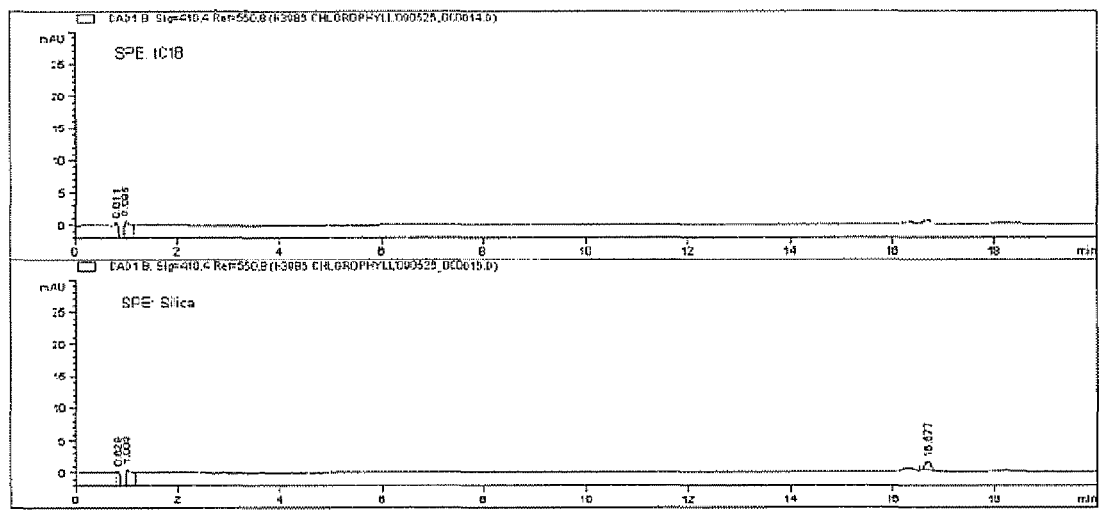
FIG. 9 shows the results of HPLC analysis of sample 4 as defined in Table 5 (comprising pheophytin) after deodorization.

An example of a representative HPLC chromatogram (from Journal of Chromatography, 585, 1991, 259-266) and the assignment of peaks are given in FIG. 1.

| | Chromatographic Conditions | | | |
|---|---|---|---|---|
| System | Hewlett Packard 1100A (DU6; Pu9) | | | |
| Column | Zorbax SB-C18 3.5 μm (#576) | LxD: 150 * 3.0 mm id. | | Temp: 30° C. (CH) |
| Injector | Hewlett Packard 1100B Auto Sampler (AS8) | | | Vol.: 5 μl |
| Detector | Hewlett Packard DAD 1100A (D8) | | | DAD λ: 410 nm, bw 4 nm |
| | | | | 430 nm, bw 4 nm |
| | | | | Ref λ: 550 nm, bw 8 nm |
| Integrator | Agilent Chemstation | | | Method: CHLOROPHYLL_03.M |
| | | | | Sequence: H3986_00 &01.S |
| Mobile phase | A: Water:1M Ammonium Acetate:Methanol (1:1:8 v/v) | | | Flow: 0.8 ml/min |
| | B: Acetone:Methanol (1:1 v/v) | | | Pressure: 250→280 bar (at start) |
| Gradient | Time | Flow | % B | |
| | 0 | 0.8 | 25 | New injection |
| | 5 | 0.8 | 75 | |
| | 6.5 | 0.8 | 75 | |
| | 15 | 0.8 | 100 | |
| | 16 | 0.8 | 25 | |
| | 22 | 0.8 | 25 | |
| Column care | Column cleaning/storing: | | | |
| Classification | T—Toxic | | | R: 36-39/23/24/25-66-67 |
| of MP (R/S) | F—Highly flammable | | | S: 7-26-45-36/37 |

Enzyme Activity (Pheophytinase or Pyropheophytinase Activity) Assay

170 µl mM HEPES, pH 7.0 is added 20 µl 0.3 mM pheophytin or pyropheophytin dissolved in acetone. The enzyme is dissolved in 50 mM HEPES, pH 7.0. 10 µl enzyme solution is added to 190 µl substrate solution to initiate the reaction and incubated at 25° C. for various time periods. The reaction was stopped by addition of 350 µl acetone. Following centrifugation (2 min at 18,000 g) the supernatant was analyzed by HPLC, and the amounts of pheophytin and pheophorbide or pyropheophytin and pyropheophorbide determined. One unit of enzyme activity for pheophytinase activity is defined as one micromole of hydrolyzed pheophytin per minute. One unit of enzyme activity for pyropheophytinase activity is defined as one micromole of hydrolyzed pyropheophytin per min.

Example 1

Expression of Pheophytin Pheophorbide Hydrolase (Pheophytinase) in *Trichoderma reesei*

The amino acid sequence (Protein accession BAH19780) encoded by the gene AT5G13800 from *Arabidopsis thaliana*, was retrieved from the NCBI sequence database: at the website of National Center for Biotechnology Information, U.S. National Library of Medicine, National Institutes of Health, search "AT5G13800" within the database of "protein." The sequence is shown in FIG. 10 (SEQ ID NO:1). The AT5G13800 gene encodes a protein of 484 amino acids in length consisting of the mature protein of 438 amino acids and an N-terminal chloroplast transit peptide of 46 residues. The chloroplast transit peptide is shown in bold in FIG. 10. The protein has been characterized as a Pheophytin Pheophorbide Hydrolase (Pheophytinase=PPH), Plant Cell. 2009, 21(3):767-785.

For heterologous expression of this gene, a synthetic PPH gene (FIG. 12) with codons optimized for expression in *Trichoderma reesei* was synthesized. The N-terminal transit peptide was replaced by a kexin linker (shown in bold in FIG. 12), an octapeptide TSVAVEKR (SEQ ID NO: 27). The nucleotide sequence (SEQ ID NO:3) and amino acid sequence (SEQ ID NO:4) of the synthetic PPH gene and polypeptide are shown in FIG. 12.

Figure 13:
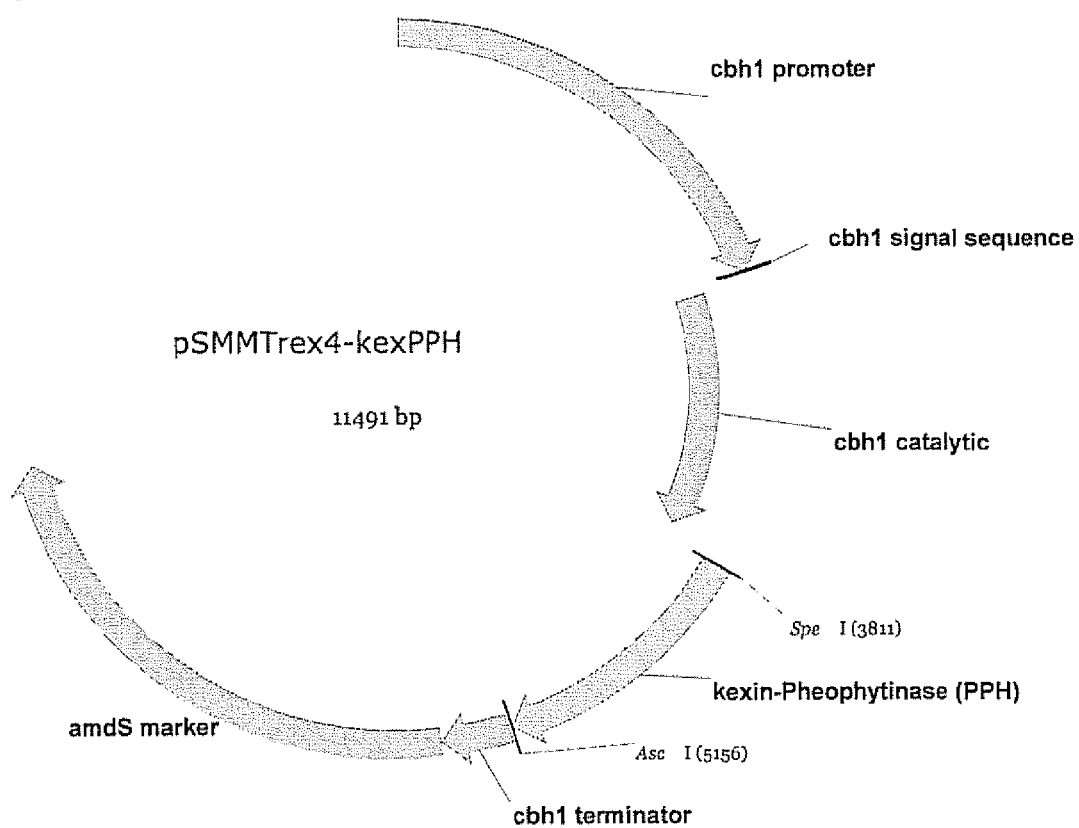
FIG. 13 shows an expression construct containing a synthetic pheophytinase (PPH) gene fused to the catalytic core of cbh1 via a kexin octapeptide linker.

A fusion construct was made consisting of the cellobiohydrolase 1 (cbh1) catalytic core fused to the mature pheophytinase protein via the kexin linker. The expression construct shown in FIG. 13, pSMMTrex4-kexPPH, was made by restriction digestion of the synthetic PPH gene using restriction enzymes Spe1 & Asc1 and isolating this fragment to be used as insert. The Spe1/Asc1 cut and alkaline phosphatase-treated *Trichoderma* vector Trex4, was used in a ligation reaction. The final expression cassette pSMMTrex4-kexPPH contains the promoter and terminator regions of the *T. reesei* cellobiohydrolase 1 (cbh1) gene flanking the PPH synthetic gene, at the 5' and 3' end, respectively. It also contains the *Aspergillus nidulans* acetamidase, amdS gene as selectable marker for transformation of *T. reesei*.

Two other expression constructs were made by fusing the synthetic gene encoding the mature PPH protein directly to two different signal peptides, namely the cellobiohydrolase 1 (cbh1) signal peptide and the *Aspergillus tubigensis* lipase 3 prepro-signal sequence.

The strain used for transformation is *Trichoderma reesei*, a derivative of the non-GMM strain RL-P37 from which the genes encoding the two secreted cellobiohydrolases, CBHI and CBHII, and two of the secreted endoglucanases, EGI and EGII, have been deleted.

Transformation of *T. reesei* Quad Delete Host Strain

The expression construct, pSMMTrex4-kexPPH, containing the *A. thaliana* pheophytinase gene was transformed into a *T. reesei* by biolistic transformation using the PDS-1000 Helium system (BioRad Cat. No. 165-02257).

A suspension of spores from a quad deleted strain of *T. reesei* was prepared. 200 µl of spore suspension was spread onto the center of the minimal medium (MM) acetamide plates. MM acetamide plates had the following composition: 0.6 g/l acetamide; 1.68 g/l CsCl; 20 g/l glucose; 20 g/l $KH_2PO_4$, 0.6 g/l $CaCl_2$ $2H_2O$; 1 ml/l 1000× trace elements solution; 20 g/l Noble agar, and pH5.5, 1000× trace elements solution contained 5.0 g/l $FeSO_4$ $7H_2O$; 1.6 g/l $MnSO_4$; 1.4 g/l $ZnSO_4$ $7H_2O$ and 1.0 g/l $CoCl_2$ $6H_2O$. The spore suspension was allowed to dry on the surface of MM acetamide medium for 1 hour in the sterile hood. Transformation followed the manufacturer's instruction. 60 mg of tungsten particles were placed in a microfuge tube. 1 ml of ethanol was added and allowed to stand for 15 seconds. The ethanol was removed and the particles were washed three times with sterile $dH_2O$ before 250 µl of 50% (v/v) sterile glycerol was added. 25 µl of tungsten particle suspension was placed onto a microfuge tube. While continuously vortexing, the following were added: 5 µl (100-200 ng/µl) of plasmid DNA, 25 µl of 2.5M $CaCl_2$ and 10 µl of 0.1M spermidine. The particles were centrifuged for 3 seconds. The supernatant was removed and the particles were washed with 200 µl of 100% ethanol and centrifuged for 3 seconds. The supernatant was removed. 24 µl 100% ethanol was added and mixed by pipetting, then 8 µl aliquots of particles were removed and placed in the center of microcarrier disks that were held in a desiccator. Once the tungsten/DNA solution had dried the microcarrier disk was placed in the bombardment chamber along with the plate of MM acetamide with spores and the bombardment process was carried out according to the manufacturer's instructions. After bombardment of the plated spores with the tungsten DNA particles, the plates were incubated at 28° C. Transformed colonies were transferred to fresh plates of MM acetamide medium and incubated at 28° C.

Growth of Transformants

After 5 days of growth on MM acetamide plates, transformants obtained by biolistic transformation and displaying stable morphology were inoculated into 15 ml NREL-Trichoderma Glucose/Sophorose Defined media in a 50 ml shake flask. NREL-Trich Gluc/Soph Defined medium (per liter) consists of $(NH_4)_2SO_4$ 5 g, PIPPS buffer 33 g, Casamino Acids 9 g, $KH_2PO_4$ 4.5 g, $CaCl_2$ (Anhydrous) 1 g, $MgSO_4.7H_2O$ 1 g, pH to 5.50 adjusted with 50% NaOH with milli-Q $H_2O$ bring to 966.5 mL. After sterilization, the following were added: Mazu 5 mL, Glucose/Sophrose 60% 26 mL and 400× *T. reesei* Trace Metals 15 mL. The shake flask cultures were incubated with shaking at 28 C for 5 days.

Screening for Recombinant PPH Expression

Figure 14:
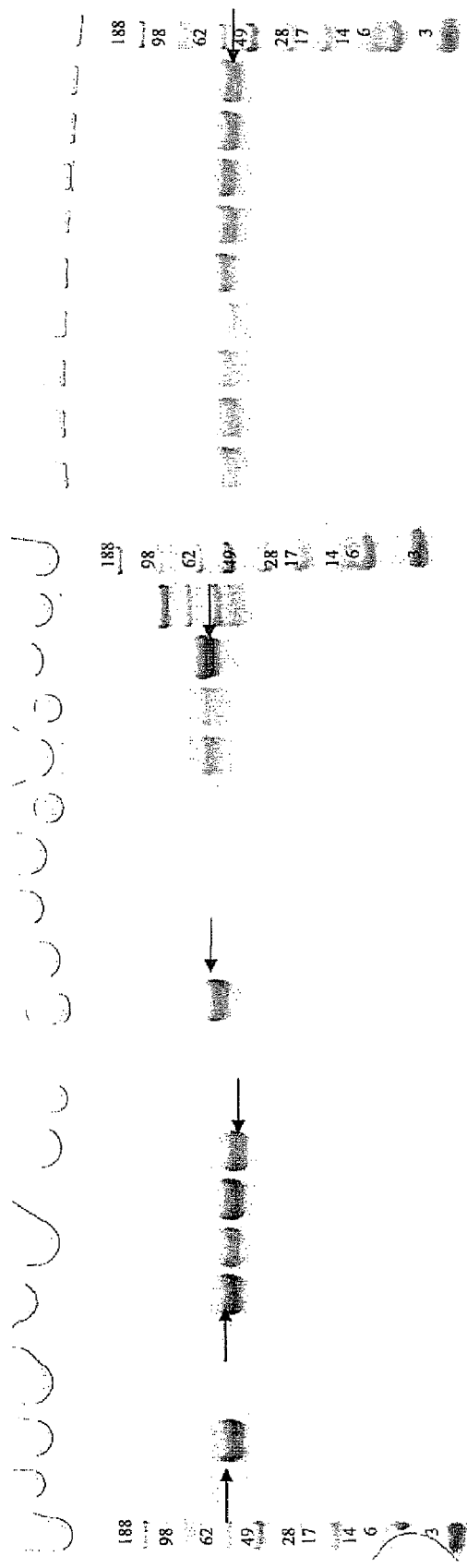
FIG. 14 shows SDS-PAGE of *Trichoderma reesei* transformants expressing PPH as a secreted protein in the culture supernatant.

Mycelium was removed by centrifugation and the supernatant was analysed for the presence of the recombinant PPH. The protein profile of the stable transformants was determined by SDS-PAGE using NuPAGE 4-12% and MES as running buffer. Samples of the supernatant were mixed with appropriate volume of 2× sample loading buffer with reducing agent. The gels were stained with Simply blue Safe stain (Invitrogen), FIG. 14 shows an SDS gel showing bands representing high levels of PPH protein expressed by transformants, within the molecular weight range of around 50-60 kDa. The strongly stained bands represents the 2 proteins, fusion partner cbh1 catalytic core & the lower band represents the PPH protein.

Presence of Other Putative PPH Proteins with High Sequence Identity to the *Arabidopsis thaliana* Pheophytinase.

Experiments were conducted to identify genes encoding enzymes with pheophytinase/pyropheophytinase activity in the sequence databases and identify signature motifs that could be used to diagnostically identify putative PPHs. The protein sequence of the functionally characterized pheophytinase, namely the chloroplast localized protein from *Arabidopsis thaliana* described by Schelbert, et al, 2009, Plant Cell 21(3):767-85, was used as query in BLAST analysis on the non-redundant (nr) protein database of the National Center for Biotechnology Information (NCBI). A number of putative PPH genes were found to be present in different plants of the genus *Populus, Vitis, Ricinus, Oryzae* sp., *Nicotiana, Zea* sp, and *Physcomitrella*.

Protein sequences from various species are identified as putative PPHs based on high amino acid sequence identity to the known *Arabidopsis* PPH. Sequence identity of the different putative PPH to the *Arabidopsis* PPH ranges from 50 to 63%, as shown in the table below:

isms such as plants, algae, cyanobacteria and photosynthetic chlorophyll containing bacteria.

These conserved PPH motifs can be used individually to search sequences from genome databases, the microbiome metagenome database (JOT-DOE, USA) for PPHs. A second conserved motif can be used in addition to the first conserved motif in searching for new PPHs. The GNSLGG (SEQ ID NO:15) motif contains the active site serine residue which can be used together with the other 6 motifs to identify new PPH candidates from plants, algae and bacteria.

Example 2

Pheophytinase (e.g., a PPH as prepared in example 1 having pyropheophytinase activity) is tested in crude rape seed oil according to the recipe in table 2:

TABLE 2

|   | | 1 | 2 |
|---|---|---|---|
| Crude rape seed oil | g | 100 | 100 |
| Citric acid, 45% in water | ml | 0.14 | 0.14 |

|   | A. thaliana pheophytinase AT | Oryzae Sativa Osj | Oryzae sativa j2 Osj2 | Zea Mays Zm | Physcomitrella Pp | Nicotiana Tabacum Nt | Vitis Vinifera Vv | Populus Trichocarpa Pt | Ricinus Communis Rc |
|---|---|---|---|---|---|---|---|---|---|
| AT |  | 56 | 58 | 56 | 50 | 56 | 61 | 63 | 62 |
| Osj |  |  | 97 | 79 | 48 | 56 | 61 | 58 | 57 |
| Osj2 |  |  |  | 78 | 50 | 56 | 61 | 58 | 57 |
| Zm |  |  |  |  | 50 | 55 | 60 | 58 | 58 |
| Pp |  |  |  |  |  | 48 | 50 | 50 | 51 |
| Nt |  |  |  |  |  |  | 67 | 60 | 61 |
| Vv |  |  |  |  |  |  |  | 70 | 66 |
| PT |  |  |  |  |  |  |  |  | 66 |
| Rc |  |  |  |  |  |  |  |  |  |

Sequence identity as high as 78%, was observed between the putative maize & rice PPHs. Identified PPHs were derived from the following species, followed by NCBI database accession numbers and SEQ ID and Figure no.s: *Populus trichocarpa* (XP_002314066, SEQ ID NO:5, FIG. 15); *Vitis vinifera* (XP_002271167, SEQ ID NO:6, FIG. 16); *Ricinus communis* (EEF48653, SEQ ID NO:7, FIG. 17); *Oryza sativa* (japonica cultivar-group) (NP_001057593, SEQ ID NO:8, FIG. 18); *Zea mays* (NP_001141976, SEQ ID NO:9, FIG. 19); *Nicotiana tabacum* (CAO99125, SEQ ID NO:10, FIG. 20); *Oryza sativa* Japonica Group (BAG91172, SEQ ID NO:11, FIG. 21); *Physcomitrella patens* subsp. *patens* (XP_001761725, SEQ ID NO:12, FIG. 22a).

Figure 23:
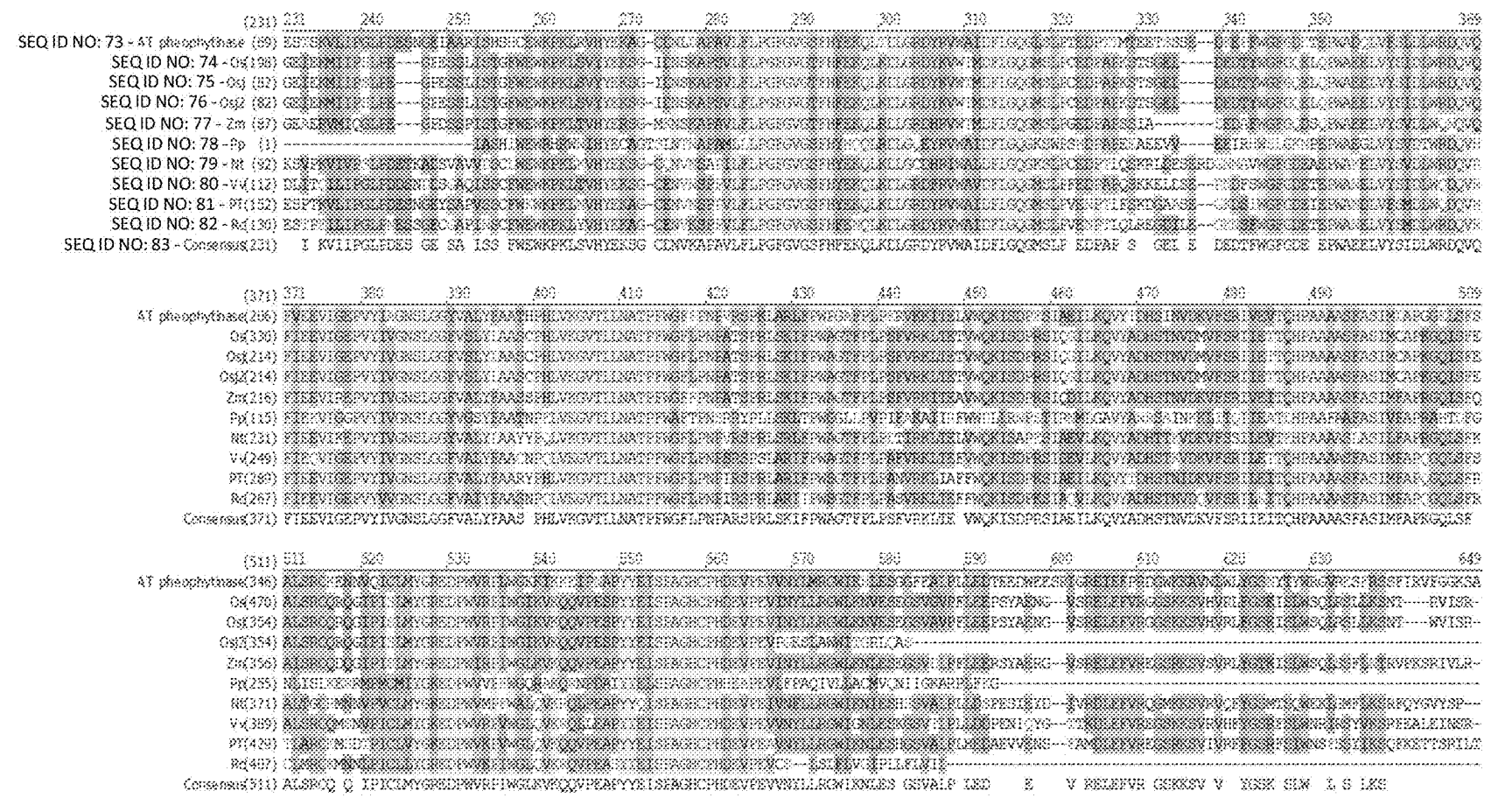

FIG. 23 shows an alignment of the functionally characterized Pheophytin Pheophorbide Hydrolase from *Arabidopsis thaliana* with putative pheophytinases/pyropheophytinases showing several blocks of conserved amino acid residues. The conserved blocks have the following amino acid sequences: LPGFGVG (SEQ ID NO:13), DFLGQG (SEQ ID NO:14), GNSLGG (SEQ ID NO:15), LVK-GVTLLNATPFW (SEQ ID NO:16), HPAA (SEQ ID NO:17), EDPW (SEQ ID NO:18), and SPAGHCPH (SEQ ID NO:19). These conserved blocks can be used to identify new members of pheophytinase/pyropheophytinase family either by searching sequenced genome databases, screening metagenomic libraries or by using these amino acids as degenerate oligonucleotide probes in a PCR to identify new PPH genes present in different chlorophyll containing organ- TABLE 2-continued

|   | | 1 | 2 |
|---|---|---|---|
| NaOH, 10% in water | ml | 0.27 | 0.27 |
| Water | ml | 2.7 | 2.4 |
| Pheophytinase 3 U/ml | ml | 0 | 0.25 |

Crude rape seed oil is heated to 30° C. with agitation. Citric acid is added to the oil and the sample is homogenized with a high shear mixer for 20 seconds After 10 minutes agitation NaOH and water is added. Pheophytinase is then added. The sample is homogenized again with a high shear mixer for 20 seconds. Agitation is continued for 2 hours.

The sample is then heated in a boiling water bath for 10 minutes and then centrifuged at 3000 rcf. for 3 minutes The oil phase is isolated and remaining water in the oil is removed by vacuum distillation at 30° C. and 20 hPa. 75 gram dried oil is heated to 90° C. and 0.75 gram Silica, Trisyl 300 is added. The oil is agitated with silica for 60 minutes at 90° C. The silica is then separated from the oil by centrifugation or filtration.

In the enzymatic treatment of crude rape seed oil more than 90% of the pheophytin and pyropheophytin in the oil is hydrolysed during formation of phytol and pheophorbide/pyropheophorbide respectively. Silica treatment of the oil after enzyme treatment and drying removes 90% of both pheophorbide and pyropheophorbide in the oil.

Example 3

Pheophytinase is tested in crude rape seed oil according to the recipe in table 3.

TABLE 3

|  |  | 1 | 2 |
|---|---|---|---|
| Crude rape seed oil | g | 100 | 100 |
| Immobilized Pheophytinase 5 U/g | ml | 0 | 2 |
| Water | ml | 0.1 | 0.1 |

Crude rape seed oil is heated to 30° C. with agitation and water is added. Pheophytinase immobilized on silica is then added. The sample is agitated for 2 hours at 30° C. and the enzyme is then separated from the oil by centrifugation. By HPLC analysis it is measured that 90% of pheophytin and pyropheophytin are hydrolysed to phytol and pheophorbide/pyropheophorbide respectively.

The oil phase already treated with immobilized pheophytinase is added to 1 gram silica, Trisyl 300. The oil is agitated with silica for 60 minutes at 90° C. The silica is then separated from the oil by centrifugation or filtration.

Silica treatment of the oil after enzyme treatment and drying removes 90% of both pheophorbide and pyropheophorbide. The oil is then deodorized at 240° C. and 0.5 hPa for 1 hour. After deodorization 99% of the pheophorbide and pyropheophorbide produced by the enzyme reaction is removed.

Example 4

Pheophytinase is tested in crude rape seed oil according to the recipe in table 4.

TABLE 4

|  |  | 1 | 2 | 3 |
|---|---|---|---|---|
| Crude rape seed oil | g | 100 | 100 | 100 |
| Citric acid, 45% in water | ml | 0.14 | 0.14 | 0.14 |
| Acyltransferase, LysoMax Oil ® from Danisco A/S, 100 U/ml* | ml |  | 0.1 | 0.1 |
| NaOH, 10% in water | ml | 0.27 | 0.27 | 0.27 |
| Water | ml | 2.7 | 2.6 | 2.4 |
| Immobilized Pheophytinase 5 U/g | g |  |  | 0.25 |

*Lipid acyltransferase activity may be determined as described in WO 2004/064987.

Crude rape seed oil is heated to 55° C. with agitation. Citric acid is added to the oil and the sample is homogenized with a high shear mixer for 20 seconds. After 10 minutes agitation NaOH and water is added. Acyltransferase is then added. The sample is homogenized again with a high shear mixer for 20 second. Agitation is continued for 1 hour.

The samples are then centrifuged at 3000 rcf. for 3 minutes. The oil phase is isolated and remaining water in the oil is removed by vacuum distillation at 60° C. and 20 hPa. 75 gram dried oil is cooled to 30° C. and incubated with immobilized pheophytinase for 1 hr. during agitation. The immobilized enzyme is then removed. The oil is heated to 90° C. and 0.75 gram silica, Trisyl 300 is added. The oil is agitated with silica for 30 minutes at 90° C. The silica is then separated from the oil by centrifugation or filtration. The oil is then deodorized at 250° C. and 0.5 hPa for 60 minutes.

In the enzymatic treatment of crude rape seed oil with pheophytinase more than 95% of the pheophytin and pyropheophytin in the oil is hydrolysed during formation of phytol and pheophorbide/pyropheophorbide respectively. Silica treatment of the oil after enzyme treatment removes 90% of both pheophorbide and pyropheophorbide in the oil. The deodorization process removes 95% of the remaining pheophorbide/pyropheophorbide.

Example 5

In this example, the effect of a deodorization step in the refining process on pheophytin, pheophorbide and pyropheophorbide levels in oil is demonstrated. Deodorization is normally the last step in oil refining. Pheophytin, pheophorbide and pyropheophorbide were tested in a model system of refined rape seed oil where these components were added in known concentrations.

Pheophorbide and pyro-pheophorbide were added to refined rape seed oil at a concentration of 2 mg/kg oil (2 ppm) and pheophytin was added as reference at a concentration of 3 ppm (Table 5).

TABLE 5

|  |  | 1 | 2 | 3 | 4 |
|---|---|---|---|---|---|
| Refined rape seed oil | g | 600 | 600 | 600 | 600 |
| Acetone | ml | 0.600 |  |  |  |
| Pheophorbide, 2 mg/ml | ml |  | 0.600 |  |  |
| Pyropheophorbide, 2 mg/ml in acetone | ml |  |  | 0.600 |  |
| Pheophytin, 0.98 mg/ml in Acetone | ml |  |  |  | 1.840 |

Fluorescence detection of pheophytin, pheophorbide and pyropheophorbide

Solutions 2, 3 and 4 from table 5 were diluted with refined rape seed oil to give concentrations of pheophorbide and pyropheophorbide between 3 to 0.04 ppm and 2 to 0.03 ppm respectively. 200 µl of these samples were transferred to a fluorescence microtiter plate and the fluorescence RFU was measured at 25° C. with excitation of 410 nm emission of 672 nm with results shown in Table 6.

TABLE 6

| Pheophytin mg/ml | RFU | Pheophorbide mg/kg | RFU | Pyropheophorbide mg/kg | RFU |
|---|---|---|---|---|---|
| 3.005 | 5048 | 2.000 | 9375 | 2.000 | 9956 |
| 1.494 | 2613 | 1.005 | 4986 | 0.996 | 5707 |
| 0.757 | 1461 | 0.502 | 2766 | 0.501 | 2929 |
| 0.468 | 935 | 0.309 | 1927 | 0.294 | 2085 |
| 0.307 | 634 | 0.198 | 1190 | 0.213 | 1495 |
| 0.156 | 382 | 0.107 | 687 | 0.110 | 846 |
| 0.081 | 222 | 0.052 | 394 | 0.056 | 449 |
| 0.037 | 146 | 0.028 | 251 | 0.026 | 251 |

Based on the results in table 6 calibration curves were constructed and used to calculate unknown samples.

500 g refined rapeseed oil comprising the components defined in Table 5 was deodorized in a round bottom glass flask at 240° C. and 0.15 mBar with steam injection for one hour.

Oil samples spiked with pheophytin, pheophorbide and pyropheophorbide (Table 5) were deodorized and samples of the oils before and after deodorization were measured on an Fluorescence microtiter plate reader. Based on the calibration curve obtained from standard mixtures of pheophytin, pheophorbide and pyropheophorbide in oil (Table 6) the amount of these components were determined with results shown in Table 7.

TABLE 7

Fluorescence analysis of oils spiked with pheophytin, pheophorbide and pyropheophorbide before and after deodorization

|  | RFU | Pheophorbide ppm | Pyropheophorbide ppm | Pheophytin Ppm |
|---|---|---|---|---|
| Sample 1 before deodorization | 82 | −0.01 | 0.00 | −0.01 |
| Sample 1 after deodorization | 44 | −0.02 | −0.01 | −0.03 |
| Sample 2 before deodorization | 9226 | 1.97 | | |
| Sample 2 after deodorization | 2904 | 0.54 | | |
| Sample 3 before deodorization | 10738 | | 2.20 | |
| Sample 3 after deodorization | 2915 | | 0.46 | |
| Sample 4 before deodorization | 5164 | | | 3.09 |
| Sample 4 after deodorization | 1545 | | | 0.83 |

The results in table 3 clearly indicate that the deodorization process reduces the level of pheophytin, pheophorbide and pyropheophorbide in the oil.

The samples were also analysed by HPLC and the chromatograms of the HPLC analysis is shown in FIGS. 2 to 9. The HPLC chromatograms clearly illustrated the effect of deodorization on the level of pheophytin, pheophorbide and pyropheophorbide. For both, pheophorbide and pyropheophorbide the level after deodorization is below the detection level for these components, and it is therefore not possible to calculate the amount of pheophorbide and pyropheophorbide. Deodorization of oil with pheophytin also removes this component to a level below detection limit, but a new component appears in the sample (FIG. 9) which is expected to be pyropheophytin.

Example 6

In this example it is demonstrated that pheophorbide and pyropheophorbide can be removed from oil in the method of the present invention by adsorption on silica. Silica is used in oil processing to remove polar components including phospholipids, soaps and metal ions, but silica is inefficient in removing chlorophyll, pheophytin and pyropheophytin.

10 gram oil (Table 5) was scaled in a Wheaton glass and 0.1 g Trisyl 300 silica was added. The sample is agitated for 10 minutes. Silica is then removed by centrifugation at 4000 rcf for 5 minutes.

5 gram of the oil phase from centrifugation is scaled in a wheaton glass and 0.050 g Trisyl 300 is added. The sample is agitated for 10 minutes. Silica is then removed by centrifugation at 4000 rcf for 5 minutes.

The silica treatment is conducted at two temperatures 25° C. and 90° C.

Oil samples spiked with pheophytin, pheophorbide and pyropheophorbide (Table 5) were also treated with silica (Trisyl 300). In this experiment the effect of temperature was also investigated. The silica treatment was conducted according to the procedure and the samples before silica treatment and after one and two treatments were analyzed by fluorescence, and the amount of the components were calculated based on calibration curves from standard mixtures of the components (Table 6).

The results from the silica treatment are shown in Table 8.

TABLE 8

|  | Silica Treatment | Temperature °C. | RFU | Pheophorbide ppm | Pyropheophorbide ppm | Pheophytin Ppm |
|---|---|---|---|---|---|---|
| Sample 1 | 0 | 25 | 82 | −0.01 | −0.01 | −0.01 |
| Sample 1 | 1 | 25 | 68 | −0.02 | −0.02 | −0.02 |
| Sample 1 | 2 | 25 | 78 | −0.01 | −0.01 | −0.01 |
| Sample 1 | 1 | 90 | 59 | −0.02 | −0.02 | −0.02 |
| Sample 1 | 2 | 90 | 52 | −0.02 | −0.02 | −0.02 |
| Sample 2 | 0 | 25 | 9226 | 1.97 | | |
| Sample 2 | 1 | 25 | 7410 | 1.53 | | |
| Sample 2 | 2 | 25 | 7012 | 1.44 | | |
| Sample 2 | 1 | 90 | 3606 | 0.68 | | |
| Sample 2 | 2 | 90 | 659 | 0.10 | | |
| Sample 3 | 0 | 25 | 10738 | | 2.20 | |
| Sample 3 | 1 | 25 | 9090 | | 1.78 | |
| Sample 3 | 2 | 25 | 8535 | | 1.64 | |
| Sample 3 | 1 | 90 | 5804 | | 1.03 | |
| Sample 3 | 2 | 90 | 1111 | | 0.16 | |
| Sample 4 | 0 | 25 | 5164 | | | 3.09 |
| Sample 4 | 1 | 25 | 4774 | | | 2.83 |
| Sample 4 | 2 | 25 | 5210 | | | 3.12 |
| Sample 4 | 1 | 90 | 4669 | | | 2.76 |
| Sample 4 | 2 | 90 | 3801 | | | 2.21 |

The results in table 8 confirm that the temperature is very important for the adsorption of pheophorbide and pyropheophorbide on silica. In particular, silica treatment at 90° C. is more efficient at removing pheophorbide and pyropheophorbide than treatment at 25° C. The results clearly confirm that two-step silica treatment is much more efficient than a single silica treatment. The results also indicate that pheophytin is not so efficiently adsorbed onto silica. Based on the results it is concluded that the polar degradation products pheophorbide and pyropheophorbide are more easily adsorbed on silica than pheophytin.

These results suggest the use a combination of silica adsorption and deodorization for removal of pheophorbide and pyropheophorbide during oil refining.

Example 7

Cloning and Expression of a Chlorophyllase from *Triticum aestivum* (Wheat) in *Bacillus subtilis*

Figure 31:
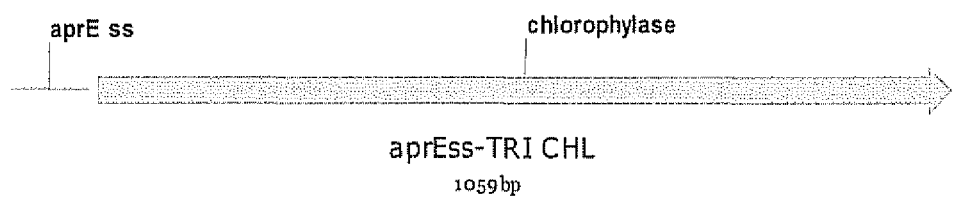
FIG. 31 shows schematically the fusion of the wheat (*Triticum aestivum*) chlorophyllase gene to the aprE signal sequence.

A nucleotide sequence (SEQ ID No. 22) encoding a wheat chlorophyllase (SEQ. ID No. 21, hereinafter wheat chlase) was expressed in *Bacillus subtilis* with the signal peptide of a *B. subtilis* alkaline protease (aprE) (see FIG. 31). For optimal expression in *Bacillus*, a codon optimized gene construct (TRI_CHL) was ordered at GenScript (GenScript Corporation, Piscataway, N.J. 08854, USA).

The construct TRI_CHL contains 20 nucleotides with a BssHII restriction site upstream to the wheat chlase coding region to allow fusion to the aprE signal sequence and a PacI restriction site following the coding region for cloning into the *bacillus* expression vector pBNppt.

The construct TRI_CHL was digested with BssHII and PacI and ligated with T4 DNA ligase into BssHII and PacI digested pBNppt.

Figure 32:
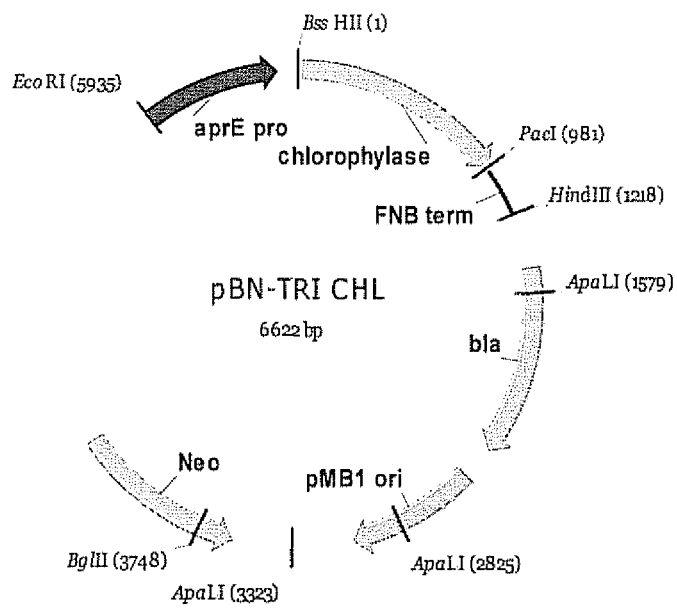
FIG. 32 shows schematically the plasmid pBN-TRI_CHL containing the wheat (*Triticum aestivum*) chlorophyllase gene.

The ligation mixture was transformed into *E. coli* TOP10 cells. The sequence of the BssHII and Pac insert containing the TRI_CHL gene was confirmed by DNA sequencing (DNA Technology A/S, Risskov, Denmark) and one of the correct plasmid clones was designated pBN-TRI_CHL (FIG. 32). pBN-TRI_CHL was transformed into *B. subtilis* strain BG 6002 a derivative of AK 2200, as described in WO 2003/099843.

One neomycin resistant (neoR) transformant was selected and used for expression of the wheat chlase.

Example 8

Cloning and Expression of a Chlorophyllase from *Chlamydomonas reinhardtii* (Green Algae) in *Bacillus subtilis*

Figure 33:
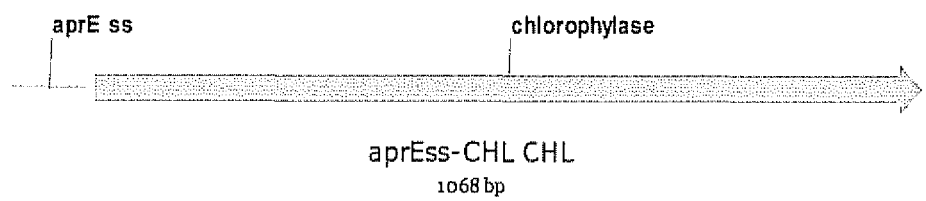
FIG. 33 shows schematically the fusion of the *Chlamydomonas reinhardtii* chlorophyllase gene to the aprE signal sequence.
Figure 34:
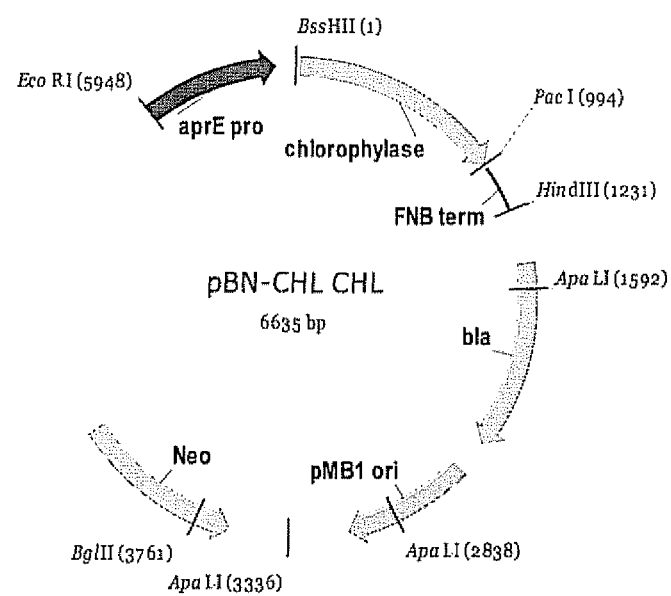
FIG. 34 shows schematically the plasmid pBN-CHL_CHL containing the *Chlamydomonas reinhardtii* chlorophyllase gene.

A nucleotide sequence (SEQ ID No. 24) encoding a *Chlamydomonas* chlorophyllase (SEQ. ID No. 23, hereinafter chlamy chlase) was expressed in *Bacillus subtilis* with the signal peptide of a *B. subtilis* alkaline protease (aprE) (see FIGS. 33 and 34). For optimal expression in *Bacillus*, a codon optimized gene construct (CHL_CHL) was ordered at GenScript (GenScript Corporation, Piscataway, N.J. 08854, USA).

The construct CHL_CHL contains 20 nucleotides with a BssHII restriction site upstream to the chlamy chlase coding region to allow fusion to the aprE signal sequence and a Pad restriction site following the coding region for cloning into the *bacillus* expression vector pBNppt.

The construct CHL_CHL was digested with BssHII and PacI and ligated with T4 DNA ligase into BssHII and PacI digested pBNppt.

The ligation mixture was transformed into *E. coli* TOP10 cells. The sequence of the BssHII and Pac insert containing the CHL_CHL gene was confirmed by DNA sequencing (DNA Technology A/S, Risskov, Denmark) and one of the correct plasmid clones was designated pBN-CHL_CHL (FIG. 20). pBN-CHL_CHL was transformed into B subtilis strain BG 6002 a derivative of AK 2200, as described in WO 2003/099843.

One neomycin resistant (neoR) transformant was selected and used for expression of the chlamy chlase.

Example 9

Cloning and Expression of an N-Terminal Truncated Variant of *Triticum aestivum* Chlorophyllase In this example, a variant of *Triticum aestivum* chlorophyllase was constructed lacking the N-terminal 16 amino acids compared to the wild-type enzyme. This variant is designated *Triticum* Nd1-16 and its amino acid sequence is shown in SEQ ID NO:25. The nucleotide sequence (SEQ ID NO:26) encoding the variant was expressed in *Bacillus subtilis* with the signal peptide of a *B. subtilis* alkaline protease (aprE). For optimal expression in *Bacillus*, a codon optimized gene construct (TRI_CHL-S) was ordered at GenScript (GenScript Corporation, Piscataway, N.J. 08854, USA).

The construct TRI_CHL-S contains 20 nucleotides with a BssHII restriction site upstream to the wheat chlase variant coding region to allow fusion to the aprE signal sequence and a PacI restriction site following the coding region for cloning into the *bacillus* expression vector pBNppt.

The construct TRI_CHL-S was digested with BssHII and PacI and ligated with T4 DNA ligase into BssHII and PacI digested pBNppt.

The ligation mixture was transformed into *E. coli* TOP10 cells. The sequence of the BssHII and Pac insert containing the TRI_CHL gene was confirmed by DNA sequencing (DNA Technology A/S, Risskov, Denmark) and one of the correct plasmid clones was designated pBN-TRI_CHL-S. pBN-TRI_CHL-S was transformed into *B. subtilis* strain BG 6002 a derivative of AK 2200 (See US2003/015859 and WO/2003/099843).

One neomycin resistant (neoR) transformant was selected and used for expression of the wheat chlase.

Example 10

Pyropheophytinase Activity of Chlorophyllases

The pyropheophytinase and pheophytinase activity of the enzymes described in Examples 7 to 9 was determined, and compared to the activity of *Arabidopsis thaliana* chlorophyllase (SEQ ID NO:20). The results are shown in the following table:

| Enzyme | Pheophytinase activity (µmol/min) | Pyropheopytinase activity (µmol/min) | Pheophytin/ pyropheophytin activity ratio |
|---|---|---|---|
| *Arabidopsis* chlase | 0.18 | 0.002 | 90 |
| *Chlamydomonas* chlase (Ex. 8) | 3.06 | 1.90 | 16 |
| *Triticum* chlase (Ex. 7) | 8.25 | 0.167 | 49 |
| *Triticum* Nd1-16 (Ex. 9) | 3.17 | 0.114 | 28 |

Pheophytinase or pyropheophytinase activity as shown in the above table refers to the number of micromoles of substrate (pheophytin or pyropheophytin) hydrolysed per minute in the assay.

The above table shows the activity of various chlorophyllases on pheophytin and pyropheophytin, and the activity ratio is calculated as pheophytinase activity/pyropheophytinase activity. Lowering the activity ratio indicates a shift towards increased ability to hydrolyze pyropheophytin which is an advantage in oils with significant levels of pyropheophytin.

The *Arabidopsis* chlorophyllase has a high ratio of pheophytinase to pyropheophytinase activity. However, surprisingly the enzymes from *Chlamydomonas* and *Triticum* have a much lower activity ratio with relatively increased activity on pyropheophytin. Furthermore, truncation of the N-terminus of chlorophyllases can generate improved variants with a lower activity ratio compared to the full length enzyme, as demonstrated for a variant of the *Triticum* chlorophyllase lacking the N-terminal 16 amino acids compared to the wild-type enzyme.

All publications mentioned in the above specification are herein incorporated by reference, Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. A method for treating a pyropheophytin-containing plant oil, comprising contacting the oil with an enzyme which hydrolyses pyropheophytin, wherein the enzyme has a pheophytinase to pyropheophytinase activity ratio of less than 50, wherein the enzyme comprises an amino acid sequence having at least 85% sequence identity to the amino acid sequence of SEQ ID NO: 21, 23 or 25 wherein the oil is heterologous to the enzyme and wherein as a result of the enzyme's contact with the oil, the concentration of pyropheophytin in the treated oil is reduced by at least 10% compared to the concentration of pyropheophytin present in the oil before treatment.

2. The method according to claim 1, wherein the enzyme has pheophytinase or pheophytin pheophorbide hydrolase activity.

3. The method according to claim 1, wherein the enzyme is from *Chlamydomonas reinhardtii* or *Triticum aestivum*.

4. The method according to claim 1, wherein pyropheophytin in the oil is hydrolysed to form pyropheophorbide, and the method further comprises a step of removing pyropheophorbide from the oil.

5. The method according to claim 4, wherein the method comprises a deodorization step.

6. The method according to claim 4, wherein the method comprises a step of silica treatment.

7. The method according to claim 6, wherein the method comprises two or more silica treatment steps.

8. The method according to claim 6, wherein the silica treatment is performed at 70 to 110° C.

9. The method according to claim 1, wherein the oil is selected from rice bran, soy, canola, palm, olive, cottonseed, corn, palm kernel, coconut, peanut, sesame or sunflower oil.

10. The method according to claim 1, further comprising a hexane extraction and/or degumming step.

* * * * *